(12) United States Patent
Heppner et al.

(10) Patent No.: US 7,098,221 B2
(45) Date of Patent: *Aug. 29, 2006

(54) AMIDE SUBSTITUTED IMIDAZOPYRIDINES

(75) Inventors: Philip D. Heppner, Woodbury, MN (US); Kyle J. Lindstrom, Houlton, WI (US); Bryon A. Merrill, River Falls, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/200,556

(22) Filed: Aug. 10, 2005

(65) Prior Publication Data

US 2005/0282854 A1    Dec. 22, 2005

Related U.S. Application Data

(60) Division of application No. 10/772,170, filed on Feb. 4, 2004, now Pat. No. 6,969,722, which is a continuation of application No. 10/357,995, filed on Feb. 4, 2003, now Pat. No. 6,720,333, which is a continuation of application No. 10/165,229, filed on Jun. 7, 2002, now Pat. No. 6,545,016, which is a continuation-in-part of application No. 10/016,073, filed on Dec. 6, 2001, now abandoned.

(60) Provisional application No. 60/254,228, filed on Dec. 8, 2000.

(51) Int. Cl.
*A61K 31/437* (2006.01)
*C07D 471/04* (2006.01)

(52) U.S. Cl. .................... 514/303; 546/118; 514/234.2

(58) Field of Classification Search ................ 514/303, 514/234.2; 546/118
See application file for complete search history.

(56) References Cited

U.S. PATENT DOCUMENTS

| 3,314,941 A | 4/1967 | Littell et al. |
|---|---|---|
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gerster |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,693,811 A | 12/1997 | Lindstrom |
| 5,741,908 A | 4/1998 | Gerster et al. |
| 5,756,747 A | 5/1998 | Gerster et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,245,776 B1 | 6/2001 | Skwierczynski et al. |
| 6,331,539 B1 | 12/2001 | Crooks et al. |
| 6,376,669 B1 | 4/2002 | Rice et al. |
| 6,451,810 B1 | 9/2002 | Coleman et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,656,938 B1 | 12/2003 | Crooks et al. |
| 6,660,735 B1 | 12/2003 | Crooks et al. |
| 6,660,747 B1 | 12/2003 | Crooks et al. |
| 6,664,260 B1 | 12/2003 | Charles et al. |
| 6,664,264 B1 | 12/2003 | Dellaria et al. |
| 6,664,265 B1 | 12/2003 | Crooks et al. |
| 6,667,312 B1 | 12/2003 | Bonk et al. |
| 6,670,372 B1 | 12/2003 | Charles et al. |
| 6,677,347 B1 | 1/2004 | Crooks et al. |
| 6,677,348 B1 | 1/2004 | Heppner et al. |
| 6,677,349 B1 | 1/2004 | Griesgraber |
| 6,683,088 B1 | 1/2004 | Crooks et al. |
| 6,696,465 B1 | 2/2004 | Dellaria et al. |
| 6,706,728 B1 | 3/2004 | Hedenstrom et al. |
| 6,720,333 B1 | 4/2004 | Dellaria et al. |

(Continued)

FOREIGN PATENT DOCUMENTS

EP    0 394 026    10/1990

(Continued)

OTHER PUBLICATIONS

Wozniak, et al, "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

(Continued)

*Primary Examiner*—Charanjit S. Aulakh
(74) *Attorney, Agent, or Firm*—Dean Ersfeld

(57) ABSTRACT

Imidazopyridine compounds that contain amide functionality at the 1-position are useful as immune response modifiers. The compounds and compositions of the invention can induce the biosynthesis of various cytokines and are useful in the treatment of a variety of conditions including viral diseases and neoplastic diseases.

4 Claims, No Drawings

U.S. PATENT DOCUMENTS

| | | |
|---|---|---|
| 6,743,920 B1 | 6/2004 | Lindstrom et al. |
| 6,756,382 B1 | 6/2004 | Coleman et al. |
| 6,797,718 B1 | 9/2004 | Dellaria et al. |
| 6,818,650 B1 | 11/2004 | Griesgraber |
| 2002/0016332 A1 | 2/2002 | Slade |
| 2002/0055517 A1 | 5/2002 | Smith |
| 2002/0110840 A1 | 8/2002 | Tomai et al. |
| 2003/0130299 A1 | 7/2003 | Crooks et al. |
| 2003/0133913 A1 | 7/2003 | Tomai et al. |
| 2003/0139364 A1 | 7/2003 | Krieg et al. |
| 2003/0161797 A1 | 8/2003 | Miller et al. |
| 2003/0199538 A1 | 10/2003 | Skwierczynski et al. |
| 2004/0014779 A1 | 1/2004 | Gorden et al. |
| 2004/0091491 A1 | 5/2004 | Kedl et al. |
| 2004/0132079 A1 | 7/2004 | Gupta et al. |
| 2004/0141950 A1 | 7/2004 | Noelle et al. |
| 2004/0147543 A1 | 7/2004 | Hays et al. |
| 2004/0162309 A1 | 8/2004 | Gorden et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Lee et al. |
| 2004/0181130 A1 | 9/2004 | Fox et al. |
| 2004/0181211 A1 | 9/2004 | Elliott et al. |
| 2004/0191833 A1 | 9/2004 | Fink et al. |
| 2004/0192585 A1 | 9/2004 | Fox et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2005/0054590 A1 | 3/2005 | Averett |

FOREIGN PATENT DOCUMENTS

| | | |
|---|---|---|
| EP | 1 104 764 | 6/2001 |
| JP | 9-208584 | 8/1997 |
| JP | 9-255926 | 3/1999 |
| JP | 11-222432 | 8/1999 |
| JP | 2000-247884 | 9/2000 |
| WO | WO 02/36592 | 5/2002 |
| WO | WO 02/46194 | 6/2002 |
| WO | WO 02/102377 | 12/2002 |
| WO | WO 03/097641 | 11/2003 |
| WO | WO 04/091500 | 10/2004 |

OTHER PUBLICATIONS

Brennan, et al, "Automated Bioassay of Interferons in Micro-test Plates", *Biotechniques*, Jun./Jul., 78, 1983.

Testerman, et al., "Cytokine Induction by the Immunomodulators Imiquimod and S-27609", *Journal of Leukocyte Biology*, vol. 58, pp. 365-372, Sep. 1995.

Bachman, et al, "Synthesis of Substituted Quinolylamines. Derivatives of 4-Amino-7-Chloroquinoline", *J. Org. Chem*, 15, pp. 1278-1284 (1950).

Jain, et al, "Chemical and Pharmacological Investigations of Some ω-Substituted Alkylamino-3-aminopyridines", *J. Med. Chem.*, 11, pp. 87-92 (1968).

Baranov, et al., *Chem. Abs.* 85, 94362, (1976).

Berènyi, et al, "Ring Transformation of Condensed Dihydro-as-triazines", *J. Heterocyclic Chem.*, 18, pp. 1537-1540 (1981).

Chollet, et al, "Development of a Topically Active Imiquimod Formulation", *Pharmaceutical Development and Technology*, 4(1), pp. 35-43 (1999).

Izumi, et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines", *Bioorganic & Medicinal Chemistry*, 11, pp. 2541-2550 (2003).

AMIDE SUBSTITUTED IMIDAZOPYRIDINES

CROSS REFERENCE TO RELATED APPLICATIONS

This application is a divisional of U.S. application Ser. No. 10/772,170, filed Feb. 4, 2004, now U.S. Pat. No. 6,969,722, which is a continuation of U.S. application Ser. No. 10/357,995, filed Feb. 4, 2003, now U.S. Pat. No. 6,720,333, which is a continuation of U.S. application Ser. No. 10/165,229, filed Jun. 7, 2002, now U.S. Pat. No. 6,545,016, which is a continuation-in-part of Ser. No. 10/016,073, filed Dec. 6, 2001, now abandoned, which claims the benefit of Ser. No. 60/254,228, filed Dec. 8, 2000.

FIELD OF THE INVENTION

This invention relates to imidazopyridine compounds that have amide functionality at the 1-position, and to pharmaceutical compositions containing such compounds. A further aspect of this invention relates to the use of these compounds as immunomodulators, for inducing cytokine biosynthesis in animals, and in the treatment of diseases, including viral and neoplastic diseases. The invention further provides methods of making the compounds and intermediates used in their synthesis.

BACKGROUND OF THE INVENTION

The first reliable report on the 1H-imidazo[4,5-c]quinoline ring system, Backman et al., *J. Org. Chem.* 15, 1278–1284 (1950) describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c]quinolines were reported. For example, Jain et al., *J. Med. Chem.* 11, pp. 87–92 (1968), synthesized the compound 1-[2-(4-piperidyl)ethyl]-1H-imidazo[4,5-c]quinoline as a possible anticonvulsant and cardiovascular agent. Also, Baranov et al., *Chem. Abs.* 85, 94362 (1976), have reported several 2-oxoimidazo[4,5-c]quinolines, and Berenyi et al., *J. Heterocyclic Chem.* 18, 1537–1540 (1981), have reported certain 2-oxoimidazo[4,5-c]quinolines.

Certain 1H-imidazo[4,5-c]quinolin-4-amines and 1- and 2-substituted derivatives thereof were later found to be useful as antiviral agents, bronchodilators and immunomodulators. These are described in, inter alia, U.S. Pat. Nos. 4,689,338; 4,698,348; 4,929,624; 5,037,986; 5,268,376; 5,346,905; and 5,389,640.

Substituted 1H-imidazopyridine-4-amine compounds useful as immune response modifiers are described in U.S. Pat. Nos. 5,446,153; 5,494,916; and 5,644,063. The compounds described in these patents do not have amine containing substitution at the 1-position. Certain 1H-imidazo[4,5-c]quinolin-4-amines that have amide, sulfonamide, and urea functionality at the 1-position are described in PCT Publications WO 00/76505, WO 00/76518 and U.S. Pat. No. 6,331,539. The disclosure of all the above-mentioned patents and published patent applications are incorporated herein by reference.

Despite these recent discoveries of compounds that are useful as immune response modifiers, there is a continuing need for compounds that have the ability to modulate the immune response, by induction of cytokine biosynthesis or other mechanisms.

SUMMARY OF THE INVENTION

We have found a new class of compounds that are useful in inducing cytokine biosynthesis in animals. Accordingly, this invention provides imidazopyridine-4-amine compounds that have amide functionality at the 1-position. The compounds which have been found to be useful inducers of cytokine biosynthesis are defined by Formula (I), which is described in more detail infra. Formula (I) is as follows:

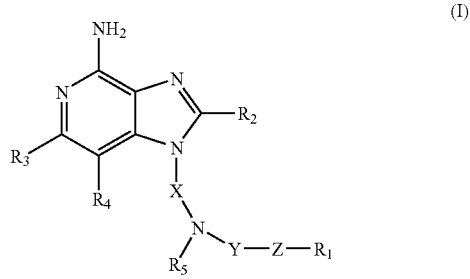

wherein X, Y, Z, $R_1$, $R_2$, $R_3$, $R_4$, and $R_5$ are as defined herein.

The compounds of Formula (I) are useful as immune response modifiers due to their ability to induce cytokine biosynthesis and otherwise modulate the immune response when administered to animals. This makes the compounds useful in the treatment of a variety of conditions such as viral diseases and tumors that are responsive to such changes in the immune response.

The invention further provides pharmaceutical compositions containing the immune response modifying compounds, and methods of inducing cytokine biosynthesis in an animal, treating a viral infection in an animal, and/or treating a neoplastic disease in an animal by administering a compound of Formula (I) to the animal.

In addition, the invention provides methods of synthesizing the compounds of the invention and intermediates useful in the synthesis of these compounds.

DETAILED DESCRIPTION OF THE INVENTION

As mentioned earlier, we have found that certain compounds induce cytokine biosynthesis and modify the immune response in animals. Such compounds are represented by Formula (I) below:

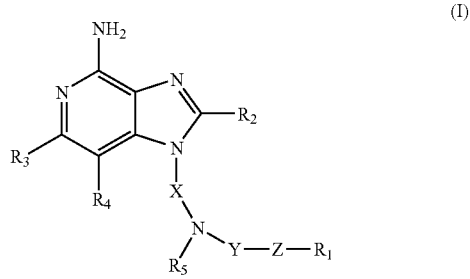

wherein
- X is alkylene or alkenylene;
- Y is —CO— or —CS—;
- Z is a bond, —O—, or —S—;
- $R_1$ is aryl, heteroaryl, heterocyclyl, alkyl or alkenyl, each of which may be unsubstituted or substituted by one or more substituents independently selected from the group consisting of:
  - -alkyl;

-alkenyl;
-aryl;
-heteroaryl;
-heterocyclyl;
-substituted cycloalkyl;
-substituted aryl;
-substituted heteroaryl;
-substituted heterocyclyl;
—O-alkyl;
—O-(alkyl)$_{0-1}$-aryl;
—O-(alkyl)$_{0-1}$-substituted aryl;
—O-(alkyl)$_{0-1}$-heteroaryl;
—O-(alkyl)$_{0-1}$-substituted heteroaryl;
—O-(alkyl)$_{0-1}$-heterocyclyl;
—O-(alkyl)$_{0-1}$-substituted heterocyclyl;
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-substituted aryl;
—S(O)$_{0-2}$-(alkyl)$_{0-1}$-heteroaryl;
—S(O)$_{0-2}$-(alkyl)$_{0-1}$-substituted heteroaryl;
—S(O)$_{0-2}$-(alkyl)$_{0-1}$-heterocyclyl;
—S(O)$_{0-2}$-(alkyl)$_{0-1}$-substituted heterocyclyl;
-(alkyl)$_{0-1}$-N(R$_6$)$_2$;
-(alkyl)$_{0-1}$-NR$_6$—CO—O-alkyl;
-(alkyl)$_{0-1}$-NR$_6$—CO-alkyl;
-(alkyl)$_{0-1}$-NR$_6$—CO-aryl;
-(alkyl)$_{0-1}$-NR$_6$—CO-substituted aryl;
-(alkyl)$_{0-1}$-NR$_6$—CO-heteroaryl;
-(alkyl)$_{0-1}$-NR$_6$—CO-substituted heteroaryl;
—N$_3$;
-halogen;
-haloalkyl;
-haloalkoxy;
—CO-haloalkyl;
—CO-haloalkoxy;
—NO$_2$;
—CN;
—OH;
—SH; and in the case of alkyl, alkenyl, and heterocyclyl, oxo;
R$_2$ is selected from the group consisting of:
-hydrogen;
-alkyl;
-alkenyl;
-aryl;
-substituted aryl;
-heteroaryl;
-substituted heteroaryl;
-alkyl-O-alkyl;
-alkyl-S-alkyl;
-alkyl-O-aryl;
-alkyl-S-aryl:
-alkyl-O-alkenyl;
-alkyl-S-alkenyl; and
-alkyl or alkenyl substituted by one or more substituents selected from the group consisting of:
—OH;
-halogen;
—N(R$_6$)$_2$;
—CO—N(R$_6$)$_2$;
—CS—N(R$_6$)$_2$;
—SO$_2$—N(R$_6$)$_2$;
—NR$_6$—CO—C$_{1-10}$ alkyl;
—NR$_6$—CS—C$_{1-10}$ alkyl;
—NR$_6$—SO$_2$—C$_{1-10}$ alkyl;
—CO—C$_{1-10}$ alkyl;
—CO—O—C$_{1-10}$ alkyl;
—N$_3$;
-aryl;
-substituted aryl;
-heteroaryl;
-substituted heteroaryl;
-heterocyclyl;
-substituted heterocyclyl;
—CO-aryl;
—CO-(substituted aryl);
—CO-heteroaryl; and
—CO-(substituted heteroaryl);
R$_3$ and R$_4$ are independently selected from the group consisting of hydrogen, alkyl, alkenyl, halogen, alkoxy, amino, alkylamino, dialkylamino and alkylthio;
each R$_5$ is independently H or C$_{1-10}$ alkyl, or R$_5$ can join with X to form a ring that contains one or two hetero atoms; or when R$_1$ is alkyl, R$_5$ and R$_1$ can join to form a ring;
each R$_6$ is independently H or C$_{1-10}$ alkyl;
or a pharmaceutically acceptable salt thereof.

Preparation of the Compounds

Compounds of the invention can be prepared according to Reaction Scheme I where R$_1$, R$_2$, R$_3$, R$_4$, R$_5$, X, Y and Z are as defined above, Bn is benzyl and R' is alkyl of one to four carbon atoms, perfluoroalkyl of one to four carbon atoms, phenyl, or phenyl substituted by halogen or alkyl of one to four carbon atoms.

In step (1) of Reaction Scheme I a 3-nitropyridine-2,4-disulfonate of Formula X is reacted with an amine of Formula R$_1$-Z-Y—N(R$_5$)—X—NH$_2$ to provide a 3-nitro-4-aminopyridine-2-sulfonate of Formula XI. Due to the presence of two sulfonate groups that could in principle be displaced, the reaction may provide a mixture of products that can be readily separated using conventional techniques such as column chromatography. The reaction is preferably carried out by adding the amine to a solution of a compound of Formula X in a suitable solvent such as dichloromethane in the presence of a tertiary amine such as triethylamine. As the sulfonate group is a relatively facile leaving group, the reaction can be run at a reduced temperature (0° C.) in order to decrease the amount of undesired 2-aminated and 2,4-diaminated side products. 3-Nitropyridine-2,4-disulfonates are known and can be readily prepared using known synthetic methods, see for example, Lindstom et al., U.S. Pat. No. 5,446,153 and the references cited therein.

In step (2) of Reaction Scheme I a 3-nitro-4-aminopyridine-2-sulfonate of Formula XI is reacted with dibenzylamine to provide a 2-dibenzylamino-3-nitropyridin-4-amine of Formula XII. The reaction is carried out by combining a compound of Formula XI, dibenzylamine, and a tertiary amine such as triethylamine in an inert solvent such as benzene, toluene or xylene and heating the resulting mixture.

In step (3) of Reaction Scheme I the nitro group of a 2-dibenzylamino-3-nitropyridin-4-amine of Formula XII is reduced to an amino group. The reduction is preferably carried out using Ni$_2$B which is generated in situ from sodium borohydride and nickel chloride hydrate in methanol. The reaction is preferably carried out at ambient temperature.

In step (4) of Reaction Scheme I a 2-dibenzylaminopyridine-3,4-diamine of Formula XIII is reacted with a carboxylic acid or an equivalent thereof to provide a 4-dibenzylamino-1H-imidazo[4,5-c]pyridine of Formula XV. Suitable equivalents to carboxylic acid include orthoesters and 1,1-dialkoxyalkyl alkanoates. The carboxylic acid or equivalent is selected such that it will provide the desired $R_2$ substituent in a compound of Formula XV. For example, triethyl orthoformate will provide a compound where $R_2$ is hydrogen and triethyl orthoacetate will provide a compound where $R_2$ is methyl. The reaction can be run in the absence of solvent or in an inert solvent such as toluene. The reaction is run with sufficient heating to drive off any alcohol or water formed as a byproduct of the reaction. Optionally a catlayst such as pyridine hydrochloride can be included.

Alternatively a compound of Formula XV can be prepared in two steps by (a) reacting a diamine of Formula XIII with an acyl halide of formula $R_2C(O)Cl$ or $R_2C(O)Br$ to provide a compound of Formula XIV and then (b) cyclizing. In step (4a) the acyl halide is added to a solution of the diamine in an inert solvent such as acetonitrile, pyridine or dichloromethane. The reaction can be carried out at ambient temperature. In step (4b) the product of step (4a) is heated in an alcoholic solvent in the presence of a base. Preferably the product of step (4a) is refluxed in ethanol in the presence of an excess of triethylamine or heated with methanolic ammonia. Alternatively step (4b) can be carried out by heating the product of step (4a) in pyridine. If step (4a) was carried out in pyridine, step (4b) can be carried out by heating the reaction mixture after analysis indicates that step (4a) is complete.

In step (5) of Reaction Scheme I a 4-dibenzylamino-1H-imidazo[4,5-c]pyridine of Formula XV is hydrogenolyzed to provide the 4-amino-1H-imidazo[4,5-c]pyridine of Formula I. Preferably the compound of Formula XV is heated in formic acid in the presence of palladium hydroxide on carbon. The product or a pharmaceutically acceptable salt thereof can be isolated using conventional methods.

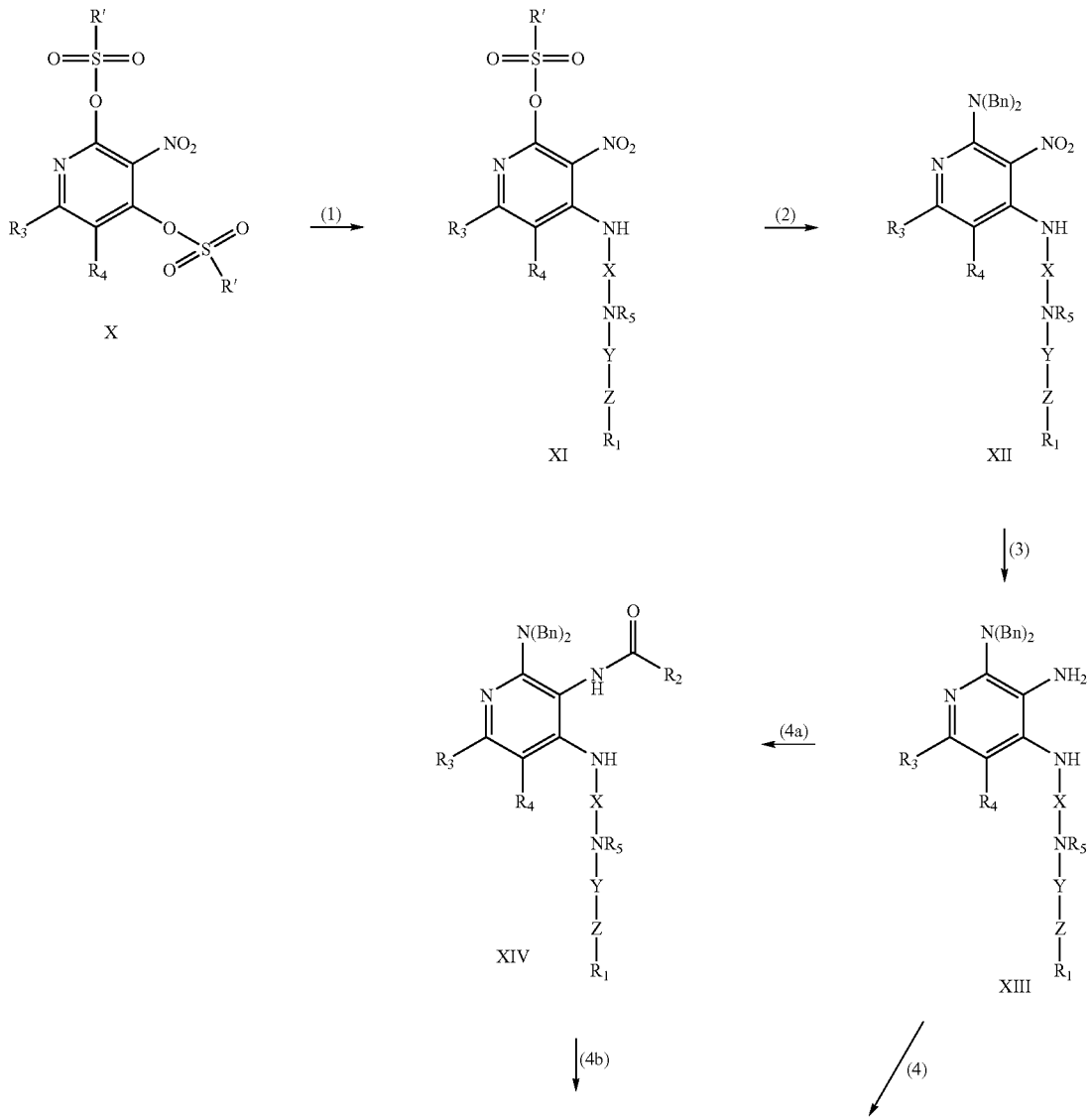

Reaction Scheme I

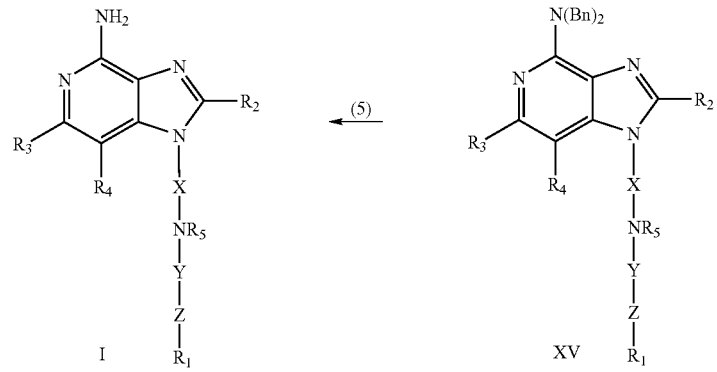

Compounds of the invention can be prepared according to Reaction Scheme II where $R_1$, $R_2$, $R_3$, $R_4$, $R_5$ and X are as defined above, Bn is benzyl, BOC is tert-butoxycarbonyl and W is O or S.

In step (1) of Reaction Scheme II the amine protecting groups of a 1H-imidazo[4,5-c]pyridine of Formula XVI are removed to provide a 1H-imidazo[4,5-c]pyridine of Formula II. Preferably a solution of a compound of Formula XVI in a suitable solvent such as dichloromethane is treated with triflic acid at ambient temperature. Compounds of Formula XVI can be prepared using the synthetic method described in Reaction Scheme I. In step (1) a 2,4-disulfonate of Formula X is reacted with an amine of formula BOC—$NR_5$—X—$NH_2$. Steps 2–4 are then carried out as described above to provide a compound of Formula XVI which is a subgenus of Formula XV.

In step (2a) of Reaction Scheme II, a 1H-imidazo[4,5-c] pyridine of Formula II is reacted with an acid chloride of formula $R_1$—C(O)Cl or an acid anhydride of formula $R_1$—C(O)OC(O)—$R_1$ to provide a 1H-imidazo[4,5-c]pyridin-1-yl amide of Formula XVII which is a subgenus of Formula I. The reaction is preferably carried out by adding the acid chloride or acid anhydride to a solution of a compound of Formula II in a suitable solvent such as dichloromethane or acetonitrile in the presence of a base such as triethylamine. The reaction can be run at a reduced temperature (0° C.) or at ambient temperature. The product or a pharmaceutically acceptable salt thereof can be isolated using conventional methods.

In step (2b) of Reaction Scheme II, a 1H-imidazo[4,5-c] pyridine of Formula II is reacted with an isocyanate of formula $R_1$—N=C=O or with an isothiocyanate of formula $R_1$—N=C=S to provide a 1H-imidazo[4,5-c]pyridin-1-yl urea or thiourea of Formula XVIII. The reaction is preferably carried out by adding the isocyanate or isothiocyanate to a solution of a compound of Formula II in a suitable solvent such as dichloromethane. Optionally, the reaction can be run at a reduced temperature (0° C.). The product or a pharmaceutically acceptable salt thereof can be isolated using conventional methods.

In step (2c) of Reaction Scheme II, a 1H-imidazo[4,5-c] pyridine of Formula II is reacted with a sulfonyl chloride of formula $R_1$—S(O)$_2$Cl or a sulfonic anhydride of formula $R_1$—S(O)$_2$OS(O)$_2$—$R_1$ to provide a 1H-imidazo[4,5-c]pyridin-1-yl sulfonamide of Formula XIX. The reaction is preferably carried out by adding the sulfonyl chloride or sulfonic anhydride to a solution of a compound of Formula II in a suitable solvent such as dichloromethane in the presence of a base such as triethylamine. The reaction can be run at a reduced temperature (0° C.) or at ambient temperature. The product or a pharmaceutically acceptable salt thereof can be isolated using conventional methods.

Reaction Scheme II

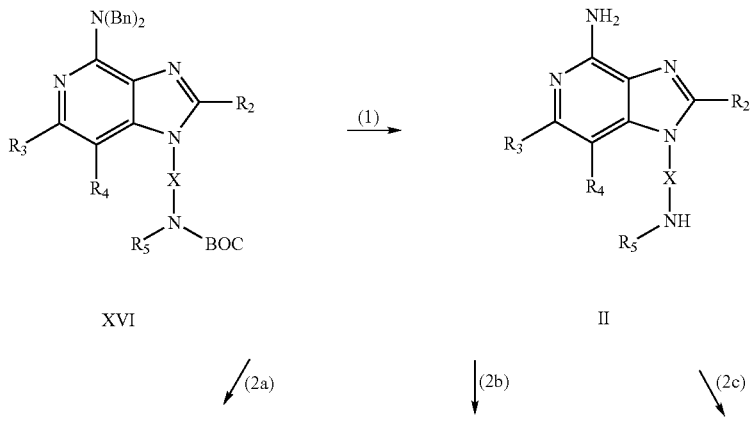

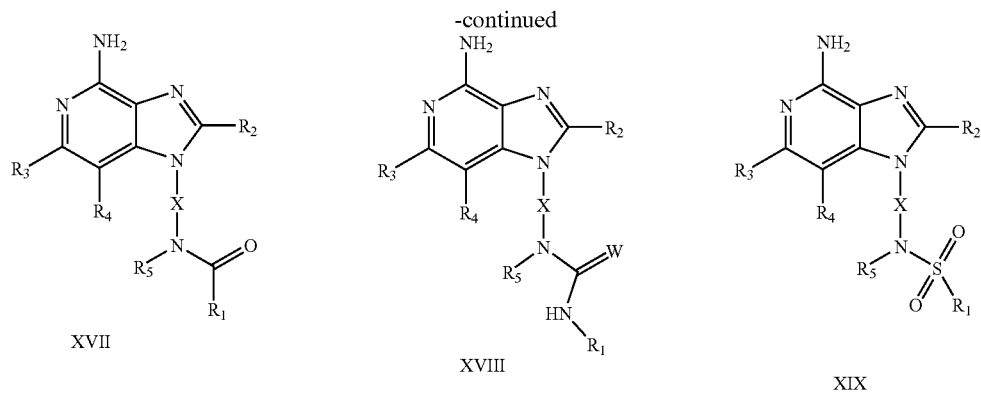

XVII     XVIII     XIX

Compounds of the invention can be prepared according to Reaction Scheme III where $R_1$, $R_2$, $R_3$, $R_4$, $R_5$, $R_6$ and X, are as defined above.

In step (1) of Reaction Scheme III a 1H-imidazo[4,5-c]pyridine of Formula II is reacted with a sulfamoyl chloride of formula $R_1$—$N(R_6)S(O)_2Cl$ to provide a 1H-imidazo[4,5-c]pyridin-1-yl sulfamide of Formula XXI. Preferably the sulfamoyl chloride is added to a solution of the compound of Formula II in a suitable solvent such as 1,2-dichloroethane in the presence of a base such as triethylamine. The reaction can be run at an elevated temperature. The product or a pharmaceutically acceptable salt thereof can be isolated using conventional methods.

Alternatively a sulfamide of Formula XXI can be prepared in two steps by (a) reacting a 1H-imidazo[4,5-c]pyridine of Formula II with sulfuryl chloride to generate in situ a sulfamoyl chloride of Formula XX and then (b) reacting the sulfamoyl choride with an amine of formula $R_1$—$N(R_6)H$. In step (1a) the reaction can be carried out by adding a solution of sulfuryl chloride in dichloromethane to a solution of a compound of Formula II in the presence of 1 equivalent of 4-(dimethylamino)pyridine. The reaction is preferably carried out at a reduced temperature (−78° C.). Optionally, after the addition is complete the reaction mixture can be allowed to warm to ambient temperature. In step (1b) a solution containing 2 equivalents of $R_1$—$N(R_6)H$ and 2 equivalents of triethylamine in dichloromethane is added to the reaction mixture from step (1a). The reaction is preferably carried out at a reduced temperature (−78° C.). The product or a pharmaceutically acceptable salt thereof can be isolated using conventional methods.

Reaction Scheme III

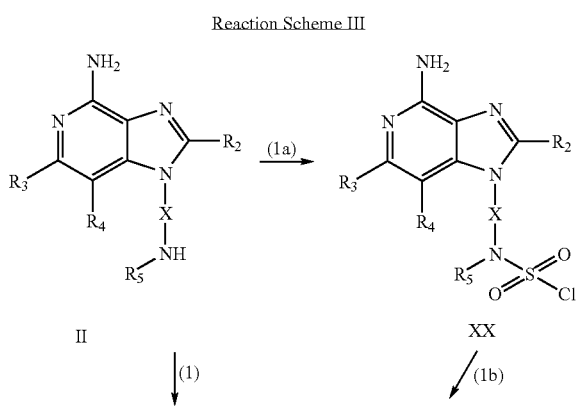

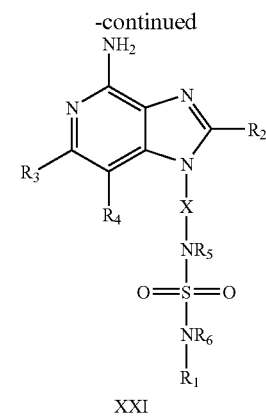

XXI

Compounds of the invention can be prepared according to Reaction Scheme IV where $R_1$, $R_2$, $R_3$, $R_4$, $R_5$, and X are as defined above and BOC is tert-butoxycarbonyl.

In step (1) of Reaction Scheme IV a 2,4-dihydroxy-3-nitropyridine of Formula XXII is chlorinated using conventional chlorinating agents to provide a 2,4-dichloro-3-nitropyridine of Formula XXIII. Preferably a compound of Formula XXII is combined with phosphorous oxychloride and heated. Many 2,4-dihydroxy-3-nitropyridines of Formula XXII are known and others can be readily prepared using known synthetic methods, see for example, Lindstom et al., U.S. Pat. No. 5,446,153 and the references cited therein.

In step (2) of Reaction Scheme IV a 2,4-dichloro-3-nitropyridine of Formula XXIII is reacted with an amine of formula BOC—$NR_5$—X—$NH_2$ to provide a 2-chloro-3-nitropyridine of Formula XXIV. The reaction is preferably carried out by adding the amine to a solution of a compound of Formula XXIII in a suitable solvent such as N,N-dimethylformamide in the presence of a tertiary amine such as triethylamine, and optionally heating.

In step (3) of Reaction Scheme IV a 2-chloro-3-nitropyridine of Formula XXIV is reacted with phenol to provide a 3-nitro-2-phenoxypyridine of Formula XXV. Phenol is reacted with sodium hydride in a suitable solvent such as diglyme or tetrahydrofuran to form the phenoxide. The phenoxide is then reacted at ambient temperature, or optionally at an elevated temperature, with a compound of Formula XXIV.

In step (4) of Reaction Scheme IV a 3-nitro-2-phenoxypyridine of Formula XXV is reduced to provide a 3-amino-2-phenoxypyridine of Formula XXVI. Preferably, the reduction is carried out using a conventional heterogeneous hydrogenation catalyst such as platinum on carbon or palladium on carbon. The reaction can conveniently be carried out on a Parr apparatus in a suitable solvent such as isopropyl alcohol, toluene or mixtures thereof.

In step (5) of Reaction Scheme IV a 3-amino-2-phenoxypyridine of Formula XXVI is reacted with a carboxylic acid or an equivalent thereof to provide a 4-phenoxy-1H-imidazo[4,5-c]pyridine of Formula IV. Suitable equivalents to carboxylic acid include orthoesters, and 1,1-dialkoxyalkyl alkanoates. The carboxylic acid or equivalent is selected such that it will provide the desired $R_2$ substituent in a compound of Formula IV. For example, triethyl orthoformate will provide a compound where $R_2$ is hydrogen and trimethyl orthovalerate will provide a compound where $R_2$ is butyl. The reaction can be run in the absence of solvent or in an inert solvent such as toluene. The reaction is run with sufficient heating to drive off any alcohol or water formed as a byproduct of the reaction. Optionally a catalyst such as pyridine hydrochloride can be included.

Alternatively, step (5) can be carried out by (i) reacting a compound of Formula XXVI with an acyl halide of formula $R_2C(O)Cl$ or $R_2C(O)Br$ and then (ii) cyclizing. In part (i) the acyl halide is added to a solution of a compound of Formula XXV in an inert solvent such as acetonitrile, pyridine or dichloromethane. The reaction can be carried out at ambient temperature. Optionally a catalyst such as pyridine hydrochloride can be included. In part (ii) the product of part (i) is heated in pyridine. If step (i) is run in pyridine, then the two steps can combined into a single step.

In step (6) of Reaction Scheme IV the BOC group is removed from a compound of Formula IV to provide 4-phenoxy-1H-imidazo[4,5-c]pyridine of Formula V. Preferably a solution of a compound of Formula IV in a suitable solvent such as dichloromethane is treated with trifluoroacetic acid or hydrochloric acid at a reduced temperature.

In step (7) of Reaction Scheme IV a 4-phenoxy-1H-imidazo[4,5-c]pyridine of Formula V is converted to a 4-phenoxy-1H-imidazo[4,5-c]pyridin-1-yl sulfonamide of Formula VI using the method of step (2c) of Reaction Scheme II.

In step (8) of Reaction Scheme IV 4-phenoxy-1H-imidazo[4,5-c]pyridin-1-yl sulfonamide of Formula VI is aminated to provide a 4-amino-1H-imidazo[4,5-c]pyridin-1-yl sulfonamide of Formula XIX. The reaction can be carried out by combining a compound of Formula VI with ammonium acetate in a sealed tube and heating (~150° C.). The product or a pharmaceutically acceptable salt thereof can be isolated using conventional methods.

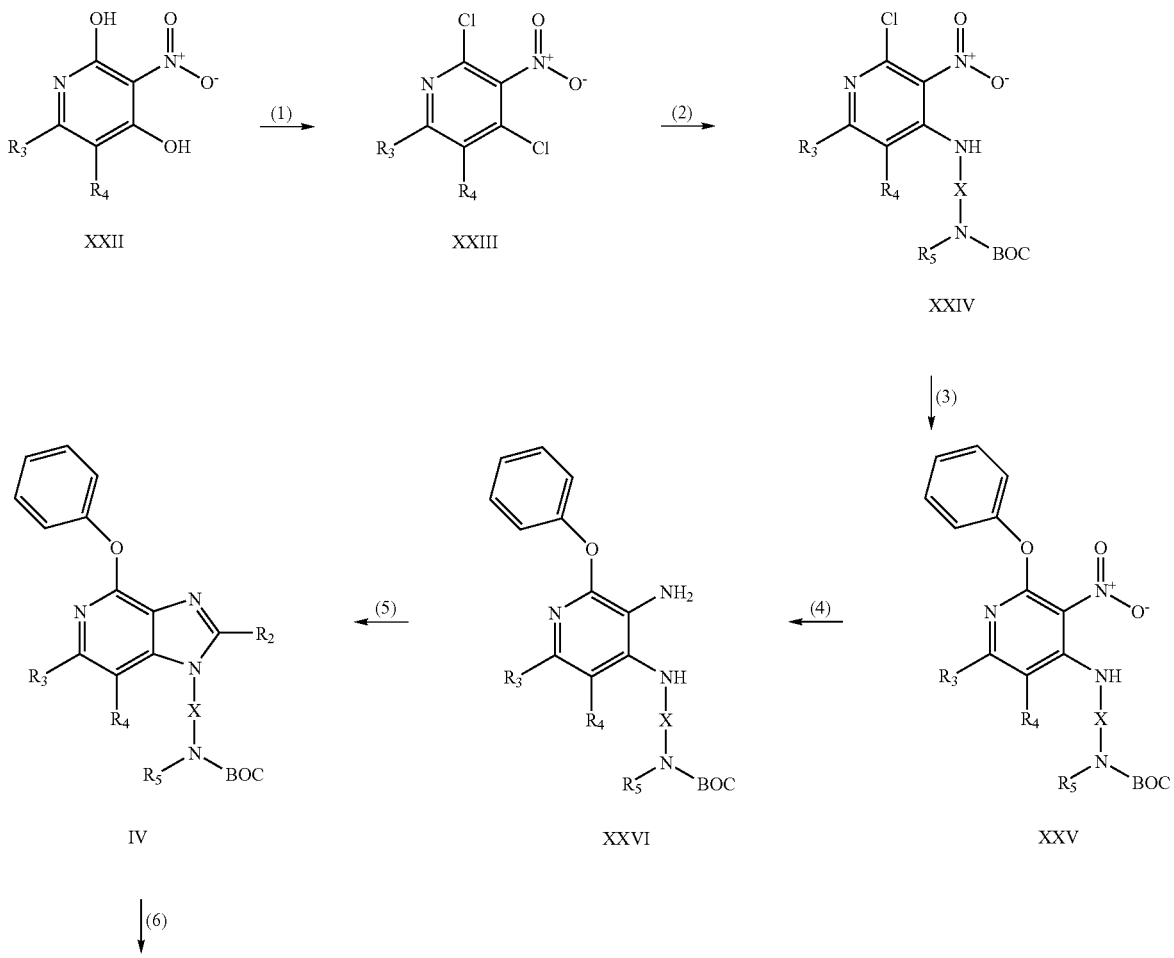

Reaction Scheme IV

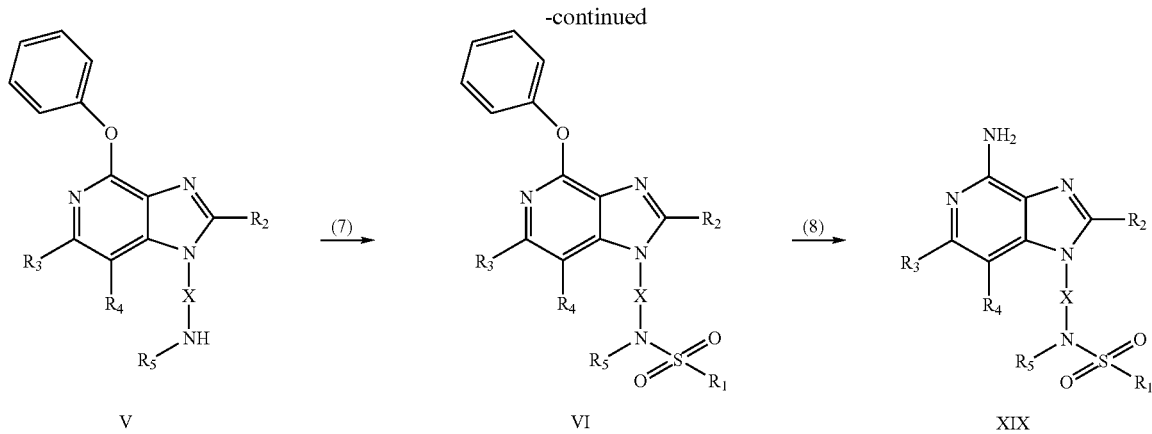

Compounds of the invention can be prepared according to Reaction Scheme V where $R_1$, $R_2$, $R_3$, $R_4$, $R_5$, and X are as defined above and BOC is tert-butoxycarbonyl.

In step (1) of Reaction Scheme V, a 4-phenoxy-1H-imidazo[4,5-c]pyridine of Formula IV is aminated to provide an N-(4-amino-1H-imidazo[4,5-c]pyridin-1-yl)acetamide of Formula XXVIII, which is a subgenus of Formula I. Preferably a compound of Formula IV is combined with ammonium acetate at an elevated temperature (140–160° C.). Optionally, the reaction can be run in a pressure vessel.

In step (2) of Reaction Scheme V, an N-(4-amino-1H-imidazo[4,5-c]pyridin-1-yl)acetamide of Formula XXVIII is hydrolyzed under acidic conditions to provide a 1H-imidazo[4,5-c]pyridin-4-amine of Formula II. Preferably, a compound of Formula XXVIII is combined with hydrochloric acid/ethanol and heated.

In step (3) of Reaction Scheme V, a 1H-imidazo[4,5-c]pyridin-4-amine of Formula II is converted using conventional methods to an amide of Formula XVII, which is a subgenus of Formula I. The reaction can be carried out as described in step (2a) of Reaction Scheme II. The product or a pharmaceutically acceptable salt thereof can be isolated using conventional methods.

Reaction Scheme V

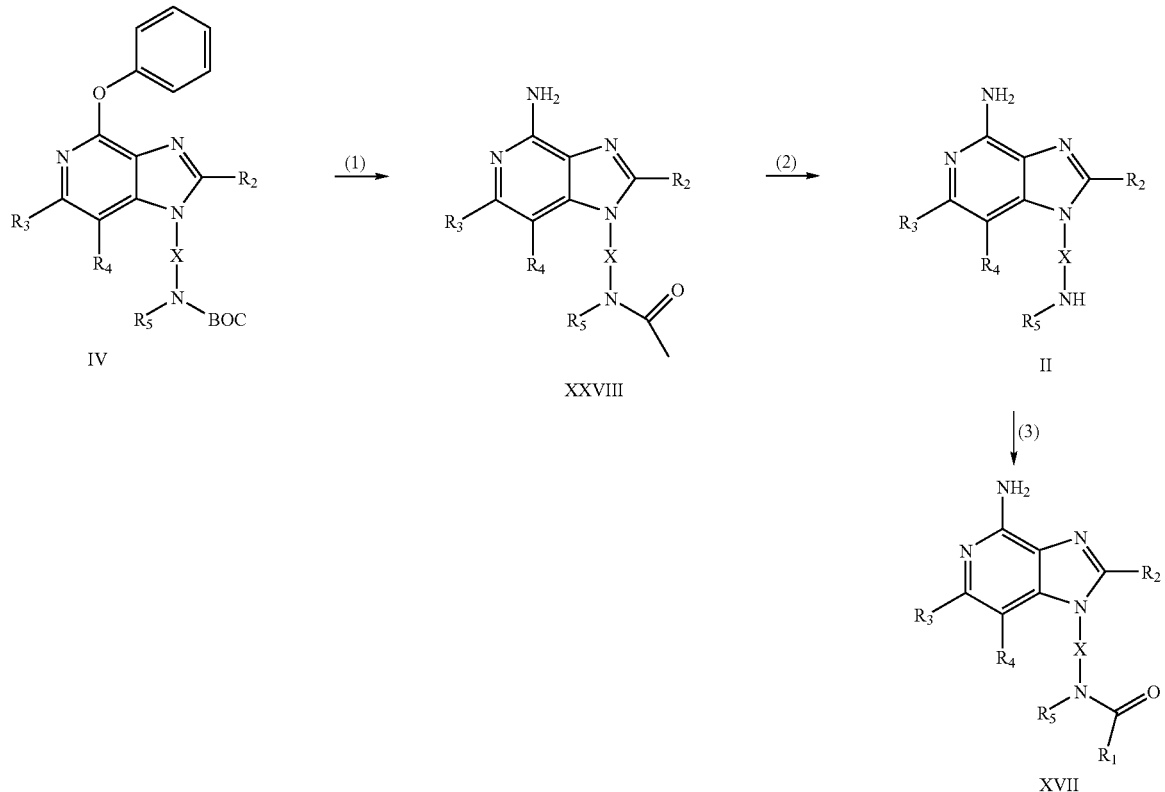

The invention also provides novel compounds useful as intermediates in the synthesis of the compounds of Formula I. These intermediates have structural Formulas (II)–(VI) described in more detail below.

One class of intermediate compounds has Formula (II):

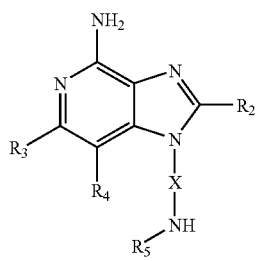

(II)

wherein:
 X is alkylene or alkenylene;
 $R_2$ is selected from the group consisting of:
  -hydrogen;
  -alkyl;
  -alkenyl;
  -aryl;
  -substituted aryl;
  -heteroaryl;
  -substituted heteroaryl;
  -alkyl-O-alkyl;
  -alkyl-S-alkyl;
  -alkyl-O-aryl;
  -alkyl-S-aryl;
  -alkyl-O-alkenyl;
  -alkyl-S-alkenyl; and
  -alkyl or alkenyl substituted by one or more substituents selected from the group consisting of:
   —OH;
   -halogen;
   —N($R_6$)$_2$;
   —CO—N($R_6$)$_2$;
   —CS—N($R_6$)$_2$;
   —SO$_2$—N($R_6$)$_2$;
   —N$R_6$—CO—$C_{1-10}$ alkyl;
   —N$R_6$—CS—$C_{1-10}$ alkyl;
   —N$R_6$—SO$_2$—$C_{1-10}$ alkyl;
   —CO—$C_{1-10}$ alkyl;
   —CO—O—$C_{1-10}$ alkyl;
   —N$_3$;
   -aryl;
   -substituted aryl;
   -heteroaryl;
   -substituted heteroaryl;
   -heterocyclyl;
   -substituted heterocyclyl;
   —CO-aryl;
   —CO-(substituted aryl);
   —CO-heteroaryl; and
   —CO-(substituted heteroaryl)
 $R_3$ and $R_4$ are independently selected from the group consisting of hydrogen, alkyl, alkenyl, halogen, alkoxy, amino, alkylamino, dialkylamino and alkylthio; and
 each $R_5$ is independently H or $C_{1-10}$ alkyl, or $R_5$ can join with X to form a ring that contains one or two hetero atoms;
 each $R_6$ is independently H or $C_{1-10}$ alkyl;

or a pharmaceutically acceptable salt thereof.

Another class of intermediates has the Formula III:

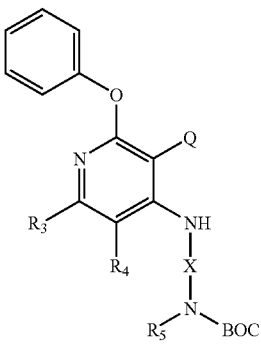

(III)

wherein:
 Q is NO$_2$ or NH$_2$;
 X is alkylene or alkenylene;
 $R_3$ and $R_4$ are independently selected from the group consisting of hydrogen, alkyl, alkenyl, halogen, alkoxy, amino, alkylamino, dialkylamino and alkylthio; and
 each $R_5$ is independently H or $C_{1-10}$ alkyl;

or a pharmaceutically acceptable salt thereof.

Another class of intermediates has the Formula (IV):

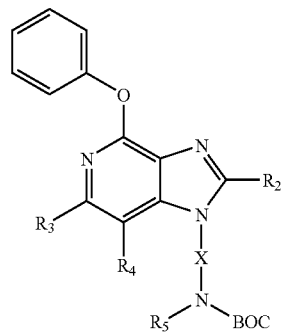

(IV)

wherein:
 X is alkylene or alkenylene;
 $R_2$ is selected from the group consisting of:
  -hydrogen;
  -alkyl;
  -aryl;
  -substituted aryl;
  -heteroaryl;
  -substituted heteroaryl;
  -alkenyl;
  -alkyl-O-alkyl;
  -alkyl-S-alkyl;
  -alkyl-O-aryl;
  -alkyl-S-aryl;
  -alkyl-O-alkenyl;
  -alkyl-S-alkenyl; and
  -alkyl or alkenyl substituted by one or more substituents selected from the group consisting of:
   —OH;
   -halogen;
   —N($R_6$)$_2$;
   —CO—N($R_6$)$_2$;

—CS—N(R$_6$)$_2$;
—SO$_2$—N(R$_6$)$_2$;
—NR$_6$—CO—C$_{1-10}$ alkyl;
—NR$_6$—CS—C$_{1-10}$ alkyl;
—NR$_6$—SO$_2$—C$_{1-10}$ alkyl;
—CO—C$_{1-10}$ alkyl;
—CO—O—C$_{1-10}$ alkyl;
—N$_3$;
-aryl;
-substituted aryl;
-heteroaryl;
-substituted heteroaryl;
-heterocyclyl;
-substituted heterocyclyl;
—CO-aryl;
—CO-(substituted aryl);
—CO-heteroaryl; and
—CO-(substituted heteroaryl)

R$_3$ and R$_4$ are independently selected from the group consisting of hydrogen, alkyl, alkenyl, halogen, alkoxy, amino, alkylamino, dialkylamino and alkylthio; and R$_5$ is H or C$_{1-10}$ alkyl;

each R$_6$ is independently H or C$_{1-10}$ alkyl;

or a pharmaceutically acceptable salt thereof.

Another class of intermediates has the Formula (V):

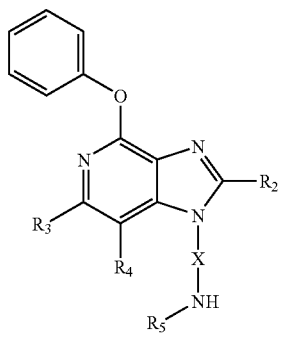

(V)

wherein:
X is alkylene or alkenylene;
R$_2$ is selected from the group consisting of:
-hydrogen;
-alkyl;
-aryl;
-substituted aryl;
-heteroaryl;
-substituted heteroaryl;
-alkenyl;
-alkyl-O-alkyl;
-alkyl-S-alkyl;
-alkyl-O-aryl;
-alkyl-S-aryl;
-alkyl-O-alkenyl;
-alkyl-S-alkenyl; and
-alkyl or alkenyl substituted by one or more substituents selected from the group consisting of:
—OH;
-halogen;
—N(R$_6$)$_2$;
—CO—N(R$_6$)$_2$;
—CS—N(R$_6$)$_2$;
—SO$_2$—N(R$_6$)$_2$;
—NR$_6$—CO—C$_{1-10}$ alkyl;
—NR$_6$—CS—C$_{1-10}$ alkyl;
—NR$_6$—SO$_2$—C$_{1-10}$ alkyl;
—CO—C$_{1-10}$ alkyl;
—CO—O—C$_{1-10}$ alkyl;
—N$_3$;
-aryl;
-substituted aryl;
-heteroaryl;
-substituted heteroaryl;
-heterocyclyl;
-substituted heterocyclyl
—CO-aryl;
—CO-(substituted aryl);
—CO-heteroaryl; and
—CO-(substituted heteroaryl);

R$_3$ and R$_4$ are independently selected from the group consisting of hydrogen, alkyl, alkenyl, halogen, alkoxy, amino, alkylamino, dialkylamino and alkylthio; and R$_5$ is H or C$_{1-10}$ alkyl;

each R$_6$ is independently H or C$_{1-10}$ alkyl;

or a pharmaceutically acceptable salt thereof.

Another class of intermediates has the Formula (VI):

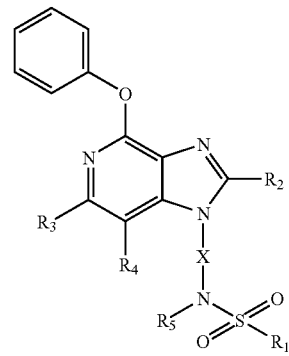

(VI)

wherein:
X is alkylene or alkenylene;
R$_1$ is aryl, heteroaryl, heterocyclyl, C$_{1-20}$ alkyl or C$_{2-20}$ alkenyl, each of which may be unsubstituted or substituted by one or more substituents independently selected from the group consisting of:
-alkyl;
-alkenyl;
-aryl;
-heteroaryl;
-heterocyclyl;
-substituted cycloalkyl;
—O-alkyl;
—O-(alkyl)$_{0-1}$-aryl;
—O-(alkyl)$_{0-1}$-heteroaryl;
—O-(alkyl)$_{0-1}$-heterocyclyl;
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-heteroaryl;
—S(O)$_{0-2}$-(alkyl)$_{0-1}$-heterocyclyl;
-(alkyl)$_{0-1}$—N(R$_6$)$_2$;
-(alkyl)$_{0-1}$-NR$_6$—CO—O-alkyl;

-(alkyl)$_{0-1}$-NR$_6$—CO-alkyl;
-(alkyl)$_{0-1}$-NR$_6$—CO-aryl;
-(alkyl)$_{0-1}$-NR$_6$—CO-heteroaryl;
—N$_3$;
-halogen;
-haloalkyl;
-haloalkoxy;
—CO-haloalkyl;
—CO-haloalkoxy;
—NO$_2$;
—CN;
—OH;
SH; and in the case of alkyl, alkenyl, and heterocyclyl, oxo;

R$_2$ is selected from the group consisting of:
-hydrogen;
-alkyl;
-alkenyl;
-alkyl-O-alkyl;
-alkyl-S-alkyl;
-alkyl-O-aryl;
-alkyl-S-aryl;
-alkyl-O-alkenyl;
-alkyl-S-alkenyl; and
-alkyl or alkenyl substituted by one or more substituents selected from the group consisting of:
—OH;
-halogen;
—N(R$_6$)$_2$;
—CO—N(R$_6$)$_2$;
—CS—N(R$_6$)$_2$;
—SO$_2$—N(R$_6$)$_2$;
—NR$_6$—CO—C$_{1-10}$ alkyl;
—NR$_6$—CS—C$_{1-10}$ alkyl;
—NR$_6$—SO$_2$—C$_{1-10}$ alkyl;
—CO—C$_{1-10}$ alkyl;
—CO—O—C$_{1-10}$ alkyl;
—N$_3$;
-aryl;
-heteroaryl;
-heterocyclyl;
—CO-aryl; and
—CO-heteroaryl;

R$_3$ and R$_4$ are independently selected from the group consisting of hydrogen, alkyl, alkenyl, halogen, alkoxy, amino, alkylamino, dialkylamino and alkylthio; and
R$_5$ is H or C$_{1-10}$ alkyl;
each R$_6$ is independently H or C$_{1-10}$ alkyl;
or a pharmaceutically acceptable salt thereof.

As used herein, the terms "alkyl", "alkenyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl, cyclopropylmethyl, and adamantyl.

The term "haloalkyl" is inclusive of groups that are substituted by one or more halogen atoms, including perfluorinated groups. This is also true of groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

"Heterocyclyl" includes non-aromatic rings or ring systems that contain at least one ring hetero atom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, isothiazolidinyl, and imidazolidinyl.

The aryl, heteroaryl, and heterocyclyl groups can be unsubstituted or substituted by one or more substituents independently selected from the group consisting of alkyl, alkoxy, methylenedioxy, ethylenedioxy, alkylthio, haloalkyl, haloalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylthio, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, aryloxycarbonyl, heteroaryloxycarbonyl, arylthiocarbonyl, heteroarylthiocarbonyl, alkanoyloxy, alkanoylthio, alkanoylamino, arylcarbonyloxy, arylcarbonythio, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylamino, arylalkylcarbonylamino, heteroarylcarbonylamino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonylamino, alkenylaminocarbonylamino, arylaminocarbonylamino, arylalkylaminocarbonylamino, heteroarylaminocarbonylamino, heteroarylalkylaminocarbonylamino and, in the case of heterocyclyl, oxo. If other groups are described as being "substituted" or "optionally substituted", then those groups can also be substituted by one or more of the above enumerated substituents.

Certain substituents are generally preferred. For example, Y is preferably —CO—; Z is preferably a bond; and R$_1$ is preferably C$_{1-4}$ alkyl, aryl, or substituted aryl. Preferred R$_2$ groups include alkyl groups having 1 to 4 carbon atoms (i.e., methyl, ethyl, propyl, isopropyl, n-butyl, sec-butyl, isobutyl, and tert-butyl), methoxyethyl, ethoxymethyl, and cyclopropylmethyl. R$_3$ and R$_4$ are preferably methyl. One or more of these preferred substitutents, if present, can be present in the compounds of the invention in any combination.

The invention is inclusive of the compounds described herein in any of their pharmaceutically acceptable forms, including isomers such as diastereomers and enantiomers, salts, solvates, polymorphs, and the like. In particular, if a compound is optically active, the invention specifically includes each of the compound's enantiomers as well as racemic mixtures of the enantiomers.

Pharmaceutical Compositions and Biological Activity

Pharmaceutical compositions of the invention contain a therapeutically effective amount of a compound of the invention as described above in combination with a pharmaceutically acceptable carrier.

The term "a therapeutically effective amount" means an amount of the compound sufficient to induce a therapeutic effect, such as cytokine induction, antitumor activity, and/or antiviral activity. Although the exact amount of active compound used in a pharmaceutical composition of the invention will vary according to factors known to those of skill in the art, such as the physical and chemical nature of the compound, the nature of the carrier, and the intended dosing regimen, it is anticipated that the compositions of the invention will contain sufficient active ingredient to provide a dose of about 100 ng/kg to about 50 mg/kg, preferably about 10 µg/kg to about 5 mg/kg, of the compound to the subject. Any of the conventional dosage forms may be used, such as tablets, lozenges, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including additional immune response modifiers, antivirals, antibiotics, antibodies, proteins, peptides, oligonucleotides, etc.

The compounds of the invention have been shown to induce the production of certain cytokines in experiments performed according to the tests set forth below. These results indicate that the compounds are useful as immune response modifiers that can modulate the immune response in a number of different ways, rendering them useful in the treatment of a variety of disorders.

Cytokines whose production may be induced by the administration of compounds according to the invention generally include interferon-α (IFN-α) and/or tumor necrosis factor-α (TNF-α) as well as certain interleukins (IL). Cytokines whose biosynthesis may be induced by compounds of the invention include IFN-α, TNF-α, IL-1, IL-6, IL-10 and IL-12, and a variety of other cytokines. Among other effects, these and other cytokines can inhibit virus production and tumor cell growth, making the compounds useful in the treatment of viral diseases and tumors. Accordingly, the invention provides a method of inducing cytokine biosynthesis in an animal comprising administering an effective amount of a compound or composition of the invention to the animal.

Certain compounds of the invention have been found to preferentially induce the expression of IFN-α in a population of hematopoietic cells such as PBMCs (peripheral blood mononuclear cells) containing pDC2 cells (precursor dendritic cell-type 2) without concomitant production of significant levels of inflammatory cytokines.

In addition to the ability to induce the production of cytokines, the compounds of the invention affect other aspects of the innate immune response. For example, natural killer cell activity may be stimulated, an effect that may be due to cytokine induction. The compounds may also activate macrophages, which in turn stimulates secretion of nitric oxide and the production of additional cytokines. Further, the compounds may cause proliferation and differentiation of B-lymphocytes.

Compounds of the invention also have an effect on the acquired immune response. For example, although there is not believed to be any direct effect on T cells or direct induction of T cell cytokines, the production of the T helper type 1 (Th1) cytokine IFN-γ is induced indirectly and the production of the T helper type 2 (Th2) cytokines IL-4, IL-5 and IL-13 are inhibited upon administration of the compounds. This activity means that the compounds are useful in the treatment of diseases where upregulation of the Th1 response and/or downregulation of the Th2 response is desired. In view of the ability of compounds of the invention to inhibit the Th2 immune response, the compounds are expected to be useful in the treatment of atopic diseases, e.g., atopic dermatitis, asthma, allergy, allergic rhinitis; systemic lupus erythematosis; as a vaccine adjuvant; and possibly as a treatment for recurrent fungal diseases and chlamydia.

The immune response modifying effects of the compounds make them useful in the treatment of a wide variety of conditions. Because of their ability to induce the production of cytokines such as IFN-α and/or TNF-α, the compounds are particularly useful in the treatment of viral diseases and tumors. This immunomodulating activity suggests that compounds of the invention are useful in treating diseases such as, but not limited to, viral diseases including genital warts; common warts; plantar warts; Hepatitis B; Hepatitis C; Herpes Simplex Virus Type I and Type II; molluscum contagiosum; variola, particularly variola major; HIV; CMV; VZV; rhinovirus; adenovirus; coronavirus; influenza; and para-influenza; intraepithelial neoplasias such as cervical intraepithelial neoplasia; human papillomavirus (HPV) and associated neoplasias; fungal diseases, e.g. candida, aspergillus, and cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma, melanoma, non-Hodgkin's lymphoma, cutaneous T-cell lymphoma, and other cancers; parasitic diseases, e.g. pneumocystis carnii, cryptosporidiosis, histoplasmosis, toxoplasmosis, trypanosome infection, and leishmaniasis; and bacterial infections, e.g., tuberculosis, and mycobacterium avium. Additional diseases or conditions that can be treated using the compounds of the invention include actinic keratosis; eczema; eosinophilia; essential thrombocythaemia; leprosy; multiple sclerosis; Ommen's syndrome; discoid lupus; Bowen's disease; Bowenoid papulosis; alopecia greata; the inhibition of Keloid formation after surgery and other types of post-surgical scars. In addition, these compounds could enhance or stimulate the healing of wounds, including chronic wounds. The compounds may be useful for treating the opportunistic infections and tumors that occur after suppression of cell mediated immunity in, for example, transplant patients, cancer patients and HIV patients.

An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased over the background level of such cytokines. The precise amount will vary according to factors known in the art but is expected to be a dose of about 100 ng/kg to about 50 mg/kg, preferably about 10 µg/kg to about 5 mg/kg. The invention also provides a method of treating a viral infection in an animal and a method of treating a neoplastic disease in an animal comprising administering an effective amount of a compound or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg.

The invention is further described by the following examples, which are provided for illustration only and are not intended to be limiting in any way.

In the examples below some of the compounds were purified by preparative high performance liquid chromatography using a Waters Fraction Lynx automated purification system. The prep HPLC fractions were analyzed using a Micromass LC-TOFMS and the appropriate fractions were combined and centrifuge evaporated to provide the trifluoroacetate salt of the desired compound. Column: Phenomenex Luna C18(2), 21.2×50 mm, 10 micron particle size, 100 Å pore; flow rate: 25 mL/min.; non-linear gradient elution from 5–95% B in 12 min, then hold at 95% B for 2 min., where A is 0.05% trifluoroacetic acid/water and B is 0.05% trifluoroactic acid/acetonitrile; fraction collection by mass-selective triggering.

EXAMPLE 1

N-[4-(4-Amino-2-butyl-6,7-dimethyl-1H-imidazo[4,5-c]pyridin-1-yl)butyl]benzamide

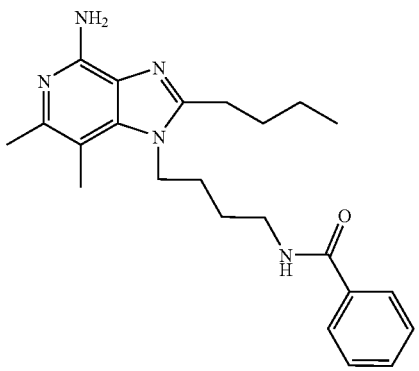

Part A

Triethylamine (16.8 mL, 123.8 mmol) was added to a suspension of 4-hydroxy-5,6-dimethyl-3-nitro-2(1H)-pyridone (7.6 g, 41.2 mmol) in dichloromethane (200 mL). The resulting mixture was cooled in an ice bath. Triflic anhydride (13.7 mL, 82.5 mmol) was added and the reaction mixture was stirred for 30 minutes. Mono-tert-butoxycarbonyl-1,4-butyldiamine (7.6 g, 41.2 mmol) was added in a single portion and the reaction mixture was allowed to warm to ambient temperature. After 1 hour the reaction mixture was washed with aqueous 1% sodium carbonate (2×100 mL), dried over magnesium sulfate and then concentrated under reduced pressure to provide crude product. This material was dissolved in dichloromethane and loaded onto a layer of silica gel. The silica gel was eluted first with dichloromethane to remove some impurities and then with 2–5% ethyl acetate in dichloromethane to recover the desired product. The fractions containing product were combined and then concentrated under reduced pressure to provide 12 g of 4-({4-[(tert-butoxycarbonyl)amino]butyl}amino)-5,6-dimethyl-3-nitropyridin-2-yl trifluoromethanesulfonate as a light yellow oil.

Part B

The material from Part A was combined with triethylamine (2.5 g, 24.7 mmol), dibenzylamine (4.8 g, 24.7 mmol), and toluene (150 mL) and then heated at reflux for 4 hours. The reaction mixture was washed with aqueous 1% sodium carbonate and then concentrated under reduced pressure to provide crude product. This material was dissolved in dichloromethane and loaded onto silica gel. The silica gel was eluted with 2-20% ethyl acetate in dichloromethane. The fractions containing product were combined and then concentrated under reduced pressure to provide ~13 g of tert-butyl 4-{[2-(dibenzylamino)-5,6-dimethyl-3-nitropyridin-4-yl]amino}butylcarbamate.

Part C

Sodium borohydride (1.4 g, 36 mmol) was slowly added to a solution of nickel chloride hydrate (2.9 g, 12.3 mmol) in methanol and the resulting mixture was stirred for 30 minutes. A solution of the material from Part B in methanol was added in a single portion. Sodium borohydride was slowly added until the foaming was colorless. The reaction mixture was filtered. The filtrate was concentrated under reduced pressure. The resulting residue was combined with dichloromethane and the mixture was filtered to remove salts. The filtrate was concentrated under reduced pressure to provide ~12 g of tert-butyl 4-{[3-amino-2-(dibenzylamino)-5,6-dimethylpyridin-4-yl]amino}butylcarbamate.

Part D

Valeryl chloride (3 mL, 24.7 mmol) was added to a solution of the material from Part C in acetonitrile (200 mL). The reaction mixture was stirred at ambient temperature. The reaction mixture was concentrated under reduced pressure. The residue was combined with ethanol and triethylamine (5 g, 49 mmol.). The reaction mixture was heated at reflux overnight and then concentrated under reduced pressure. The resulting residue was partitioned between dichloromethane and water. The dichloromethane layer was separated and then loaded onto a silica gel column. The column was eluted with 9:90:1 ethyl acetate:dichloromethane:methanol. The fractions containing product were combined and then concentrated under reduced pressure to provide 6.5 g of tert-butyl 4-[2-butyl-4-(dibenzylamino)-6,7-dimethyl-1H-imidazo[4,5-c]pyridin-1-yl]butylcarbamate as an oil.

Part E

Triflic acid (16 g, 107 mmol) was added to a solution of the material from Part D (6.5 g, 11.4 mmol) in dichloromethane (250 mL). The resulting mixture was stirred overnight. Ammonium hydroxide (50 mL) and water (100 mL) were added and the resulting mixture was stirred for 30 minutes. The layers were separated and the aqueous fraction was extracted with dichloromethane (100 mL). The organic fractions were combined, washed with 1% aqueous sodium carbonate, washed with brine and concentrated under reduced pressure. The residue was combined with methanol (30 mL), stirred for 30 minutes and filtered. The filtrate was concentrated under reduced pressure and the resulting residue was combined with 1% aqueous sodium carbonate and stirred. The mixture was extracted with hexane to remove organic impurities. The aqueous layer contained an insoluble oil that was extracted with dichloromethane. The organic layer was combined with magnesium sulfate, stirred for 5 minutes and filtered. The filtrate was concentrated under reduced pressure to provide a solid which was recrystallized from toluene to provide 1 g of 1-(4-aminobutyl)-2-butyl-6,7-dimethyl-1H-imidazo[4,5-c]pyridin-4-amine.

Part F

Triethylamine (0.07 mL, 0.5 mmol) was added to a solution of 1-(4-aminobutyl)-2-butyl-6,7-dimethyl-1H-imidazo[4,5-c]pyridin-4-amine (150 mg, 0.5 mmol) in dichloromethane (150 mL). The reaction mixture was cooled in an ice bath. Benzoyl chloride (0.07 mL, 0.5 mmol) was added and the reaction mixture was removed from the ice bath. The reaction mixture was washed twice with water and then concentrated under reduced pressure. The resulting residue was purified by flash chromatography eluting with 10% methanol in dichloromethane to provide an oily brown material. This material was dissolved in a minimum amount of isopropanol and then ethanesulfonic acid (55 mg, 0.5 mmol) was added with stirring. The reaction mixture was stirred at ambient temperature for ~1 hour and then heated briefly in a sand bath until it became homogeneous. The solution was allowed to cool to ambient temperature and then was chilled in an ice bath. The resulting precipitate was isolated by filtration to provide 111 mg of N-[4-(4-amino-2-butyl-6,7-dimethyl-1H-imidazo[4,5-c]pyridin-1-yl)butyl]benzamide as a crystalline solid, m.p. 127.8–128.8° C.

Analysis: Calculated for $C_{23}H_{31}N_5O$: % C, 70.20; % H, 7.94; % N, 17.80. Found: % C, 69.82; % H, 7.70; % N, 17.68.

EXAMPLE 2

N-[4-(4-Amino-2-butyl-6,7-dimethyl-1H-imidazo[4,5-c]pyridin-1-yl)butyl]methanesulfonamide

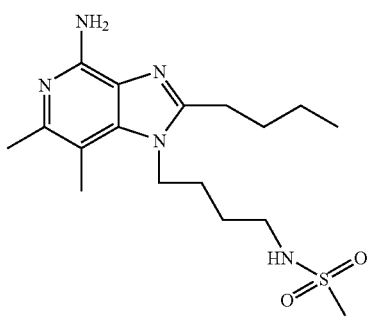

Triethylamine (0.07 mL, 0.5 mmol) was added to a solution of 1-(4-aminobutyl)-2-butyl-6,7-dimethyl-1H-imidazo[4,5-c]pyridin-4-amine (150 mg, 0.5 mmol) in dichloromethane (160 mL). The reaction mixture was cooled in an ice bath. Methanesulfonic anhydride (90 mg, 0.5 mmol) was added and the reaction mixture was removed from the ice bath. The reaction mixture was stirred for 35 minutes. The reaction mixture was washed three times with water, concentrated under reduced pressure, and triturated with a minimum volume of methyl acetate. The resulting crystalline solid was isolated by filtration and then dried in an Abderhalden drying apparatus to provide 94 mg of N-[4-(4-amino-2-butyl-6,7-dimethyl-1H-imidazo[4,5-c]pyridin-1-yl)butyl]methanesulfonamide, m.p. 130–130.5° C.

Analysis: Calculated for $C_{17}H_{29}N_5O_2S$: % C, 55.56; % H, 7.95; % N, 19.06. Found: % C, 55.37; % H, 7.89; % N, 18.03.

EXAMPLE 3

N-[4-(4-Amino-2-butyl-6,7-dimethyl-1H-imidazo[4,5-c]pyridin-1-yl)butyl]-4-fluorobenzenesulfonamide Hydrate

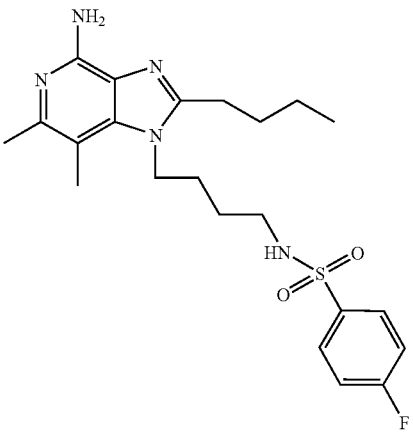

Triethylamine (0.07 mL, 0.5 mmol) was added to a solution of 1-(4-aminobutyl)-2-butyl-6,7-dimethyl-1H-imidazo[4,5-c]pyridin-4-amine (150 mg, 0.5 mmol) in dichloromethane (150 mL). The reaction mixture was cooled in an ice bath. 4-fluorobenzenesulfonyl chloride (113 mg, 0.5 mmol) was added and the reaction mixture was removed from the ice bath. The reaction mixture was stirred at ambient temperature for 48 hours. The reaction mixture was washed with water (2×150 mL) and then concentrated under reduced pressure. The resulting residue was recrystallized from methyl acetate and then dried in an Abderhalden drying apparatus to provide 50 mg of N-[4-(4-amino-2-butyl-6,7-dimethyl-1H-imidazo[4,5-c]pyridin-1-yl)butyl]-4-fluorobenzenesulfonamide hydrate as a white crystalline solid, m.p. 133.1–133.7° C.

Analysis: Calculated for $C_{22}H_{30}FN_5O_2S \cdot H_2O$: % C, 56.75; % H, 6.93; % N, 15.04. Found: % C, 56.99; % H, 6.58; % N, 15.24.

EXAMPLE 4

N-[4-(4-Amino-2-butyl-6,7-dimethyl-1H-imidazo[4,5-c]pyridin-1-yl)butyl]-N'-phenylurea

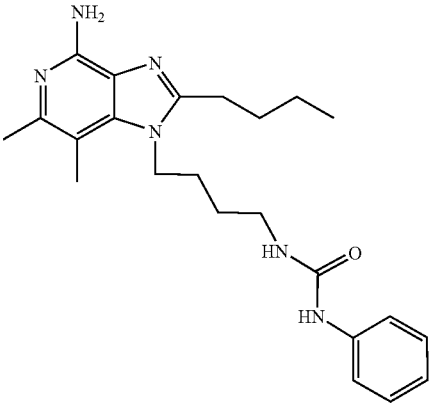

Phenylisocyanate (0.056 mL, 0.5 mmol) was added to a chilled solution of of 1-(4-aminobutyl)-2-butyl-6,7-dimethyl-1H-imidazo[4,5-c]pyridin-4-amine (150 mg, 0.5 mmol) in dichloromethane (150 mL). The ice bath was removed. A white precipitate formed after 5 minutes. The reaction mixture was allowed to stir for 30 minutes and then it was concentrated under reduced pressure to provide an off-white crystalline solid. This material was isolated by filtration using a small amount of diethyl ether to transfer the material to the filter and then dried in an Abderhalden drying apparatus to provide 185 mg of N-[4-(4-amino-2-butyl-6,7-dimethyl-1H-imidazo[4,5-c]pyridin-1-yl)butyl]-N'-phenylurea, m.p. 195.8–196.8° C.

Analysis: Calculated for $C_{23}H_{32}N_6O$: % C, 67.62; % H, 7.89; % N, 20.57. Found: % C, 66.84; % H, 7.71; % N, 20.54.

EXAMPLE 5

N-[4-(4-Amino-2-butyl-6,7-dimethyl-1H-imidazo[4,5-c]pyridin-1-yl)butyl]-N'-phenylthiourea Hydrate

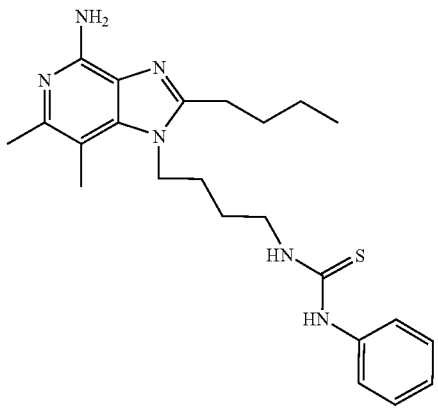

Using the method of Example 4,1-(4-aminobutyl)-2-butyl-6,7-dimethyl-1H-imidazo[4,5-c]pyridin-4-amine (100 mg, 0.35 mmol) was reacted with phenylisothiocyanate (0.041 mL, 0.35 mmol) to provide 97 mg of N-[4-(4-amino-2-butyl-6,7-dimethyl-1H-imidazo[4,5-c]pyridin-1-yl)butyl]-N'-phenylthiourea hydrate as a white crystalline solid, m.p. 160.0–160.8° C.

Analysis: Calculated for $C_{23}H_{32}N_6S \cdot H_2O$: % C, 62.41; % H, 7.74; % N, 18.99. Found: % C, 62.39; % H, 7.47; % N, 18.52.

EXAMPLE 6

N'-[4-(4-Amino-2-butyl-6,7-dimethyl-1H-imidazo[4,5-c]pyridin-1-yl)butyl]-N,N-dimethylsulfamide

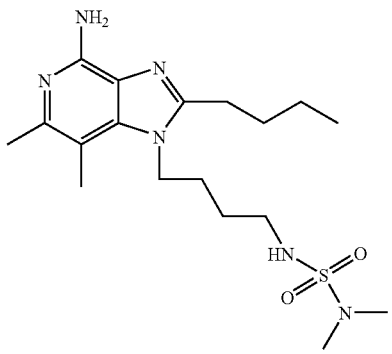

Triethylamine (0.031 mL, 0.23 mmol) was added to a solution of 1-(4-aminobutyl)-2-butyl-6,7-dimethyl-1H-imidazo[4,5-c]pyridin-4-amine (67 mg, 0.23 mmol) in dichloromethane (45 mL). The reaction mixture was cooled in an ice bath. Dimethylsulfamoyl chloride (0.025 mL, 0.23 mmol) was added. The reaction mixture was removed from the ice bath. The reaction mixture was allowed to stir at ambient temperature for ~113 hours. Analysis by HPLC indicated that the reaction was not complete. The dichloromethane was removed under reduced pressure. 1,2-Dichloroethane (50 mL) was added and the reaction mixture was heated to 60° C. After 3 hours, more dimethylsulfamoyl chloride (2.5 µL) was added and heating was continued. After 22 hours the reaction temperature was raised to reflux and the reaction mixture was refluxed for 100 hours. The reaction mixture was extracted twice with water. The aqueous fractions were combined and concentrated under reduced pressure. The resulting residue was recrystallized from methyl acetate to provide 10 mg of N'-[4-(4-amino-2-butyl-6,7-dimethyl-1H-imidazo[4,5-c]pyridin-1-yl)butyl]-N,N-dimethylsulfamide as an off-white crystalline solid, m.p. 129.5–131° C. M/Z 397.1 $(M+H)^+$.

EXAMPLE 7

N-[4-(4-amino-2,6,7-trimethyl-1H-imidazo[4,5-c]pyridin-1-yl)butyl]methanesulfonamide

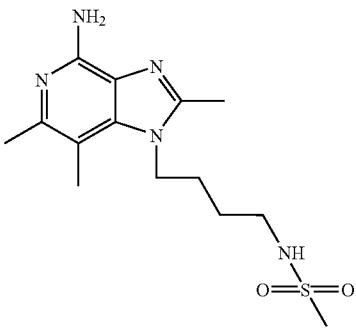

Part A

A mixture of 5,6-dimethyl-3-nitropyridine-2,4-diol (60.0 g, 326 mmol) and phosphorus oxychloride (600 mL) was heated at reflux for 2 hrs. The reaction mixture was concentrated under reduced pressure. The resulting residue was combined with ethyl acetate (300 mL) and then filtered. The filtrate was washed with aqueous sodium bicarbonate solution. The layers were separated and aqueous layer was extracted twice with ethyl acetate. The organic layers were combined, dried with magnesium sulfate and then concentrated under reduced-pressure to provide a brown solid. This material was purified by chromatography (silica gel eluting with 60/40 ethyl acetate/hexanes) to provide 55 g of 2,4-dichloro-5,6-dimethyl-3-nitropyridine.

Part B

Tert-butyl 4-aminobutylcarbamate (60 g, 339 mmol) was slowly added to a mixture of 2,4-dichloro-5,6-dimethyl-3-nitropyridine (50 g, 226 mmol), anhydrous N,N-dimethylformamide (500 mL) and triethylamine (50 mL, 339 mmol). The reaction mixture was allowed to stir overnight and then it was concentrated under reduced pressure to provide an oil. The oil was dissolved in ethyl acetate and then washed with water. The organic layer was dried over magnesium sulfate and then concentrated under reduced pressure to provide a dark oil. This material was purified by column chromatography (silica gel eluting with 40/60 ethyl acetate/hexanes) to provide 64.5 g of tert-butyl 4-(2-chloro-5,6-dimethyl-3-nitropyridin-4-yl)butylcarbamate as a bright orange oil which solidified on standing.

Part C

A solution of phenol (18.50 g, 196 mmol) in diglyme (50 mL) was slowly added dropwise to a chilled (0° C.) suspension of sodium hydride (8.28 g of 60% in mineral oil, 207 mmol) in diglyme (50 mL). After 1 hr gas evolution ceased. A solution of tert-butyl 4-(2-chloro-5,6-dimethyl-3-nitropyridin-4-yl)butylcarbamate (68.95 g, 185 mmol) in diglyme (200 mL) was slowly added dropwise to the reaction mixture. After the addition was complete the reaction mixture was heated at reflux for 4 hrs. The reaction mixture was concentrated under reduced pressure to provide a black oil. The oil was dissolved in ethyl acetate and then extracted with 1N sodium hydroxide to remove excess phenol. The organic layer was dried over magnesium sulfate and then concentrated under reduced pressure. The residue was purified by chromatography (silica gel eluting with 30/70 ethyl acetate/hexanes) to provide 40.67 g of tert-butyl 4-[(2,3-dimethyl-5-nitro-6-phenoxypyridin-4-yl)amino]butylcarbamate as an orange oil.

Part D

Tert-butyl 4-[(2,3-dimethyl-5-nitro-6-phenoxypyridin-4-yl)amino]butylcarbamate (9.17 g, 21.3 mmol), toluene (50 mL), isopropanol (5 mL) and 5% platinum on carbon (7.0 g) were combined and maintained under hydrogen pressure (50 psi, 3.5 Kg/cm$^2$) overnight on a Parr apparatus. The catalyst was removed by filtration and the filtrate was concentrated under reduced pressure. The resulting brown oil was dried under high vacuum to provide 7.47 g of tert-butyl 4-[(3-amino-5,6-dimethyl-2-phenoxypyridin-4-yl)amino]butylcarbamate.

Part E

A mixture of the material from Part D, triethyl orthoacetate (3.59 mL, 19.58 mmol), anhydrous toluene (75 mL) and pyridine hydrochloride (0.75 g) was heated at reflux for 1 hour and then concentrated under reduced pressure to provide a brown oil. The oil was dissolved in ethyl acetate and then washed with water (×2), washed with brine, dried over magnesium sulfate and then concentrated under reduced pressure to provide 6.74 g of tert-butyl 4-(2,6,7-trimethyl-4-phenoxy-1H-imidazo[4,5-c]pyridin-1-yl)butylcarbamate as a brown oil.

Part F

A solution of tert-butyl 4-(2,6,7-trimethyl-4-phenoxy-1H-imidazo[4,5-c]pyridin-1-yl)butylcarbamate (6.70 g, 15.8 mmol) in dichloromethane (50 mL) was slowly added to a chilled (0° C.) mixture of trifluoroacetic acid (60 mL) and dichloromethane (100 mL). The reaction mixture was allowed to warm to ambient temperature and then left overnight. The reaction mixture was concentrated under reduced pressure to provide a brown oil. The oil was dissolved in dichloromethane and the solution was made basic (pH 14) with 5% aqueous sodium hydroxide. The layers were separated and the aqueous layer was extracted with dichloromethane. The organic layers were combined, dried over magnesium sulfate and then concentrated under reduced pressure to provide 4.50 g of 4-(2,6,7-trimethyl-4-phenoxy-1H-imidazo[4,5-c]pyridin-1-yl)butylamine as a brown oil.

Part G

A mixture of the material from Part F, triethylamine (2.0 mL, 14.6 mmol) and anhydrous acetonitrile (450 mL) was heated until a homogeneous solution was obtained. Methanesulfonic anhydride (2.54 g, 14.6 mmol) was slowly added to the reaction mixture. The reaction was judged to be complete in 10 minutes. The reaction mixture was concentrated under reduced pressure to provide a brown oil. The oil was dissolved in dichloromethane and was washed with 5% aqueous sodium hydroxide. The aqueous layer was separated and then extracted with dichloromethane. The organic layers were combined, dried over magnesium sulfate and then concentrated under reduced pressure to provide a brown solid. This material was purified by column chromatography (silica gel eluting with 95/5 dichloromethane/methanol) to provide 4.49 g of N-[4-(2,6,7-trimethyl-4-phenoxy-1H-imidazo[4,5-c]pyridin-1-yl)butyl]methanesulfonamide as a light brown solid.

Part H

N-[4-(2,6,7-trimethyl-4-phenoxy-1H-imidazo[4,5-c]pyridin-1-yl)butyl]methanesulfonamide (4.20 g, 10.4 mmol) and ammonium acetate (42 g) were combined and then heated in a sealed tube at 150° C. for 36 hrs. The reaction mixture was allowed to cool and then it was dissolved in chloroform. The solution was extracted with 10% aqueous sodium hydroxide solution. The aqueous layer was separated and then extracted multiple times with chloroform. The organic layers were combined, dried over magnesium sulfate and then concentrated under reduced pressure to provide a yellow oil. The oil was dissolved in methanol and combined with 1M hydrochloric acid in diethyl ether (10.4 mL). The resulting white precipitate was isolated by filtration and dried. The solid was dissolved in water and the solution was adjusted to pH 10 with solid sodium carbonate. The resulting white precipitate was isolated by filtration, washed with diethyl ether and then dried in a vacuum oven at 80° C. to provide 2.00 g of N-[4-(4-amino-2,6,7-trimethyl-1H-imidazo[4,5-c]pyridin-1-yl)butyl]methanesulfonamide, m.p. 228–230° C.

Analysis: Calculated for $C_{14}H_{23}N_5O_2S$: % C, 51.67; % H, 7.12; % N, 21.52. Found: % C, 51.48; % H, 6.95; % N, 21.51.

EXAMPLE 8

N-{4-[4-amino-2-(ethoxymethyl)-6,7-dimethyl-1H-imidazo[4,5-c]pyridin-1-yl]butyl}methanesulfonamide

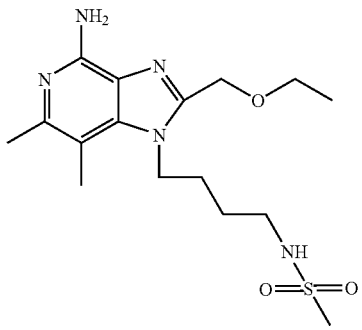

Part A

Triethylamine (3.3 mL, 23.7 mmol) was added to a chilled (0° C.) mixture of tert-butyl 4-[(3-amino-5,6-dimethyl-2-phenoxypyridin-4-yl)amino]butylcarbamate (8.60 g, 21.5 mmol) and anhydrous dichloromethane (200 mL). Ethoxyacetyl chloride (2.76 g, 22.5 mmol) was added. After one hour the reaction mixture was allowed to warm to ambient temperature and stirred for 2 hours. The reaction mixture was concentrated under reduced pressure to provide tert-butyl 4-({3-[(ethoxyacetyl)amino]-5,6-dimethyl-2-phenoxypyridin-4-yl}amino)butylcarbamate as a brown oil. The oil was combined with pyridine (130 mL) and heated at reflux overnight. The reaction mixture was concentrated under reduced pressure to provide a brown oil. The oil was dissolved in dichloromethane and was washed with water. The organic layer was dried over magnesium sulfate and then concentrated under reduced pressure. The residue was dissolved in diethyl ether and then concentrated under reduced pressure to provide 8.21 g of tert-butyl 4-[2-(ethoxymethyl)-6,7-dimethyl-4-phenoxy-1H-imidazo[4,5-c]pyridin-1-yl]butylcarbamate.

Part B

Using the method of Part F of Example 7, the material from Part A was hydrolyzed to provide 5.76 g of 4-[2-(ethoxymethyl)-6,7-dimethyl-4-phenoxy-1H-imidazo[4,5-c]pyridin-1-yl]butan-1-amine as a brown oil.

Part C

Using the method of Part G of Example 7, 4-[2-(ethoxymethyl)-6,7-dimethyl-4-phenoxy-1H-imidazo[4,5-c]pyridin-1-yl]butan-1-amine (5.52 g, 15.0 mmol) was reacted with methanesulfonic anhydride (2.74 g, 15.7 mmol) to provide 6.26 g of N-{4-[2-(ethoxymethyl)-6,7-dimethyl-4-phenoxy-1H-imidazo[4,5-c]pyridin-1-yl]butyl}methanesulfonamide as a brown solid.

Part D

Using the general method of Part H of Example 7, N-{4-[2-(ethoxymethyl)-6,7-dimethyl-4-phenoxy-1H-imidazo[4,5-c]pyridin-1-yl]butyl}methanesulfonamide (5.86 g, 13.1 mmol) was aminated to provide 1.58 g of N-{4-[4-amino-2-(ethoxymethyl)-6,7-dimethyl-1H-imidazo[4,5-c]pyridin-1-yl]butyl}methanesulfonamide as a white solid, m.p. 165–167° C.

Analysis: Calculated for $C_{16}H_{27}N_5O_3S$: % C, 52.01; % H, 7.37; % N, 18.95. Found: % C, 51.83; % H, 7.39; % N, 18.88.

EXAMPLE 9

N-[4-(4-Amino-2-butyl-6,7-dimethyl-1H-imidazo[4,5-c]pyridin-1-yl)butyl]-4-[[2-(dimethylamino)ethoxy](phenyl)methyl]benzamide

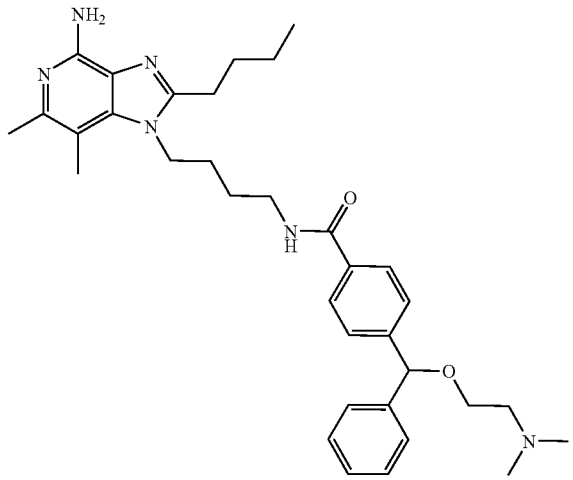

Part A

Under a nitrogen atmosphere, 4-(2-butyl-6,7-dimethyl-4-phenoxy-1H-imidazo[4,5-c]pyridin-1-yl)butan-1-amine (122 mg, 0.33 mmol) was dissolved in dichloromethane and triethylamine (0.093 mL, 0.67 mmol). The solution was cooled in an ice-water bath and 4-[[2-(dimethylamino)ethoxy](phenyl)methyl]benzoyl chloride (106 mg, 0.33 mmol) was dissolved/slurried in dichloromethane and added dropwise. The ice bath was removed and the reaction was stirred for an additional 16 hours. The reaction was quenched with 10% aqueous sodium carbonate. The phases were separated and the aqueous fraction was extracted with dichloromethane. The organic fractions were combined, washed with water followed by brine, dried ($Na_2SO_4$), decanted and evaporated to yield a yellow oil. Purification by flash column chromatography (silica gel, 92:8 dichloromethane/methanol gradient to 95:5 dichloromethane/methanol) provided 101 mg of N-[4-(2-butyl-6,7-dimethyl-4-phenoxy-1H-imidazo[4,5-c]pyridin-1-yl)butyl]-4-[[2-(dimethylamino)ethoxy](phenyl)methyl]benzamide as a pale yellow solid. The product was determined to be 97+% pure by HPLC.

MS(CI): 648 (M+H).

Part B

N-[4-(2-Butyl-6,7-dimethyl-4-phenoxy-1H-imidazo[4,5-c]pyridin-1-yl)butyl]-4-[[2-(dimethylamino)ethoxy](phenyl)methyl]benzamide (101 mg, 0.16 mmol) and ammonium acetate (1.1 g) were placed into a pressure tube along with a stir bar. The tube was sealed and heated at 150° C. for 16 hours. The reaction was cooled to room temperature and diluted with water. The resulting cloudy aqueous mixture was made basic with 10% aqueous sodium hydroxide and extracted with chloroform (3×25 mL). The combined organic fractions were washed with water followed by brine, dried ($Na_2SO_4$), decanted and evaporated to provide a yellow oil. Purification by flash column chromatography (silica gel, 95:5 dichloromethane/methanol gradient to 9:1 dichloromethane/methanol and finally 94:5:1 dichloromethane/methanol/triethylamine) provided 14 mg of N-[4-(4-amino-2-butyl-6,7-dimethyl-1H-imidazo[4,5-c]pyridin-1-yl)butyl]-4-[[2-(dimethylamino)ethoxy](phenyl)methyl]benzamide as a yellow oil.

$^1$H-NMR (500 MHz, DMSO-$d_6$) δ 8.41 (t, J=5.5 Hz, 1H), 7.76 (d, J=8.3 Hz, 2H); 7.43 (d, J=8.3, 2H), 7.37–7.31 (m, 4H), 7.26–7.22 (m, 1H), 5.84 (bs, 2H), 5.52 (s, 1H), 4.22 (t, J=7.7 Hz, 2H), 3.49 (t, J=5.8 Hz, 2H), 3.29 (dd, J=6.4, 12.4 Hz, 2H), 2.76 (t, J=7.7 Hz, 2H), 2.58 (t, J=5.7 Hz, 2H), 2.32 (s, 3H), 2.27 (s, 3H), 2.22 (s, 6H), 1.73–1.65 (m, 4H), 1.61–1.55 (m, 2H), 1.35 (sextet, J=7.4 Hz, 2H), 0.86 (t, J=7.4 Hz, 3H); $^{13}$C-NMR (125 MHz, DMSO-$d_6$) δ 165.9, 153.0, 148.1, 145.4, 142.0, 138.6, 133.5, 128.23, 127.4, 127.3, 127.1, 126.4, 126.1, 124.5, 103.0, 82.0, 66.3, 58.0, 45.2, 43.6, 38.4, 29.3, 28.8, 26.1, 26.0, 21.7, 21.0, 13.6, 12.2. HRMS (CI) m/e 571.3763 (M+H), (571.3761 calcd for $C_{34}H_{47}N_6O_2$, M+H).

EXAMPLE 10

1-(4-aminobutyl)-2-(ethoxymethyl)-6-methyl-1H-imidazo[4,5-c]pyridin-4-amine

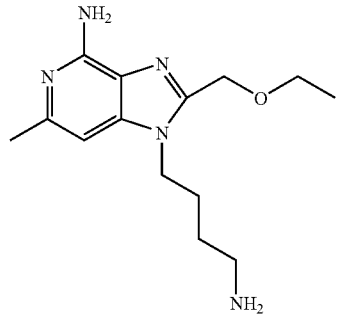

Part A

A mixture of 6-methyl-3-nitropyridine-2,4-diol (50 g, 0.29 mol) and phosphorus oxychloride (500 mL) was heated at 90° C. overnight. The excess phosphorus oxychloride was removed under reduced pressure. The resulting black oil was poured into water (1.8 L) and ice. This mixture was extracted with chloroform (×8, 3 L total) and filtered to remove black particulates and break up an emulsion. The combined organics were washed with 10% sodium carbonate (×2) and brine, dried and then concentrated under reduced pressure to provide 52 g of an amber oil. This oil was recrystallized from heptane (115 mL) to provide 43.5 g of 2,4-dichloro-6-methyl-3-nitropyridine as large amber crystals.

Part B

A solution of tert-butyl 4-aminobutylcarbamate (32.12 g, 170.6 mmol) in N,N-dimethylformamide (200 mL) was added over a period of 90 minutes to a solution of 2,4-dichloro-6-methyl-3-nitropyridine (35.09 g, 169.5 mmol) in N,N-dimethylformamide (500 mL). The reaction mixture was stirred at ambient temperature overnight. The solvent was removed by vacuum distillation using a 24/40 short path distillation head and warm water. The residue was dissolved in ethyl acetate (700 mL), washed with water (3×100 mL), dried over magnesium sulfate and then concentrated under reduced pressure. The crude product was purified by column chromatography (50×450 mm silica gel eluting with 1:1 hexane:ethyl acetate) to provide 59.90 g of tert-butyl 4-[(2-chloro-6-methyl-3-nitropyridin-4-yl)amino]butylcarbamate.

Part C

Phenol (9.45 g, 100 mmol) was added over a period of 10 minutes to a chilled (0° C.) suspension of sodium hydride (4.24 g of 60%, 106 mmol) in anhydrous tetrahydrofuran (100 mL). The reaction mixture was allowed to stir at 0° C. for 30 minutes. A solution of tert-butyl 4-[(2-chloro-6-methyl-3-nitropyridin-4-yl)amino]butylcarbamate (33.92 g, 94.5 mmol) in anhydrous tetrahydrofuran (250 mL) was added over a period of 50 minutes while maintaining the reaction mixture at 0° C. The reaction mixture was allowed to warm to ambient temperature and stirred overnight before being concentrated under reduced pressure. The residue was dissolved in ethyl acetate (500 mL), washed with 1N sodium hydroxide (300 mL), dried over magnesium sulfate and then concentrated to dryness. The crude product was purified by column chromatography (400 g silica gel eluting with 7:3 hexanes:ethyl acetate to provide 25.4 g of tert-butyl 4-[(6-methyl-3-nitro-2-phenoxypyridin-4-yl)amino]butylcarbamate.

Part D

A solution of the material from Part C in a mixture of toluene (300 mL) and isopropanol (33 mL) was combined with catalyst (16.68 g of 5% Pt/C) and placed under hydrogen pressure (30 psi, 2.1 Kg/cm$^2$; recharging once) on a Parr apparatus for 5 hours. The reaction mixture was filtered to remove the catalyst and then concentrated under reduced pressure to provide 23.4 g of tert-butyl 4-[(3-amino-6-methyl-2-phenoxypyridin-4-yl)amino]butylcarbamate as a dark oil.

Part E

The material from Part D was dissolved in dichloromethane (500 mL) and then cooled under a nitrogen atmosphere to 0° C. A solution of ethoxyacetyl chloride (7.9 g, 63.5 mmol) in dichloromethane (200 mL) was added over a period of 40 minutes while maintaining the reaction mixture at 0° C. The reaction mixture was allowed to warm to ambient temperature and was stirred overnight. The reaction mixture was washed with water (2×100 mL) and brine (100 mL), dried over magnesium sulfate and then concentrated under reduced pressure to provide 26.4 g of tert-butyl 4-({3-[(ethoxyacetyl)amino]-6-methyl-2-phenoxypyridin-4-yl}amino)butylcarbamate.

Part F

The material from Part E was combined with pyridine (250 mL) and pyridine hydrochloride (20.85 g, 180 mmol) and heated at reflux under a nitrogen atmosphere overnight. The bulk of the pyridine was removed by vacuum distillation. The residue was partitioned between ethyl acetate (600 mL) and water (300 mL). The layers were separated. The organic layer was washed with water (2×300 mL), dried over magnesium sulfate and then concentrated under reduced pressure to provide 8.17 g of tert-butyl 4-[2-(ethoxymethyl)-6-methyl-4-phenoxy-1H-imidazo[4,5-c]pyridin-1-yl]butylcarbamate as a dark oil. The pH of the aqueous layer was adjusted to 11 with 15% sodium hydroxide and then it was extracted with ethyl acetate (5×250 mL). The extracts were combined, dried over magnesium sulfate and then concentrated under reduced pressure to provide 9.46 g of 4-[2-(ethoxymethyl)-6-methyl-4-phenoxy-1H-imidazo[4,5-c]pyridin-1-yl]butan-1-amine.

Part G

Benzyl chloroformate (2.2 mL) was added over a period of 2 minutes to a solution of 4-[2-(ethoxymethyl)-6-methyl-4-phenoxy-1H-imidazo[4,5-c]pyridin-1-yl]butan-1-amine (4.96 g, 14 mmol) and triethylamine (2.6 mL) in chloroform (100 mL). The reaction mixture was allowed to stir at ambient temperature for 2.5 hours; it was washed with 1N sodium hydroxide (50 mL), dried over magnesium sulfate, and concentrated under reduced pressure. The crude product was purified by column chromatography (208 g silica gel eluting with 2% methanol in chloroform) to provide two fractions (2.2 g and 3.12 g) of benzyl 4-[2-ethoxymethyl)-6-methyl-4-phenoxy-1H-imidazo[4,5-c]pyridin-1-yl)butylcarbamate.

Part H

The first fraction (2.2 g) from Part G and ammonium acetate (20.3 g) were combined in a pressure vessel (75 mL). The vessel was sealed and then heated at 150° C. for 21.5 hours. The reaction mixture was diluted with chloroform (200 mL) and washed with 10% sodium hydroxide (3×70 mL). The aqueous layer was extracted with chloroform (6×100 mL). The combined organic layers were dried over magnesium sulfate and then concentrated under reduced pressure. Analysis by LCMS indicated that the crude product was a 50/50 mixture of N-{4-[4-amino-2-(ethoxymethyl)-6-methyl-1H-imidazo[4,5-c]pyridin-1-yl]butyl}acetamide/benzyl 4-[4-amino-2-(ethoxymethyl)-6-methyl-1H-imidazo[4,5-c]pyridin-1-yl]butylcarbamate.

Part I

A solution of the material from Part H in ethanol (28 mL) was combined with concentrated hydrochloric acid (18.3 mL) in a pressure vessel (150 mL). The vessel was sealed and then heated at 90° C. for 21 hours. The reaction mixture was concentrated under reduced pressure. The residue was dissolved in water (100 mL) and then washed with chloroform (3×50 mL). The aqueous layer was adjusted to pH>11, saturated with sodium chloride and then extracted with chloroform (8×100 mL). The extracts were combined, dried over magnesium sulfate and then concentrated under reduced pressure. The crude product was combined with crude product from another run and then was purified by column chromatography (25 g of silica gel eluting sequentially with 2% methanol in dichloromethane with 0.5% triethylamine (1 L); 4% methanol in chloroform (800 mL); and 6% methanol in chloroform (800 mL) to provide 1.3 g of 1-(4-aminobutyl)-2-ethoxymethyl-6-methyl-1H-imidazo[4,5-c]pyridin-4-amine as a solid, m.p. 108–111° C.

Analysis: Calculated for $C_{14}H_{23}N_5O \cdot 0.05$ HCl: % C, 60.23; % H, 8.32; % N, 25.08. Found: % C, 59.92; % H, 8.26; % N, 24.81. $^1$H NMR (300 MHz, CDCl$_3$) δ 6.53 (s, 1 H), 5.12 (s, 2 H), 4.72 (s, 2 H), 4.15 (t, J=7.5 Hz, 2 H), 3.57 (quartet, J=6.8 Hz, 2 H), 2.74 (t, J=6.9 Hz, 2 H), 2.48 (s, 3 H), 1.86 (quintet, J=7.7 Hz, 2 H), 1.51 (m, 4 H), 1.22 (t, J=6.9 Hz, 3 H); MS(CI) m/e 278 (M+H)

EXAMPLE 11

N-{4-[4-amino-2-(ethoxymethyl)-6-methyl-1H-imidazo[4,5-c]pyridin-1-yl]butyl}-2-methylpropanamide

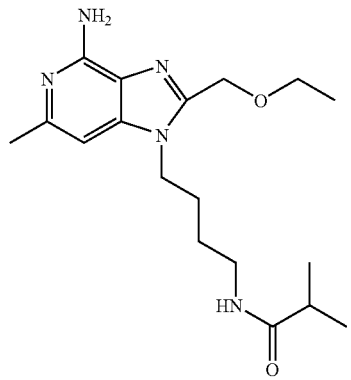

Isobutyryl chloride (181 μL, 1.73 mmol) was added to a solution of 1-(4-aminobutyl)-2-ethoxymethyl-6-methyl-1H-imidazo[4,5-c]pyridin-4-amine (0.435 g, 1.57 mmol), triethylamine (280 μL, 2.04 mmol) and chloroform (8 mL). The reaction mixture was allowed to stir at ambient temperature for 4 hours then it was diluted with chloroform (20 mL) and washed with saturated sodium bicarbonate solution (10 mL). The organic layer was dried over magnesium sulfate and then concentrated under reduced pressure. The residue was purified by column chromatography (30 g of silica gel eluting with 1 L of 2% methanol in chloroform containing 0.5% triethylamine) to provide 0.225 g of N-{4-[4-amino-2-(ethoxymethyl)-6-methyl-1H-imidazo[4,5-c]pyridin-1-yl]butyl}-2-methylpropanamide as a white powder, m.p. 170.5–172.5° C.

Analysis: Calculated for $C_{18}H_{29}N_5O_2$: % C, 62.22; % H, 8.41; % N, 9.21. Found: % C, 62.00; % H, 8.46; % N, 20.13.
$^1$H NMR (300 MHz, CDCl$_3$) δ 6.55 (s, 1 H), 5.45 (bs, 1 H), 5.17 (bs, 2 H), 4.70 (s, 2 H), 4.16 (t, J=7.5 Hz, 2H), 3.57 (quartet, J=6.8 Hz, 2H), 3.29 (quartet, J=6.6 Hz, 2 H), 2.48 (s, 3 H), 2.31 (quintet, J=6.9 Hz, 1 H), 1.85 (quintet, J=7.5 Hz, 2 H), 1.56 (quintet, J=7.3 Hz, 2 H), 1.22 (t, J=7.2 Hz, 3 H), 1.15 (d, J=6.7 Hz, 6H); MS(CI) m/e 348 (M+H)

EXAMPLE 12

N-[4-(4-amino-6,7-dimethyl-1H-imidazo[4,5-c]pyridin-1-yl)butyl]acetamide

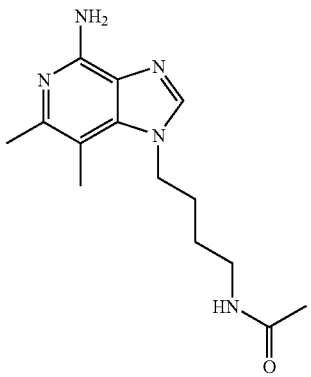

Part A

A suspension of 5,6-dimethyl-3-nitropyridine-2,4-diol (14.87 g) in phosphorous oxychloride (150 mL) was heated at reflux for 2 hours. Excess phosphorous oxychloride was removed by distillation. The residue was dissolved in water, neutralized with ammonium hydroxide, and extracted twice with ethyl acetate. The organics were combined, washed with brine, dried over sodium sulfate and then concentrated under reduced pressure. The residue was slurried with boiling hexane and then filtered while hot. The filtrate was chilled. The resulting precipitate was isolated by filtration and air dried to provide 6.8 g of 2,4-dichloro-5,6-dimethyl-3-nitropyridine as a white powder.

Part B

A solution of tert-butyl 4-aminobutylcarbamate (8.52 g, 45.24 mmol) in N,N-dimethylformamide was added to a solution of 2,4-dichloro-5,6-dimethyl-3-nitropyridine (10.00 g, 45.24 mmol) and triethylamine (12.6 mL, 90.5 mmol) in N,N-dimethylformamide (320 mL). The reaction mixture was stirred overnight and then concentrated under reduced pressure. The residue was partitioned between water and ethyl acetate. The layers were separated and the aqueous layer was extracted with ethyl acetate. The organics were combined, washed with brine and then concentrated under reduced pressure to provide a brown oily residue. This material was purified by flash chromatography (400 mL silica gel, eluting initially with 10% ethyl acetate in hexane and then increasing the gradient to 15% and then to 25%) to provide 8.1 g of tert-butyl 4-[(2-chloro-5,6-dimethyl-3-nitropyridin-4-yl)amino]butylcarbamate as a yellow solid.

Part C

Phenol (2.164 g, 23.00 mmol) was added as a solid over a period of 10 minutes to a suspension of sodium hydride (0.972 g, 24.3 mmol) in diglyme (24 mL). The reaction mixture was allowed to stir for 30 minutes then the material from Part B was added as a solid. The reaction mixture was stirred at 80° C. for 2.5 days and then allowed to cool to ambient temperature overnight. The diglyme was removed under reduced pressure to provide an oily residue. The residue was combined with cold water and allowed to stir overnight. Ethyl acetate was added and the layers were separated. The aqueous layer was extracted with ethyl acetate. The organics were combined, washed with water and brine, dried over sodium sulfate and then concentrated under reduced pressure to provide a black oil. This material was purified by flash chromatography (400 mL silica gel eluting with 25% ethyl acetate in hexanes) to provide 7.1 g of tert-butyl 4-[(2,3-dimethyl-5-nitro-6-phenoxypyridin-4-yl)amino]butylcarbamate as an orange oil which later solidified.

Part D

A solution of tert-butyl 4-[(2,3-dimethyl-5-nitro-6-phenoxypyridin-4-yl)amino]butylcarbamate (7.32 g, 17.00 mmol) in a mixture of toluene (150 mL) and isopropanol (10 mL) was combined with a slurry of 10% palladium on carbon in toluene. The mixture was place under hydrogen pressure on a Parr apparatus for 24 hours. Additional catalyst was added at 1.5 hours (2.2 g) and 3 hours (3 g). The reaction mixture was filtered through a layer of Celite® filter agent to remove the catalyst. The layer of filter agent was washed with ethanol (1 L), ethanol/methanol (1 L), and methanol (1 L). The filtrate was concentrated under reduced pressure. The residue was combined with dichloromethane and heptane and then concentrated under reduced pressure to provide 6.17 g of tert-butyl 4-[(3-amino-5,6-dimethyl-2-phenoxypyridin-4-yl)amino]butylcarbamate as a sludgy brown yellow oil.

Part E

Diethoxymethyl acetate (2.76 mL, 16.93 mmol) and pyridine hydrochloride (0.037 g, 0.323 mmol) were added to a solution of the material from Part D in toluene (72 mL). The reaction mixture was heated at reflux for 2 hours and then allowed to cool to ambient temperature overnight. The reaction mixture was concentrated under reduced pressure and then the residue was twice combined with toluene and concentrated. The resulting oil was dissolved in chloroform; washed with saturated sodium bicarbonate, water and brine; dried over magnesium sulfate and then concentrated under reduced pressure to provide 5.37 g of tert-butyl 4-(6,7-dimethyl-4-phenoxy-1H-imidazo[4,5-c]pyridin-1-yl)butylcarbamate as a very thick brown oil/solid.

Part F

The material from Part E was combined with ammonium acetate (47 g) in a tube. The tube was sealed and heated at 150° C. for 20 hours. The reaction mixture was poured into water and adjusted to pH 10 with 10% sodium hydroxide. The basic solution was extracted with chloroform (×9). The basic layer was treated with solid sodium chloride and then extracted with chloroform. The organics were combined, dried over sodium sulfate and then concentrated under reduced pressure to provide a yellowish solid. The solid was dissolved in a mixture of chloroform and methanol and then combined with 50 mL of 1N hydrochloric acid in diethyl ether. The solvents were removed and the resulting oil was dissolved in water. This solution was extracted with dichloromethane (×3), made basic (pH 10) with 50% sodium hydroxide, and then extracted with chloroform (×3). Sodium chloride was added to the aqueous solution and it was extracted with chloroform (×3). The organics were combined, dried over sodium sulfate and concentrated under reduced pressure to provide a yellow solid. This solid was recrystallized from ethanol to provide 2.62 g of a solid. A portion (500 mg) was dissolved in methanol, concentrated under reduced pressure and then dried in a vacuum oven at 70° C. over the weekend to provide 0.46 g of N-[4-(4-amino-6,7-dimethyl-1H-imidazo[4,5-c]pyridin-1-yl)butyl]acetamide as a solid, m.p. 217–219° C.

Analysis: Calculated for $C_{14}H_{21}N_5O$: % C, 61.07; % H, 7.69; % N, 25.43. Found: % C, 60.87; % H, 7.75; % N, 25.43. $^1$H NMR (300 MHz, DMSO-$d_6$) δ 7.90 (s, 1 H), 7.82 (t, J=5.2 Hz, 1H), 5.75 (s, 2 H), 4.29 (t, J=7.1 Hz, 2 H), 3.04 (q, J=6.8 Hz, 2 H), 2.36 (s, 3 H), 2.30 (s, 3 H), 1.77 (s, 3 H), 1.70 (quintet, J=7.5 Hz, 2 H), 1.35 (quintet, J=7.1 Hz, 2 H); $^{13}$C NMR (75 Hz, DMSO-$d_6$) δ 169.0, 149.4, 145.9, 142.8, 137.5, 126.4, 102.9, 45.3, 37.9, 29.0, 26.2, 22.6, 21.7, 12.6; MS (CI) m/e 276.1825 (276.1824 calcd for $C_{14}H_{21}N_5O$, M+H).

EXAMPLE 13

1-(4-aminobutyl)-6,7-dimethyl-1H-imidazo[4,5-c]pyridin-4-amine

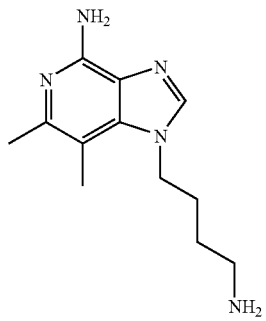

A solution of N-[4-(4-amino-6,7-dimethyl-1H-imidazo[4,5-c]pyridin-1-yl)butyl]acetamide (~2.1 g) in 6 N hydrochloric acid (30 mL) was sealed in a flask and then heated at 100° C. for about 30 hours. The reaction mixture was allowed to cool to ambient temperature and then filtered to remove any particulates. The filtrate was made basic (pH 14) with 25% sodium hydroxide and then extracted with chloroform (×2). The aqueous layer was combined with sodium chloride (20 g) and then extracted with chloroform (×3). The organics were combined, washed with brine, dried over sodium sulfate and then concentrated under reduced pressure to provide 1.44 g of 1-(4-aminobutyl)-6,7-dimethyl-1H-imidazo[4,5-c]pyridin-4-amine.

EXAMPLE 14

2-(ethoxymethyl)-6,7-dimethyl-1-(2-piperidin-4-ylethyl)-1H-imidazo[4,5-c]pyridin-4-amine

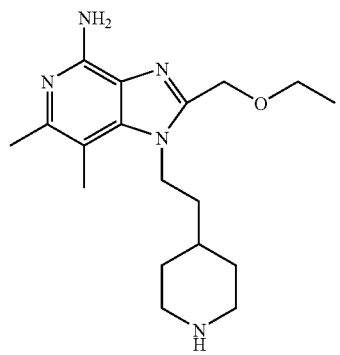

Part A

A solution of 4-(2-aminoethyl)-1-benzylpiperidine (9.88 g, 45.2 mmol) in N,N-dimethylformamide was added dropwise to a solution of 2,4-dichloro-5,6-dimethyl-3-nitropyridine (10.00 g, 45.2 mmol) and triethylamine (12.6 mL, 90.5 mmol) in N,N-dimethylformamide (320 mL). The reaction mixture was allowed to stir at ambient temperature for about 20 hours and then it was concentrated under reduced pressure. The residue was partitioned between ethyl acetate and water. The layers were separated and the aqueous layer was extracted with ethyl acetate. The organics were combined, washed with brine, dried over sodium sulfate and then concentrated under reduced pressure to provide an orange oil. The oil was purified by flash chromatography (400 mL silica gel eluting initially with 10% ethyl acetate in hexane, then with 15% ethyl acetate in hexane and finally with 40% ethyl acetate in hexane) to provide 11.00 g of N-[2-(1-benzylpiperidin-4-yl)ethyl]-2-chloro-5,6-dimethyl-3-nitropyridin-4-amine.

Part B

Sodium hydride (1.196 g of 60%, 29.9 mmol) was added to a solution of phenol (2.81 g, 29.9 mol) in diglyme (40 mL). The mixture was stirred for 15 minutes after the cessation of gas evolution. A solution of N-[2-(1-benzylpiperidin-4-yl)ethyl]-2-chloro-5,6-dimethyl-3-nitropyridin-4-amine (10.9 g, 27.2 mmol) in hot diglyme was added to the phenoxide mixture. The reaction mixture was heated at reflux for 1.5 hours, cooled to ambient temperature, and then concentrated to remove the diglyme (60° C. bath, 21 Pa). The residue was purified by column chromatography eluting first with 1% methanol in dichloromethane to remove residual diglyme and then with 5% methanol in dichloromethane to elute product. The fractions were concentrated to provide 5.91 g of N-[2-(1-benzylpiperidin-4-yl)ethyl]-2,3-dimethyl-5-nitro-6-phenoxypyridin-4-amine as an orange-brown oil which solidified on standing.

Part C

Sodium borohydride (0.727 g, 19.2 mmol) was added in portions over a period of 20 minutes to a solution of nickel(II)chloride hexahydrate (1.52 g, 6.40 mmol) in methanol. A solution of the material from Part B in methanol was added dropwise over a period of 15 minutes. More sodium borohydride (50 mg) was added. The reaction mixture was filtered through a layer of filter agent and the filter cake was washed with methanol. The filtrate was concentrated under reduced pressure. The residue was purified by chromatography (plug of silica gel eluting with 2% methanol in dichloromethane) to provide 4.6 g of $N^4$-[2-(1-benzylpiperidin-4-yl)ethyl]-5,6-dimethyl-2-phenoxypyridine-3,4-diamine as an orange-brown oil which solidified on standing.

Part D

Ethoxyacetyl chloride (1.31 g, 10.7 mmol) was added dropwise to a solution of the material from Part C and triethylamine (1.64 mL, 13 mmol) in dichloromethane (60 mL). The reaction was stirred for about 20 hours and then concentrated under reduced pressure to provide crude N-(4-{[2-(1-benzylpiperidin-4-yl)ethyl]amino}-5,6-dimethyl-2-phenoxypyridin-3-yl)-2-ethoxyacetamide. The acetamide was dissolved in pyridine (60 mL), pyridine hydrochloride (1.17 g) was added and the reaction mixture was heated at reflux for 4 hours. The reaction mixture was allowed to cool to ambient temperature and then the pyridine was removed under reduced pressure. The residue was diluted with 5% sodium carbonate (100 mL) and water (50 mL) then partitioned into dichloromethane (300 mL). The organic layer was washed with water and brine, dried over magnesium sulfate and then concentrated under reduced pressure. The residue was purified by column chromatography eluting with 2% methanol in dichloromethane to provide 5.1 g of 1-[2-(1-benzylpiperidin-4-yl)ethyl]-2-(ethoxymethyl)-6,7-dimethyl-4-phenoxy-1H-imidazo[4,5-c]pyridine as an orange-red solid.

Part E

The material from Part D and ammonium acetate (51 g) were combined in a pressure flask (350 mL). The flask was sealed and then heated at 150° C. for 24 hours followed by heating at 170° C. overnight. The reaction mixture was cooled and then poured into water. The resulting solution was made basic with ammonium hydroxide and then extracted with chloroform (×2). The combined organics were washed with brine, dried over magnesium sulfate and then concentrated under reduced pressure. The residue was dissolved in isopropanol (50 mL). Ethanesulfonic acid (21 mmol) was added dropwise and the mixture was heated at reflux for 30 minutes. The reaction was allowed to cool to ambient temperature overnight and then it was concentrated under reduced pressure. The resulting oily residue was dissolved in water (200 mL), extracted with dichloromethane (×3) and then made basic (pH 14) with 10% sodium hydroxide. The aqueous layer was extracted with chloroform (×3). The combined organics were washed with brine, dried over magnesium sulfate and then concentrated to provide a brown oil which solidified. The solid was recrystallized from acetonitrile to provide 2.54 g of a tan solid. The solid was dissolved in 2% methanol in dichloromethane and loaded onto a silica gel (130 g) column. The column was eluted with 2% methanol in dichloromethane with 1% triethylamine. The fractions were concentrated to provide 2.4 g of 1-[2-(1-benzylpiperidin-4-yl)ethyl]-2-(ethoxymethyl)-6,7-dimethyl-1H-imidazo[4,5-c]pyridin-4-amine as an off-white solid.

Part F

The material from Part E was dissolved in a boiling mixture of 50/50 ethanol/methanol. The solution was allowed to cool slightly and then it was added to a Parr flask containing palladium on carbon (0.60 g) that had been wetted with ethanol. The flask was placed under hydrogen pressure for about 40 hours during which time an additional 1.7 g of catalyst was added. The reaction mixture was filtered through a layer of filter agent and the filter cake was washed with methanol. The filtrate was concentrated under reduced pressure. The residue was combined with dichloromethane and then concentrated. The resulting solid was dried under high vacuum to provide 1.5 g of 2-(ethoxymethyl)-6,7-dimethyl-1-(2-piperidin-4-ylethyl)-1H-imidazo[4,5-c]pyridin-4-amine.

EXAMPLE 15

1-[2-(1-benzylpiperidin-4-yl)ethyl]-2-(ethoxymethyl)-6,7-dimethyl-1H-imidazo[4,5-c]pyridin-4-amine

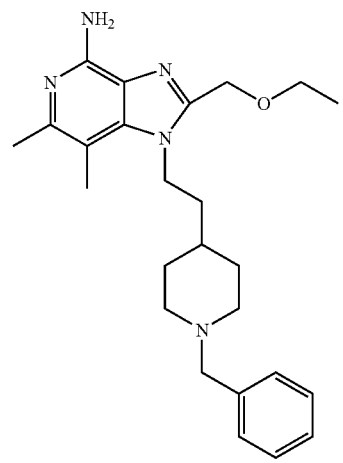

Using the method of Example 14 Part E, 1-[2-(1-benzylpiperidin-4-yl)ethyl]-2-(ethoxymethyl)-6,7-dimethyl-4-phenoxy-1H-imidazo[4,5-c]pyridine (2.7 g) was aminated. The crude product was purified by column chromatography (70 g of silica gel eluting with 2% methanol in dichloromethane containing 1% triethylamine) followed by recrystallization from acetonitrile to provide 160 mg of 1-[2-(1-benzylpiperidin-4-yl)ethyl]-2-(ethoxymethyl)-6,7-dimethyl-1H-imidazo[4,5-c]pyridin-4-amine as a crystalline solid, m.p. 165.3–167.0° C.

Analysis: Calculated for $C_{25}H_{35}N_5O$: % C, 71.23; % H, 837; % N, 16.61. Found: % C, 71.14; % H, 8.28; % N, 16.55. $^1$H NMR (300 MHz, DMSO-$d_6$) δ 7.35–7.17 (m, 5 H), 5.78 (s, 2 H), 4.62 (s, 2 H), 4.35–4.2 (m, 2 H), 3.50 (q, J=7.0 Hz, 2 H), 3.43 (s, 2 H), 2.79 (d, J=11.6 Hz, 2 H), 2.37 (s, 3 H), 2.30 (s, 3 H), 1.93 (t, J=10.8 Hz, 2 H), 1.75–1.6 (m, 4 H), 1.5–1.33 (m, 1 H), 1.32–1.2 (m, 2 H), 1.14 (t, J=7.0 Hz, 3 H); MS (CI) m/e 422.2923 (422.2920 calcd for $C_{25}H_{35}N_5O$, M+H).

EXAMPLE 16

2-(ethoxymethyl)-1-[2-(1-isobutyrylpiperidin-4-yl)ethyl]-6,7-dimethyl-1H-imidazo[4,5-c]pyridin-4-amine

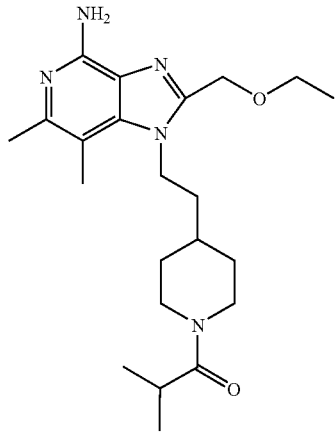

Isobutyryl chloride (96 μL, 0.917 mmol) was added drop wise to a chilled (0° C.) solution of 2-(ethoxymethyl)-6,7-dimethyl-1-(2-piperidin-4-ylethyl)-1H-imidazo[4,5-c]pyridin-4-amine (304 mg, 0.917 mmol) in dichloromethane (10 mL). The reaction mixture was allowed to stir overnight then it was diluted with chloroform and washed with 5% sodium hydroxide, water and brine. The organic layer was dried over magnesium sulfate and then concentrated under reduced pressure. The residue was recrystallized from acetonitrile to provide 185 mg of 2-(ethoxymethyl)-1-[2-(1-isobutyrylpiperidin-4-yl)ethyl]-6,7-dimethyl-1H-imidazo[4,5-c]pyridin-4-amine as a yellowish solid, m.p. 167.5–169.2° C.

Analysis: Calculated for $C_{22}H_{35}N_5O_2$: % C, 65.81; % H, 8.79; % N, 17.44. Found: % C, 65.87; % H, 8.58; % N, 17.75. $^1$H NMR (300 MHz, DMSO-$d_6$) δ 5.76 (s, 2 H), 4.64 (s, 2 H), 4.45–4.26 (m, 3 H), 4.0–3.9 (m, 1 H), 3.50 (q, J=7.0 Hz, 2 H), 3.03 (t, J=12.6 Hz, 1 H), 2.86 (quintet, J=6.7 Hz, 1 H), 2.6–2.48 (m, 1 H), 2.38 (s, 3 H), 2.31 (s, 3 H), 1.85–1.6 (m, 5 H), 1.2–0.95 (m, 2 H), 1.14 (t, J=7.0 Hz, 3 H), 0.98 (d, J=6.6 Hz, 6 H); MS (CI) m/e 402.2857 (402.2869 calcd for $C_{22}H_{35}N_5O_2$, M+H).

EXAMPLE 17

N-[3-(4-amino-2,6,7-trimethyl-1H-imidazo[4,5-c]pyridin-1-yl)propyl]acetamide

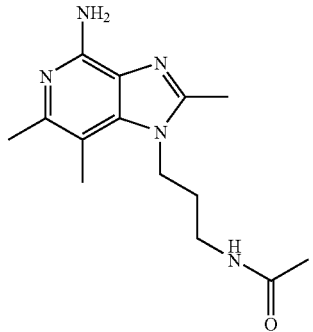

Part A

A solution of tert-butyl 3-aminopropylcarbamate (121.39 g, 697 mmol) in N,N-dimethylformamide (200 mL) was slowly added to a solution of 2,4-dichloro-5,6-dimethyl-3-nitropyridine (110 g, 498 mmol) and triethylamine (104 mL, 746 mmol) in N,N-dimethylformamide (900 mL). After stirring at ambient temperature for 20 hours the reaction mixture was heated to 55° C. At 24 hours 0.1 equivalents of the carbamate was added. The reaction mixture was allowed to cool to ambient temperature overnight and then concentrated under reduced pressure. The residue was dissolved in ethyl acetate (3 L). The solution was divided into 3 aliquots (1 L each). Each aliquot was washed with water (2×1 L). The pH of the aqueous washes was adjusted to 10 with potassium carbonate and then they were extracted with ethyl acetate. All of the ethyl acetate layers were combined, dried over sodium sulfate and then concentrated under reduced pressure to provide 181 g of crude product. This material was recrystallized from acetonitrile to provide 138 g of tert-butyl 3-[(2-chloro-5,6-dimethyl-3-nitropyridin-4-yl)amino]propylcarbamate as a yellow solid.

Part B

Sodium hydride (17.23 g of 60%) was washed with hexanes to remove the mineral oil and then combined with diglyme (50 mL). Under a nitrogen atmosphere the mixture was cooled. A solution of phenol (35.82 g, 408 mmol) in diglyme (150 mL) was added dropwise. The reaction mixture was stirred for 15 minutes after the cessation of gas evolution. The material from Part A was added. The reaction mixture was heated at 62° C. for several days, then the temperature was increased to 120° C. and the reaction was stirred overnight. The reaction mixture was allowed to cool to ambient temperature, then it was combined with water (4 L), stirred for about 4.5 hours and then allowed to stand overnight. The solids were dissolved in ethyl acetate and then filtered to remove particulates. The filtrate was concentrated under reduced pressure. The residue was dissolved in ethyl acetate (~2 L), washed with saturated potassium carbonate (3×2 L), dried over magnesium sulfate and then concentrated under reduced pressure to provide 152.3 g of tert-butyl 3-[(2,3-dimethyl-5-nitro-6-phenoxypyridin-4-yl)amino]propylcarbamate.

Part C

A mixture of 5% Pt/C (85 g) and toluene (50 mL) was added to a solution of the material from Part B in a mixture of toluene (1850 mL) and isopropanol (125 mL) in a hydrogenation flask. The flask was placed under a hydrogen atmosphere overnight. Another 22.5 g of catalyst was added and the flask was placed back on the hydrogenator. After 6 hours catalyst (40 g) and isopropanol (50 mL) were added. The flask was placed back on the hydrogenator overnight. The reaction mixture was filtered to remove the catalyst. The filtrate was concentrated under reduced pressure to provide tert-butyl 3-[(3-amino-5,6-dimethyl-2-phenoxypyridin-4-yl)amino]propylcarbamate as an oil. The oil was dissolved in pyridine (1300 mL).

Part D

A portion (650 mL) of the pyridine solution from Part C was cooled in an ice bath for 10 minutes. Acetyl chloride (12.65 mmol, 0.1779 mmol) was slowly added over a period of 5 minutes. The reaction mixture was removed from the ice bath and heated to reflux. The temperature was reduced to 110° C. and the reaction mixture was stirred overnight. The pyridine was removed under reduced pressure. The residue was slurried with heptane and then concentrated under reduced pressure. The residue was combined with ethyl acetate (1 L) and water (1 L). The pH was adjusted to 12 with 50% sodium hydroxide and the layers were separated. The organic layer was filtered to remove particulates and then concentrated under reduced pressure. The residue was purified by ethyl acetate slurry to provide 39.8 g of tert-butyl 3-(2,6,7-trimethyl-4-phenoxy-1H-imidazo[4,5-c]pyridin-1-yl)propylcarbamate as a light brown fluffy solid.

Part E

The material from Part D was combined with ammonium acetate (410 g) in a 2 L flask. A wad of paper towels was stuffed into the neck of the flask. The reaction mixture was heated with stirring at 145° C. for 20.5 hours. The reaction mixture was allowed to cool to ambient temperature, the pH was adjusted to 11 with ammonium hydroxide and the mixture was extracted with chloroform. The extract was washed with 1% sodium carbonate (7×1 L). The original aqueous phase and the first three washes were combined, filtered to remove particulates and then concentrated to a volume of about 1 L. This solution was run overnight on a continuous extraction apparatus with chloroform. The chloroform extract was concentrated under reduced pressure to provide 27.1 g of an off-white solid. This material was slurried with methyl acetate to provide about 16.5 g of N-[3-(4-amino-2,6,7-trimethyl-1H-imidazo[4,5-c]pyridin-1-yl)propyl]acetamide. A portion (0.5 g) was recrystallized from acetonitrile to provide about 0.3 g of the pure acetamide as a white solid, m.p. 181.4–182.1° C. Analysis: Calculated for $C_{14}H_{21}N_5O \cdot 0.50\ H_2O$: % C, 59.13; % H, 7.80; % N, 24.63. Found: % C, 59.08; % H, 8.00; % N, 24.73. $^1$H NMR (Bruker 300 MHz, CHCl$_3$-d) δ 5.70 (t, J=5.6 Hz, 1 H), 4.84 (s, 2 H), 4.20 (t, J=8.1 Hz, 2 H), 3.35 (q, J=6.2 Hz, 2 H), 2.52 (s, 3 H), 2.43 (s, 3 H), 2.41 (s, 3 H), 1.98 (s, 3 H), 1.91 (p, J=8.1 Hz, 2 H). MS(CI) m/e 276 (M+H).

EXAMPLE 18

1-(3-aminopropyl)-2,6,7-trimethyl-1H-imidazo[4,5-c]pyridin-4-amine

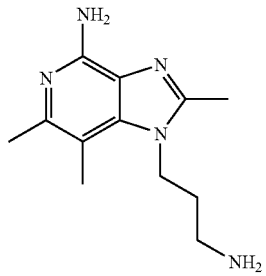

Concentrated hydrochloric acid (5 mL) was slowly added to a solution of N-[3-(4-amino-2,6,7-trimethyl-1H-imidazo[4,5-c]pyridin-1-yl)propyl]acetamide (15.94 g, 57.9 mmol) in absolute ethanol (100 mL). A precipitate formed immediately and the mixture thickened. Ethanol (50 mL) was added followed by the addition of concentrated hydrochloric acid (119.5 mL). The reaction mixture was heated at reflux for 2 days. The solvents were removed under reduced pressure. Water (250 mL) was added to the residue, solid potassium carbonate was added until the pH reached 7 at which time chloroform (250 mL) was added. Sodium carbonate addition was resumed until the pH reached 10, then 50% sodium hydroxide was added until the pH reached 14. The mixture was diluted with additional chloroform (500 mL) and then stirred at ambient temperature for 2 days. The organic layer was separated, dried with magnesium sulfate and then concentrated under reduced pressure. The residue was recrystallized from acetonitrile to provide 8.42 g of 1-(3-aminopropyl)-2,6,7-trimethyl-1H-imidazo[4,5-c]pyridin-4-amine as an off-white crystalline solid, m.p. 191.5–200° C. Analysis: Calculated for $C_{12}H_{19}N_5 \cdot 0.25\ H_2O$: % C, 60.61; % H, 8.26; % N, 29.45. Found: % C, 60.50; % H, 8.28; % N, 29.57.

$^1$H NMR (Bruker 300 MHz, CHCl$_3$-d) δ 4.88 (s, 2 H), 4.28 (t, J=7.4 Hz, 2 H), 2.80 (t, J=6.8 Hz, 2 H), 2.56 (s, 3 H), 2.43 (s, 6 H), 1.87 (p, J=7.4 Hz, 2 H), 1.12 (s, 2 H). MS(CI) m/e 234 (M+H).

EXAMPLE 19

N-[3-(4-amino-2,6,7-trimethyl-1H-imidazo[4,5-c]pyridin-1-yl)propyl]-2-methylpropanamide

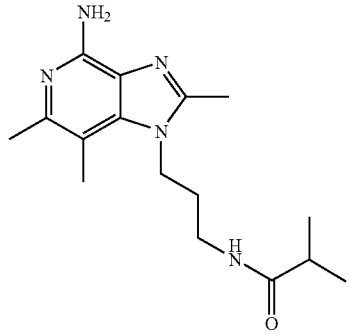

Triethylamine (0.78 mL, 5.6 mmol) was added to a solution of 1-(3-aminopropyl)-2,6,7-trimethyl-1H-imidazo[4,5-c]pyridin-4-amine (1.00 g, 4.3 mmol) in chloroform (50 mL). The solution was cooled in an ice bath and then isobutyryl chloride (0.49 mL, 4.7 mmol) was added. The reaction mixture was stirred for 15 minutes then the ice bath was removed and the reaction mixture was stirred for an additional 15 minutes. The reaction mixture was diluted with chloroform to a volume of 150 mL. Water (50 mL) was added then the pH was adjusted to 11 with solid potassium carbonate and then to pH 14 with 50% sodium hydroxide. The resulting precipitate was isolated by filtration and dried to provide 0.33 g of N-[3-(4-amino-2,6,7-trimethyl-1H-imidazo[4,5-c]pyridin-1-yl)propyl]-2-methylpropanamide as a white solid, m.p. 178.1–178.8° C.

Analysis: Calculated for $C_{16}H_{25}N_5O \cdot 1.25\ H_2O$: % C, 58.96; % H, 8.50; % N, 21.49; Found: % C, 58.68; % H, 8.35; % N, 21.65. $^1$H NMR (300 MHz, Bruker, DMSO-d$_6$) δ 7.84 (t, J=6.2 Hz, 1 H), 5.57 (s, 2 H), 4.17 (t, J=8.1 Hz, 2 H), 3.14 (q, J=6.2 Hz, 2 H), 2.44 (s, 3 H), 2.34 (s, 3 H), 2.34 (hept, J=6.9 Hz, 2 H), 2.29 (s, 3 H), 1.78 (p, J=8.1 Hz, 1 H), 1.02 (d, J=6.9 Hz, 6 H). MS(CI) m/e 304 (M+H).

EXAMPLE 20

N-{3-[4-amino-2-(ethoxymethyl)-6,7-dimethyl-1H-imidazo[4,5-c]pyridin-1-yl]propyl}acetamide

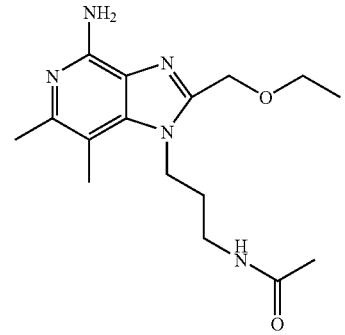

Part A Using the general method of Example 17 Part D, a pyridine solution of tert-butyl 3-[(3-amino-5,6-dimethyl-2-phenoxypyridin-4-yl)amino]propylcarbamate (see Example 17 Part C) was treated with ethoxyacetyl chloride (21.81 g, 178 mmol). The crude product was combined with dichloromethane (2 L) and water (2 L). The pH was adjusted to 12 with 50% sodium hydroxide and the mixture was stirred for 30 minutes. The organic phase was separated, dried over magnesium sulfate and then concentrated under reduced pressure. The residue was diluted with heptane and then concentrated to remove residual pyridine. This procedure was repeated several times to provide 64.8 g of tert-butyl 3-[2-(ethoxymethyl)-6,7-dimethyl-4-phenoxy-1H-imidazo [4,5-c]pyridin-1-yl]propylcarbamate as a brown tar.

Part B

Ammonium acetate (500 g) and tert-butyl 3-[2-(ethoxymethyl)-6,7-dimethyl-4-phenoxy-1H-imidazo[4,5-c]pyridin-1-yl]propylcarbamate (35.09 g, 77 mmol) were combined in a 2 L flask. The neck of the flask was stuffed with a wad of paper towels. The reaction mixture was heated with stirring at 150° C. for 27 hours. The reaction mixture was allowed to cool to ambient temperature and then it was placed in an ice bath. Ammonium hydroxide was added until the pH reached 11. Sodium hydroxide (50%) was added until the pH reached 14. The resulting precipitate was isolated by filtration and then dissolved in chloroform (4 L). The chloroform solution was divided into two portions and each was washed with saturated potassium carbonate (2×2 L). The organics were combined, dried over magnesium sulfate and then concentrated under reduced pressure to provide 30.3 g of crude product. This material was slurried with methyl acetate to provide 13.7 g of N-{3-[4-amino-2-(ethoxymethyl)-6,7-dimethyl-1H-imidazo[4,5-c]pyridin-1-yl] propyl}acetamide as a gray solid, m.p. 161.8–162.3° C.

Analysis: Calculated for $C_{16}H_{25}N_5O_2$: % C, 60.17; % H, 7.89; % N, 21.93. Found: % C, 59.97; % H, 7.70; % N, 22.19. $^1$H NMR (Bruker 300 MHz, CHCl$_3$-d) δ 5.92 (t, J=4.9 Hz, 1 H), 4.89 (s, 2 H), 4.71 (s, 2 H), 4.36 (t, J=8.1 Hz, 2 H), 3.62 (q, 6.8 Hz, 2 H), 3.33 (q, J=6.2 Hz, 2 H), 2.44 (s, 6 H), 2.03 (p, 8.1 Hz, 2 H), 1.95 (s, 3 H), 1.24 (t, J=6.8 Hz, 3 H). MS(CI) m/e 320 (M+H).

EXAMPLE 21

1-(3-aminopropyl)-2-(ethoxymethyl)-6,7-dimethyl-1H-imidazo[4,5-c]pyridin-4-amine

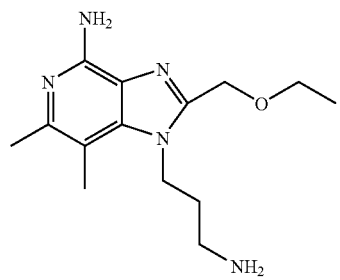

Using the general method of Example 18, N-{3-[4-amino-2-(ethoxymethyl)-6,7-dimethyl-1H-imidazo[4,5-c]pyridin-1-yl]propyl}acetamide (13.14 g, 4.1 mmol) was hydrolyzed and purified to provide 10.81 g of 1-(3-aminopropyl)-2-(ethoxymethyl)-6,7-dimethyl-1H-imidazo[4,5-c]pyridin-4-amine as a brown solid, m.p. 126.8–127.2° C.

Analysis: Calculated for $C_{14}H_{23}N_5O$: % C, 60.62; % H, 8.36; % N, 25.25. Found: % C, 60.49; % H, 8.38; % N, 25.33. $^1$H NMR (Bruker 300 MHz, CHCl$_3$-d) δ 4.91 (s, 2 H), 4.73 (s, 2 H), 4.43 (t, J=8.1 Hz, 2 H), 3.59 (q, J=6.8 Hz, 2 H), 2.81 (t, J=6.8 Hz, 2 H), 2.47 (s, 3 H), 2.45 (s, 3 H), 1.94 (p, J=8.1 Hz, 2 H), 1.22 (t, J=6.8 Hz, 3 H), 1.08 (s, 2 H). MS(CI) m/e 278 (M+H).

EXAMPLE 22

N-{3-[4-amino-2-(ethoxymethyl)-6,7-dimethyl-H-imidazo[4,5-c]pyridin-1-yl]propyl}-2-methylpropanamide

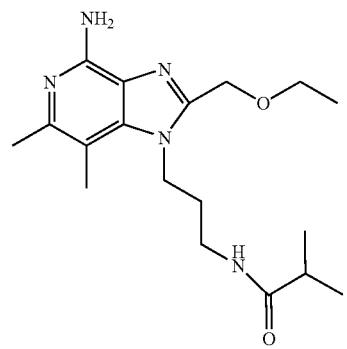

Using the method of Example 19, 1-(3-aminopropyl)-2-(ethoxymethyl)-6,7-dimethyl-1H-imidazo[4,5-c]pyridin-4-amine (1.00 g, 3.6 mmol) was reacted with isobutyryl chloride (0.42 mL, 40 mmol) to provide 0.74 g of N-{3-[4-amino-2-(ethoxymethyl)-6,7-dimethyl-1H-imidazo[4,5-c] pyridin-1-yl]propyl}-2-methylpropanamide as an off white solid, m.p. 179.1–179.7° C.

Analysis: Calculated for $C_{18}H_{29}N_5O_2$: % C, 62.22; % H, 8.41; % N, 20.16. Found: % C, 62.35; % H, 8.50; % N, 20.28 $^1$H NMR (Bruker 300 MHz, DMSO-d$_6$) δ 7.83 (t, J=5.6 Hz, 1 H), 5.73 (s, 2 H), 4.62 (s, 2 H), 4.26 (t, J=8.1 Hz, 2 H), 3.51 (q, J=6.9 Hz, 2 H), 3.16 (q, J=6.2 Hz, 2 H), 2.36 (s, 3 H), 2.34 (hept, J=6.9 Hz, 1 H), 2.30 (s, 3 H), 1.85 (p, J=8.1 Hz, 2 H), 1.13 (t, J=7.5 Hz, 3 H), 1.01 (d, J=6.9 Hz, 6 H). MS(CI) m/e 348 (M+H).

EXAMPLE 23

N-[2-(4-amino-2,6,7-trimethyl-1H-imidao[4,5-c]pyridin-1-yl)ethyl]acetamide

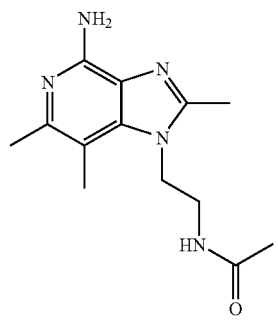

Part A

A solution of 2,4-dichloro-5,6-dimethyl-3-nitropyridine (60 g, 271 mmol) in anhydrous N,N-dimethylformamide (600 mL) was cooled to 0° C. Triethylamine (44.8 mL, 326 mmol) was added drop wise followed by tert-butyl 2-aminoethylcarbamate (52.2 g, 326 mmol). After 30 minutes the ice bath was removed and the reaction mixture was heated to 60° C. The reaction was heated at 60° C. overnight and then it was concentrated under reduced pressure to provide an orange oil. The oil was dissolved in ethyl acetate (1 L), washed with water (3×500 mL), dried over magnesium sulfate and then concentrated under reduced pressure to provide a yellow oil. The oil was triturated with methanol (~100 mL). The resulting solid was isolated by filtration and washed with cold methanol to provide 72.3 g of tert-butyl 2-[(2-chloro-5,6-dimethyl-3-nitropyridin-4-yl)amino]ethylcarbamate as a solid.

Part B

Phenol (1.19 g, 12.6 mmol) was added in portions to a chilled (0° C.) suspension of sodium hydride (0.52 g of 60%, 13.1 mmol) in diglyme (4 mL). The reaction mixture was then stirred for 30 minutes. A warm solution of tert-butyl 2-[(2-chloro-5,6-dimethyl-3-nitropyridin-4-yl)amino]ethylcarbamate (3.0 g, 8.70 mmol) in diglyme (6 mL) was added and the reaction mixture was heated at 90° C. overnight. The reaction mixture was cooled and poured slowly into water (100 mL). The resulting solid was isolated by filtration, washed with water, dried and then recrystallized from isopropanol (25 mL) to provide 2.07 g of tert-butyl 2-[(2,3-dimethyl-5-nitro-6-phenoxypyridin-4-yl)amino]ethylcarbamate as white needles. The reaction was repeated using 66.5 g of starting material to provide 50.4 g of product as white needles, m.p. 158–160° C.

Part C

Catalyst (5 g of 5% platinum on carbon) was added to a warm solution of tert-butyl 2-[(2,3-dimethyl-5-nitro-6-phenoxypyridin-4-yl)amino]ethylcarbamate (50.4 g) in a mixture of toluene (500 mL) and methanol (40 mL). The mixture was placed under hydrogen pressure (50 psi, $3.4 \times 10^5$ Pa). After 2 hours more catalyst (4 g) was added and the hydrogenation continued overnight. The reaction mixture was filtered through a layer of Celite® filter aid and the filter cake was washed with hot toluene (1 L). The filtrate was concentrated under reduced pressure to provide 45.1 g of tert-butyl 2-[(3-amino-5,6-dimethyl-2-phenoxypyridin-4-yl)amino]ethylcarbamate as a white solid.

Part D

A mixture of tert-butyl 2-[(3-amino-5,6-dimethyl-2-phenoxypyridin-4-yl)amino]ethylcarbamate (43.7 g, 117 mmol), triethyl orthoacetate (22.6 mL, 123 mmol), pyridine hydrochloride (4.4 g) and toluene (440 mL) was heated at reflux for 30 minutes. The reaction mixture was concentrated under reduced pressure to provide a brown oil. The oil was dissolved in ethyl acetate (1 L) and washed with water (2×500 mL). The aqueous washes were combined and extracted with ethyl acetate (2×500 mL). The combined organics were washed with brine, dried over magnesium sulfate and then concentrated under reduced pressure to provide 46.4 g of tert-butyl 2-(2,6,7-trimethyl-4-phenoxy-1H-imidazo[4,5-c]pyridin-1-yl)ethylcarbamate as a white solid, m.p. 180–182° C.

Part E

A mixture of ammonium acetate (95 g) and tert-butyl 2-(2,6,7-trimethyl-4-phenoxy-1H-imidazo[4,5-c]pyridin-1-yl)ethylcarbamate (9.5 g) was heated at 160° C. in a sealed tube for 24 hours. The reaction mixture was allowed to cool to ambient temperature and then it was partitioned between water and chloroform. The aqueous layer was made basic (pH 13) with 50% sodium hydroxide and then extracted with chloroform (10×400 mL). The combined organics were dried over magnesium sulfate and then concentrated under reduced pressure to provide a brown solid. The solid was dissolved in warm isopropanol (80 mL) and then combined with 1M hydrochloric acid in diethyl ether (23.7 mL). The resulting precipitate was isolated by filtration, washed with cold isopropanol and diethyl ether, and then dried in a vacuum oven at 80° C. overnight to provide 5.0 g of N-[2-(4-amino-2,6,7-trimethyl-1H-imidao[4,5-c]pyridin-1-yl)ethyl]acetamide hydrochloride as a white solid, m.p.>250° C. Analysis: Calculated for: $C_{13}H_{19}N_5O.1.00$ HCl: % C, 52.43; % H, 6.77; % N, 23.52. Found: % C, 52.25; % H, 6.81; % N, 23.41.

The reaction was repeated using 34 g of starting material to provide 18 g of the acetamide hydrochloride as a light tan solid.

EXAMPLE 24

1-(2-aminoethyl)-2,6,7-trimethyl-1H-imidazo[4,5-c]pyridin-4-amine

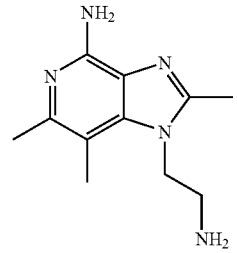

N-[2-(4-Amino-2,6,7-trimethyl-1H-imidao[4,5-c]pyridin-1-yl)ethyl]acetamide hydrochloride (18 g), hydrochloric acid (231 mL) and ethanol (350 mL) were combined and heated at 90° C. overnight. The reaction mixture was allowed to cool to ambient temperature and then it was diluted with diethyl ether (200 mL). The resulting precipitate was isolated by filtration, washed with cold ethanol and with diethyl ether, and then dried in a vacuum oven at 80° C. overnight to provide 17.3 g of 1-(2-aminoethyl)-2,6,7-trimethyl-1H-imidazo[4,5-c]pyridin-4-amine hydrochloride as white needles.

Analysis: Calculated for $C_{11}H_{17}N_5.2.8$ HCl. $0.25H_2O$: % C, 40.32; % H, 6.26; % N, 30.83. Found: % C, 40.54; % H, 6.15; % N, 30.87. $^1$H NMR (300 MHz, DMSO-$d_6$) δ 8.19 (t, J=6.2 Hz, 1 H), 7.91 (s, 2 H), 4.34 (t, J=6.6 Hz, 2 H), 3.39 (quartet, J=6.4 Hz, 2 H), 2.56 (s, 3 H), 2.43 (d, J=8.1 Hz, 6 H), 1.77 (s, 3 H); MS(CI) m/e 262 (M+H)

EXAMPLE 25

N-[2-(4-amino-2,6,7-trimethyl-1H-imidazo[4,5-c]pyridin-1-yl)ethyl]-2-methylpropanamide

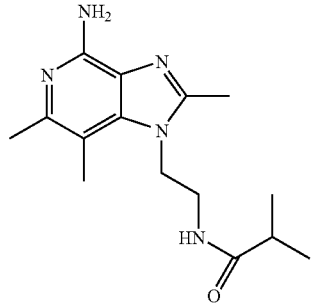

Isobutyryl chloride (1.3 mL, 12.2 mmol) was added dropwise to a mixture of 1-(2-aminoethyl)-2,6,7-trimethyl-1H-imidazo[4,5-c]pyridin-4-amine hydrochloride (4.0 g of material from Example 24, 12.2 mmol), triethylamine (85 mL, 610 mmol) and dichloromethane (400 mL). After 15 minutes analysis by high performance liquid chromatography indicated that the reaction was complete. The solvents were removed under reduced pressure. The residue was partitioned between chloroform (250 mL) and water (250 mL) containing 10 g of sodium carbonate (pH 12). This mixture was placed in a continuous extractor and extracted with chloroform for 24 hours. The extract was dried over magnesium sulfate and then concentrated under reduced pressure to provide a light yellow oil. The oil was purified by chromatography (silica gel eluting with 85/15 dichloromethane/methanol) to provide 2.63 g of N-[2-(4-amino-2,6,7-trimethyl-1H-imidazo[4,5-c]pyridin-1-yl)ethyl]-2-methylpropanamide as a white powder, m.p. 220–222° C.

Analysis: Calculated for $C_{15}H_{23}N_5O$: % C, 62.26; % H, 8.01; % N, 24.20. Found: % C, 61.92; % H, 7.97; % N, 24.38.

EXAMPLE 26

1-(4-aminobutyl)-2-(ethoxymethyl)-7-methyl-1H-imidazo[4,5-c]pyridin-4-amine

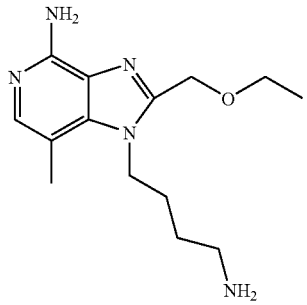

Part A

Propanenitrile (120 mL) was added to malonyl dichloride (100 g) and the reaction mixture was stirred under nitrogen for 24 hours. Dioxane (200 mL) was added. The resulting solid was isolated by filtration, washed with water and suction dried. It was dissolved in methanol (~75 mL) and then combined with dioxane (300 mL). The reaction volume was reduced under reduced pressure until a thick white precipitate formed. The resulting precipitate was isolated by filtration, washed with dioxane and dried to provide 64.4 g of 6-chloro-4-hydroxy-5-methyl-1H-pyridin-2-one hydrochloride as a white solid.

Part B

6-Chloro-4-hydroxy-5-methyl-1H-pyridin-2-one hydrochloride (64 g) was dissolved in sulfuric acid (325 mL) while cooling in an ice bath. Nitric acid was added dropwise over a period of 90 minutes. The reaction mixture was allowed to stir for an additional 30 minutes and then it was poured into ice water (2 L). The resulting precipitate was isolated by filtration, washed with water and then dried to provide 42.5 g of 6-chloro-4-hydroxy-5-methyl-3-nitro-1H-pyridin-2-one as a light yellow solid.

Part C

Triethylamine (102 mL, 742 mmol) was added to a cooled (ice bath) mixture of 6-chloro-4-hydroxy-5-methyl-3-nitro-1H-pyridin-2-one (50.6 g, 247 mmol) and anhydrous dichloromethane (1800 mL). Trifluoromethanesulfonic anhydride (83.2 mL, 495 mmol) was added drop wise over a period of 45 minutes. After 1 hour, tert-butyl 4-aminobutylcarbamate (51.2 g, 272 mmol) was added over period of 20 minutes. The reaction was allowed to warm to ambient temperature overnight. The reaction mixture was washed with water (4×1 L), dried over magnesium sulfate, and then concentrated under reduced pressure to provide an orange oil. The oil was purified by chromatography (1100 mL of silica gel eluting with 50/50 ethyl acetate/hexanes to provide 93.5 g 4-({4-[(tert-butoxycarbonyl)amino]butyl}amino)-6-chloro-5-methyl-3-nitropyridin-2-yl trifluoromethanesulfonate as a yellow oil.

Part D

The crude product from Part C was combined with toluene (2 L), triethylamine (25.4 mL), and dibenzylamine (35.5 mL) and heated at reflux for 1 hour. The reaction mixture was allowed to cool to ambient temperature, washed with water (4×1 L) and brine (200 mL), dried over magnesium sulfate and then concentrated under reduced pressure to provide 100 g of an orange oil. A portion (70 g) was purified by column chromatography (1200 mL of silica gel eluting with 20/80 ethyl acetate/hexanes) to provide 52 g of tert-butyl 4-{[2-chloro-6-(dibenzylamino)-3-methyl-5-nitropyridin-4-yl]amino}butylcarbamate as a light yellow oil.

Part E

Sodium borohydride (0.40 g, 10.6 mmol) was slowly added to a solution of nickel(II) chloride hexahydrate (0.70 g, 2.93 mmol) in methanol (75 mL). After 15 minutes a solution of tert-butyl 4-{[2-chloro-6-(dibenzylamino)-3-methyl-5-nitropyridin-4-yl]amino}butylcarbamate (3.25 g, 5.87 mmol) dissolved in a mixture of methanol (25 mL) and dichloromethane (20 mL) was added to the reaction mixture. Sodium borohydride (0.93 g) was slowly added. After 30 minutes analysis by high performance liquid chromatography indicated that the reaction was complete. The reaction was scaled up to 48.7 g of the starting material using the same conditions. The small and large scale reaction mixtures were combined and filtered through a layer of Celite® filter aid. The filtrate was passed through a plug of silica gel and the plug was washed with 50/50 dichloromethane/methanol. The filtrate was concentrated under reduced pressure to provide 46.3 g of tert-butyl 4-{[3-amino-6-chloro-4-(dibenzylamino)-5-methylpyridin-4-yl]amino}butylcarbamate as a light brown oil.

Part F

Triethylamine (12.2 mL) was added to a chilled (0° C.) solution of the material from Part E in dichloromethane (300 mL). A solution of ethoxyacetyl chloride (10.8 g) in dichloromethane (100 mL) was added via an addition funnel. The reaction was allowed to warm to ambient temperature overnight. Analysis indicated that some starting material remained so 0.2 eq of the acid chloride was added. After 1 hour the reaction mixture was washed with water (3×500 mL), dried over magnesium sulfate and then concentrated under reduced pressure to provide tert-butyl 4-{[2-chloro-6-(dibenzylamino)-5-(2-ethxoyacetylamino)-3-methylpyridin-4-yl]amino}butylcarbamate as a brown oil. The oil was dissolved in pyridine (300 mL). Pyridine hydrochloride (40 g) was added and the reaction mixture was heated at reflux for 4 hours. The reaction mixture was allowed to cool to ambient temperature and then it was concentrated under reduced pressure. The residue was dissolved in ethyl acetate (500 mL) and washed with water (500 mL). An emulsion formed and was cleared by adding sodium chloride to the aqueous layer. The organic layer was dried over magnesium sulfate and concentrated under reduced pressure to provide 52.1 g of a dark brown oil. This oil was purified by chromatography (silica gel eluting with 30/70 ethyl acetate/hexanes) to provide 24.8 g of tert-butyl 4-[6-chloro-4-(dibenzylamino)-2-(ethoxymethyl)-7-methyl-1H-imidazo[4,5-c]pyridin-1-yl]butylcarbamate as a light yellow oil.

Part G

Trifluoroacetic acid (160 mL) was added over a period of 15 minutes to a chilled (0°) solution of the material from Part F in dichloromethane (500 mL). The reaction mixture was allowed to stir overnight and then it was concentrated under reduced pressure. The residue was partitioned between dichloromethane (500 mL) and 10% sodium hydroxide (500 mL). The base layer was extracted with dichloromethane (×2). The combined organics were dried over magnesium sulfate and then concentrated under reduced pressure to provide a brown oil. The oil was dissolved in isopropanol (100 mL) and then combined with 41 mL of 1 M hydrochloric acid in diethyl ether. Diethyl ether (200 mL) was slowly added to the mixture. The resulting precipitate was isolated by filtration, washed with ether and dried in a vacuum oven at 80° C. overnight to provide 11.25 g of the hydrochloride salt of the desired product as a white solid. The solid was dissolved in water (200 mL), combined with sodium carbonate (15 g), and then extracted with dichloromethane (3×500 mL). The combined extracts were dried over magnesium sulfate and then concentrated under reduced pressure to provide 10.2 g of 1-(4-aminobutyl)-N,N-dibenzyl-6-chloro-2-(ethoxymethyl)-7-methyl-1H-imidazo[4,5-c]pyridin-4-amine as a clear oil.

Part H

Under a nitrogen atmosphere, ammonium formate (13.7 g) was added to a mixture of 10% palladium on carbon (10 g) and ethanol (200 mL). The material from Part H was dissolved in a mixture of hot ethanol (600 mL) and methanol (400 mL) and then added to the reaction mixture. The reaction mixture was heated at reflux for 4 hours and then allowed to cool to ambient temperature overnight. Analysis indicated that the reaction was only about one half complete so catalyst (5 g) and ammonium formate (5 g) were added and the reaction mixture was heated at reflux for 4 hours. The reaction mixture was allowed to cool to ambient temperature and then it was filtered through a layer of Celite® filter aid. The filter cake was washed with 50/50 ethanol/methanol (1 L). The solvents were removed under reduced pressure to provide a clear oil. The oil was partitioned between dichloromethane (500 mL) and 10% sodium hydroxide (200 mL). The aqueous layer was extracted with dichloromethane. The combined organic layers were dried over magnesium sulfate and then concentrated under reduced pressure to provide 4.30 g of 1-(4-aminobutyl)-2-(ethoxymethyl)-7-methyl-1H-imidazo[4,5-c]pyridin-4-amine as a clear oil which partially solidified on standing.

EXAMPLE 27

N-[4-(4-amino-6,7-dimethyl-2-propyl-1H-imidazo[4,5-c]pyridin-1-yl)butyl]acetamide

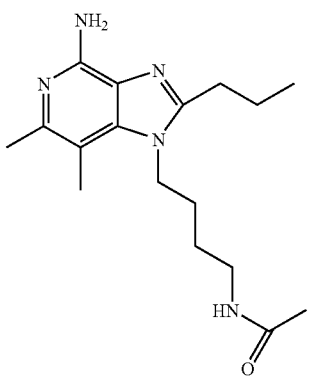

Part A Using the general method of Example 12 Part E, tert-butyl 4-[(3-amino-5,6-dimethyl-2-phenoxypyridin-4-yl)amino]butylcarbamate (3.41 g, 8.51 mmol) was reacted with trimethyl orthobutyrate (1.50 mL, 9.37 mmol) to provide 3.2 g of crude tert-butyl 4-(6,7-dimethyl-4-phenoxy-2-propyl-1H-imidazo[4,5-c]pyridin-1-yl)butylcarbamate as purplish semisolid.

Part B

A mixture of the material from Part A and ammonium acetate (32 g) was heated in a sealed tube at 150° C. overnight. More ammonium acetate (10 g) was added, the pressure flask was resealed and the mixture was heated at 160° C. for 20 hours. The reaction mixture was allowed to cool to ambient temperature then it was diluted with water, made basic with ammonium hydroxide, saturated with sodium chloride and then extracted with chloroform (×4). The extracts were combined, washed with brine, dried over magnesium sulfate and then concentrated under reduced pressure to provide a yellow solid. This solid was dissolved in chloroform, washed with 2% sodium hydroxide, dried over magnesium sulfate and then concentrated under reduced pressure to provide a yellow orange solid. This solid was recrystallized from isopropanol to provide N-[4-(4-amino-6,7-dimethyl-2-propyl-1H-imidazo[4,5-c]pyridin-1-yl)butyl]acetamide as a solid, m.p. 200.1–201.4° C.

Analysis: Calculated for $C_{17}H_{27}N_5O$: % C, 64.32; % H, 8.57; % N, 22.06. Found: % C, 64.21; % H, 8.49; % N, 21.96. $^1$H NMR (300 MHz, DMSO-$d_6$) δ 7.81 (t, J=5.4 Hz, 1 H), 5.56 (s, 2 H), 4.18 (t, J=7.8 Hz, 2 H), 3.06 (apparent q, J=6.6 Hz, 2 H), 2.75 (t, J=7.5 Hz, 2 H), 2.35 (s, 3 H), 2.30 (s, 3 H), 1.78 (sextet, J=7.4 Hz, 2 H), 1.78 (s, 3 H), 1.7–1.5 (m, 2 H), 1.5–1.35 (m, 2 H), 0.99 (t, J=7.3 Hz, 3H); MS (CI) m/e 318.2299 (318.2294 calcd for $C_{17}H_{27}N_5O$, M+H).

EXAMPLES 28–41

The compounds in the table below were prepared using the following method. The appropriate acid chloride (1.1 eq.) was added to a test tube containing a solution of 1-(4-aminobutyl)-6,7-dimethyl-1H-imidazo[4,5-c]pyridin-4-amine (25 mg; see Example 13) in chloroform (5 mL). The test tube was capped and then placed on a shaker at ambient temperature overnight. The solvent was removed by vacuum centrifugation. The residue was purified by prep HPLC using the method described above to provide the trifluoroacetate salt of the desired compound. The structures were confirmed by $^1$H NMR spectroscopy. The table below shows the structure of the free base and the observed accurate mass (m+H).

| Example Number | $R_1$ | Accurate Mass (obs) |
|---|---|---|
| 28 | cyclopropyl | 302.2001 |
| 29 | butyl | 318.2316 |
| 30 | cyclopentyl | 330.2303 |
| 31 | phenyl | 338.1998 |
| 32 | benzyl | 352.2148 |
| 33 | 4-fluorophenyl | 356.1915 |
| 34 | thien-2-ylmethyl | 358.1723 |

-continued

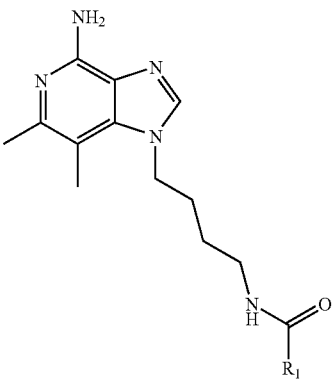

| Example Number | R₁ | Accurate Mass (obs) |
|---|---|---|
| 35 | 3-cyanophenyl | 363.1960 |
| 36 | 2-phenylethyl | 366.2309 |
| 37 | 3-methoxyphenyl | 368.2112 |
| 38 | benzyloxymethyl | 382.2244 |
| 39 | 2-naphthyl | 388.2166 |
| 40 | 3-trifluoromethylphenyl | 406.1880 |
| 41 | 4-trifluoromethoxyphenyl | 422.1807 |

EXAMPLE 42

(1R*,2R*)-N-[3-(4-amino-6,7-dimethyl-1H-imidazo[4,5-c]pyridin-1-yl)butyl]-2-phenylcyclopropanecarboxamide

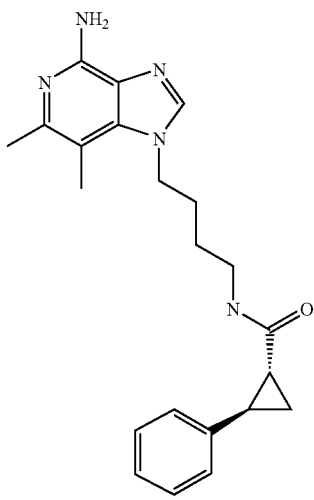

Using the method of Examples 28–41, trans-2-phenyl-1-cyclopropanecarbonyl chloride was reacted with 1-(4-aminobutyl)-6,7-dimethyl-1H-imidazo[4,5-c]pyridin-4-amine to provide the desired product. The observed accurate mass was 378.2294.

EXAMPLES 43–59

The compounds in the table below were prepared using the following method. The acid chloride (1.1 eq.) was added to a test tube containing a solution of 1-(4-aminobutyl)-2-ethoxymethyl-6-methyl-1H-imidazo[4,5-c]pyridin-4-amine (25 mg; see Example 10) in chloroform (5 mL). The test tube was capped and then placed on a shaker at ambient temperature for 16 hours. The solvent was removed by vacuum centrifugation. The residue was purified by prep HPLC using the method described above to provide the trifluoroacetate salt of the desired compound. The structures were confirmed by $^1$H NMR spectroscopy. The table below shows the structure of the free base and the observed accurate mass (m+H).

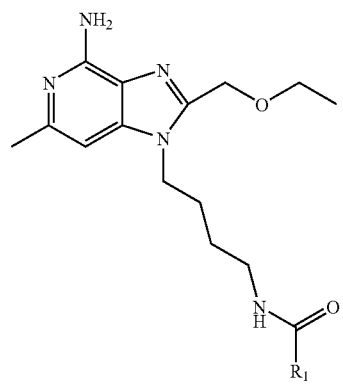

| Example Number | R₁ | Accurate Mass (obs) |
|---|---|---|
| 43 | cyclopropyl | 346.2256 |
| 44 | butyl | 362.25.70 |
| 45 | phenyl | 382.2262 |
| 46 | cyclohexyl | 388.2722 |
| 47 | benzyl | 396.2419 |
| 48 | 4-fluorophenyl | 400.2159 |
| 49 | thien-2-ylmethyl | 402.1990 |
| 50 | 2-phenylethyl | 410.2563 |
| 51 | 3-methoxyphenyl | 412.2379 |
| 52 | 4-methoxyphenyl | 412.2375 |
| 53 | 2-chloropyrid-5-yl | 417.1829 |
| 54 | 3-pyridyl | 383.2222 |
| 55 | benzyloxymethyl | 426.2521 |
| 56 | 2-naphthyl | 432.2412 |
| 57 | 3-trifluoromethylphenyl | 450.2139 |
| 58 | 4-trifluoromethylphenyl | 450.2144 |
| 59 | 4-trifluoromethoxyphenyl | 466.2075 |

EXAMPLE 60

(1R*,2R*)-N-{3-[4-amino-2-(ethoxymethyl)-6-methyl-1H-imidazo[4,5-c]pyridin-1-yl]butyl}-2-phenylcyclopropanecarboxamide

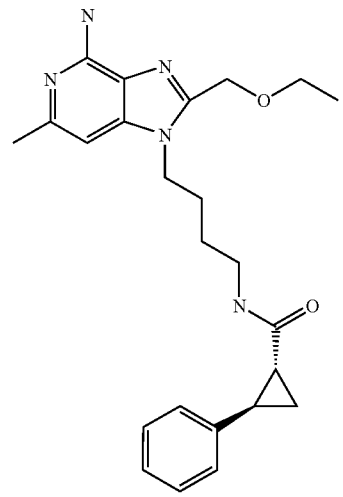

Using the method of Examples 43–59, trans-2-phenyl-1-cyclopropanecarbonyl chloride was reacted with 1-(4-aminobutyl)-2-ethoxymethyl-6-methyl-1H-imidazo[4,5-c]pyridin-4-amine to provide the desired product. The observed accurate mass was 422.2578.

EXAMPLES 61–75

The compounds in the table below were prepared using the following method. The acid chloride (1.1 eq.) was added to a test tube containing a solution of 2-(ethoxymethyl)-6,7-dimethyl-1-(2-piperidin-4-ylethyl)-1H-imidazo[4,5-c]pyridin-4-amine (25 mg; see Example 14) in chloroform (5 mL). The test tube was capped and then placed on a shaker at ambient temperature for 16 hours. The solvent was removed by vacuum centrifugation. The residue was purified by prep HPLC using the method described above to provide the trifluoroacetate salt of the desired compound. The structures were confirmed by $^1$H NMR spectroscopy. The table below shows the structure of the free base and the observed accurate mass (m+H).

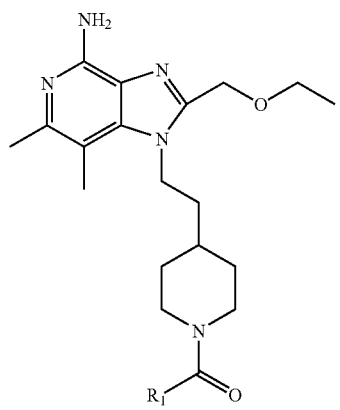

| Example Number | $R_1$ | Accurate Mass (obs) |
|---|---|---|
| 61 | cyclopropyl | 400.2738 |
| 62 | butyl | 416.3041 |
| 63 | phenyl | 436.2722 |
| 64 | cyclohexyl | 442.3210 |
| 65 | benzyl | 450.2881 |
| 66 | 4-fluorophenyl | 454.2568 |
| 67 | thien-2-ylmethyl | 456.2443 |
| 68 | 3-cyanophenyl | 461.2672 |
| 69 | 2-phenylethyl | 464.3046 |
| 70 | 2-chloropyrid-5-yl | 471.2292 |
| 71 | benzyloxymethyl | 480.2988 |
| 72 | 2-naphthyl | 486.2876 |
| 73 | 3-trifluoromethylphenyl | 504.2592 |
| 74 | 4-trifluoromethylphenyl | 504.2607 |
| 75 | 4-trifluoromethoxyphenyl | 520.2529 |

EXAMPLE 76

2-(ethoxymethyl)-6,7-dimethyl-1-[2-(1-{[(1R*,2R*)-2-phenylcyclopropyl]carbonyl}piperidin-4-yl)ethyl]-1H-imidazo[4,5-c]pyridin-4-amine

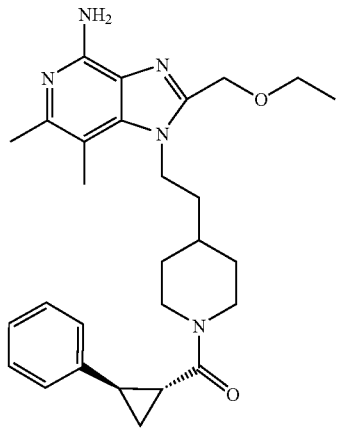

Using the method of Examples 61–75, trans-2-phenyl-1-cyclopropanecarbonyl chloride was reacted with 2-(ethoxymethyl)-6,7-dimethyl-1-(2-piperidin-4-ylethyl)-1H-imidazo[4,5-c]pyridin-4-amine to provide the desired product. The observed accurate mass was 476.3039.

EXAMPLES 77–92

The compounds in the table below were prepared using the following method. The acid chloride (1.1 eq.) was added to a test tube containing a solution of 1-(3-aminopropyl)-2,6,7-trimethyl-1H-imidazo[4,5-c]pyridin-4-amine (25 mg; see Example 18) in chloroform (5 mL). The test tube was capped, vortexed and then placed on a shaker at ambient temperature for 16 hours. The solvent was removed by vacuum centrifugation. The residue was purified by prep HPLC using the method described above to provide the trifluoroacetate salt of the desired compound. The table below shows the structure of the free base and the observed accurate mass (m+H).

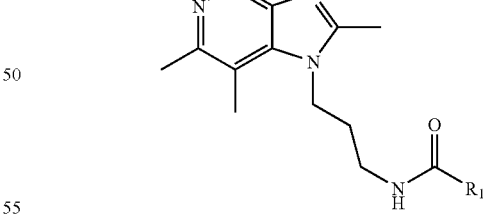

| Example Number | $R_1$ | Accurate Mass (obs) |
|---|---|---|
| 77 | cyclopropyl | 302.1994 |
| 78 | butyl | 318.2302 |
| 79 | cyclohexyl | 344.2440 |
| 80 | benzyl | 352.2141 |
| 81 | 4-fluorophenyl | 356.1890 |
| 82 | thien-2-ylmethyl | 358.1687 |
| 83 | 4-cyanophenyl | 363.1921 |
| 84 | 3-cyanophenyl | 363.1939 |
| 85 | 2-phenylethyl | 366.2285 |
| 86 | 3-methoxyphenyl | 368.2092 |

-continued

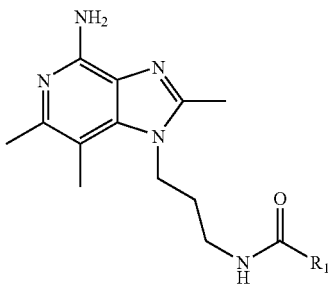

| Example Number | R₁ | Accurate Mass (obs) |
|---|---|---|
| 87 | 4-methoxyphenyl | 368.2088 |
| 88 | 2-chloropyrid-5-yl | 373.1527 |
| 89 | 2-naphthyl | 388.2132 |
| 90 | 3-trifluoromethylphenyl | 406.1855 |
| 91 | 4-trifluoromethylphenyl | 406.1857 |
| 92 | 4-trifluoromethoxyphenyl | 422.1805 |

EXAMPLE 93

(1R*,2R*)-N-{3-[4-amino-2,6,7-trimethyl-1H-imidazo[4,5-c]pyridin-1-yl]propyl}-2-phenylcyclopropanecarboxamide

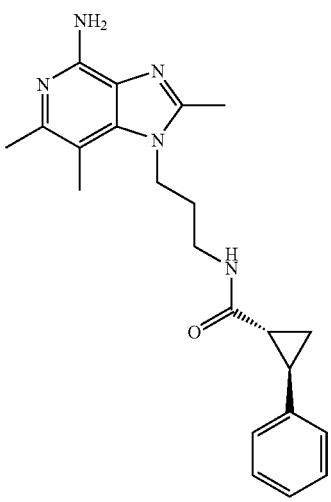

Using the method of Examples 78–92, trans-2-phenyl-1-cyclopropanecarbonyl chloride was reacted with 1-(3-aminopropyl)-2,6,7-trimethyl-1H-imidazo[4,5-c]pyridin-4-amine to provide the desired product. The observed accurate mass was 378.2298.

EXAMPLES 94–111

The compounds in the table below were prepared using the following method. The acid chloride (1.1 eq.) was added to a test tube containing a solution of 1-(3-aminopropyl)-2-(ethoxymethyl)-6,7-dimethyl-1H-imidazo[4,5-c]pyridin-4-amine (25 mg; see Example 21) in chloroform (5 mL). The test tube was capped, vortexed and then placed on a shaker at ambient temperature for 17 hours. The solvent was removed by vacuum centrifugation. The residue was purified by prep HPLC using the method described above to provide the trifluoroacetate salt of the desired compound. The table below shows the structure of the free base and the observed accurate mass (m+H).

| Example Number | R₁ | Accurate Mass (obs) |
|---|---|---|
| 94 | cyclopropyl | 346.2255 |
| 95 | butyl | 362.2542 |
| 96 | phenyl | 382.2256 |
| 97 | cyclohexyl | 388.2699 |
| 98 | benzyl | 396.2386 |
| 99 | 4-fluorophenyl | 400.2142 |
| 100 | thien-2-ylmethyl | 402.1981 |
| 101 | 4-cyanophenyl | 407.2186 |
| 102 | 3-cyanophenyl | 407.2209 |
| 103 | 2-phenylethyl | 410.2552 |
| 104 | 3-methoxyphenyl | 412.2364 |
| 105 | 4-methoxyphenyl | 412.2351 |
| 106 | 2-chloropyrid-5-yl | 417.1814 |
| 107 | benzyloxymethyl | 426.2489 |
| 108 | 2-naphthyl | 432.2388 |
| 109 | 3-trifluoromethylphenyl | 450.2116 |
| 110 | 4-trifluoromethylphenyl | 450.2121 |
| 111 | 4-trifluoromethoxyphenyl | 466.2067 |

EXAMPLE 112

(1R*,2R*)-N-{3-[4-amino-2-(ethoxymethyl)-6,7-diimethyl-1H-imidazo[4,5-c]pyridin-1-yl]propyl}-2-phenylcyclopropanecarboxamide

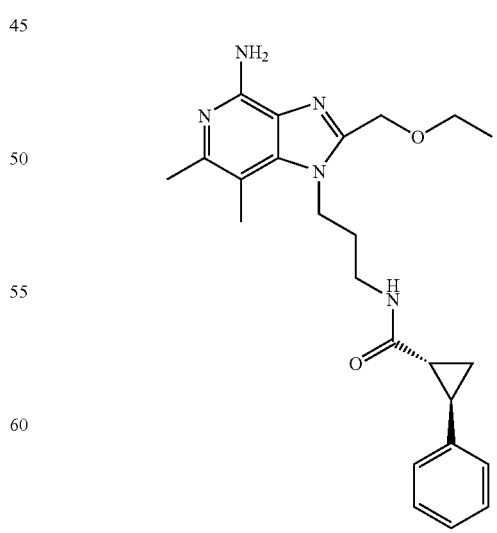

Using the method of Examples 94–111, trans-2-phenyl-1-cyclopropanecarbonyl chloride was reacted with 1-(3- aminopropyl)-2-(ethoxymethyl)-6,7-dimethyl-1H-imidazo[4,5-c]pyridin-4-amine to provide the desired product. The observed accurate mass was 422.2564.

EXAMPLES 113–134

The compounds in the table below were prepared using the following method. The acid chloride (1.1 eq.) was added to a test tube containing a solution of 1-(2-aminoethyl)-2,6,7-trimethyl-1H-imidazo[4,5-c]pyridin-4-amine (20 mg; see Example 24) in chloroform (5 mL). The test tube was capped, vortexed and then placed on a shaker at ambient temperature for 4 hours. The solvent was removed by vacuum centrifugation. The residue was purified by prep HPLC using the method described above to provide the trifluoroacetate salt of the desired compound. The table below shows the structure of the free base and the observed accurate mass (m+H).

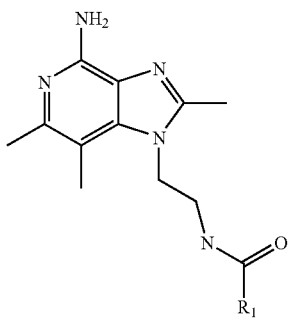

| Example Number | $R_1$ | Accurate Mass (obs) |
|---|---|---|
| 113 | cyclopropyl | 288.1804 |
| 114 | butyl | 304.2128 |
| 115 | phenyl | 324.1811 |
| 116 | cyclohexyl | 330.2275 |
| 117 | benzyl | 338.1967 |
| 118 | 4-fluorophenyl | 342.1731 |
| 119 | thien-2-ylmethyl | 344.1543 |
| 120 | 4-cyanophenyl | 349.1787 |
| 121 | 3-cyanophenyl | 349.1776 |
| 122 | 2-phenylethyl | 352.2119 |
| 123 | 3-methoxyphenyl | 354.1912 |
| 124 | 4-methoxyphenyl | 354.1899 |
| 125 | 2-chloropyrid-5-yl | 359.1385 |
| 126 | benzyloxymethyl | 368.2089 |
| 127 | 2-naphthyl | 374.1983 |
| 128 | 3-trifluoromethylphenyl | 392.1699 |
| 129 | 4-trifluoromethylphenyl | 392.1706 |
| 130 | 4-trifluoromethoxyphenyl | 408.1642 |
| 131 | acetoxymethyl | 320.1717 |
| 132 | 3,4-methylenedioxyphenyl | 368.1720 |
| 133 | 4-(methoxycarbonyl)phenyl | 382.1878 |
| 134 | 1-adamantyl | 382.2588 |

EXAMPLE 135

(1R*,2R*)-N-{3-[4-amino-2,6,7-trimethyl-1H-imidazo[4,5-c]pyridin-1-yl]ethyl}-2-phenylcyclopropanecarboxamide

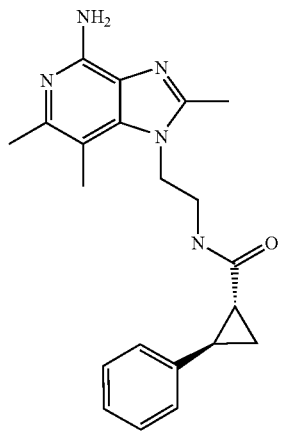

Using the method of Examples 113–134, trans-2-phenyl-1-cyclopropanecarbonyl chloride was reacted with 1-(2-aminoethyl)-2,6,7-trimethyl-1H-imidazo[4,5-c]pyridin-4-amine to provide the desired product. The observed accurate mass was 364.2125.

EXAMPLES 136–156

The compounds in the table below were prepared using the following method. The acid chloride (1.1 eq.) was added to a test tube containing a solution of 1-(4-aminobutyl)-2-(ethoxymethyl)-7-methyl-1H-imidazo[4,5-c]pyridin-4-amine (23.5 mg; see Example 26) in chloroform (5 mL). The test tube was capped and then placed on a shaker at ambient temperature for 4 hours. The solvent was removed by vacuum centrifugation. The residue was purified by prep HPLC using the method described above to provide the trifluoroacetate salt of the desired compound. The table below shows the structure of the free base and the observed accurate mass (m+H).

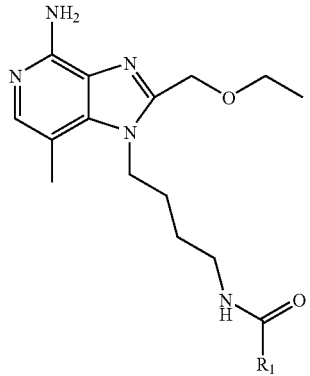

| Example Number | $R_1$ | Accurate Mass (obs) |
|---|---|---|
| 136 | cyclopropyl | 346.2249 |
| 137 | phenyl | 382.2234 |
| 138 | cyclohexyl | 388.2711 |
| 139 | benzyl | 396.2394 |
| 140 | 4-fluorophenyl | 400.2149 |

-continued

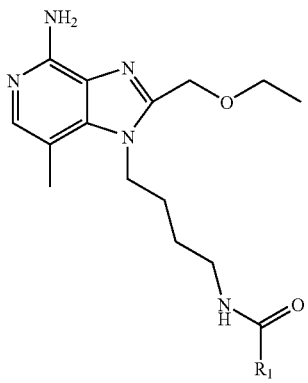

| Example Number | $R_1$ | Accurate Mass (obs) |
|---|---|---|
| 141 | thien-2-ylmethyl | 402.1946 |
| 142 | 4-cyanophenyl | 407.2206 |
| 143 | 3-cyanophenyl | 407.2177 |
| 144 | 2-phenylethyl | 410.2549 |
| 145 | 3-methoxyphenyl | 412.2350 |
| 146 | 4-methoxyphenyl | 412.2355 |
| 147 | 2-chloropyrid-5-yl | 417.1813 |
| 148 | benzyloxymethyl | 426.2506 |
| 149 | 2-naphthyl | 432.2390 |
| 150 | 3-trifluoromethylphenyl | 450.2125 |
| 151 | 4-trifluoromethylphenyl | 450.2096 |
| 152 | 4-trifluoromethoxyphenyl | 466.2045 |
| 153 | 4-(methoxycarbonyl)butyl | 420.2592 |
| 154 | 3,4-methylenedioxyphenyl | 426.2148 |
| 155 | 4-(methoxycarbonyl)phenyl | 440.2283 |
| 156 | 1-adamantyl | 440.3024 |

EXAMPLE 157

(1R*,2R*)-N-{3-[4-amino-2-(ethoxymethyl)-7-methyl-1H-imidazo[4,5-c]pyridin-1-yl]butyl}-2-phenyl-cyclopropanecarboxamide

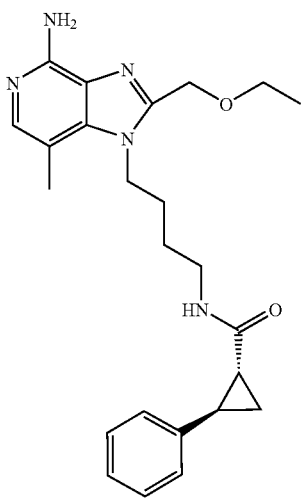

Using the method of Examples 136–156, trans-2-phenyl-1-cyclopropanecarbonyl chloride was reacted with 1-(4-aminobutyl)-2-ethoxymethyl-7-methyl-1H-imidazo[4,5-c] pyridin-4-amine to provide the desired product. The observed accurate mass was 422.2543.

EXAMPLE 158

N-{2-[4-amino-2-(ethoxymethyl)-6,7-dimethyl-1H-imidazo[4,5-c]pyridin-1-yl]-1,1-dimethylethyl}acetamide

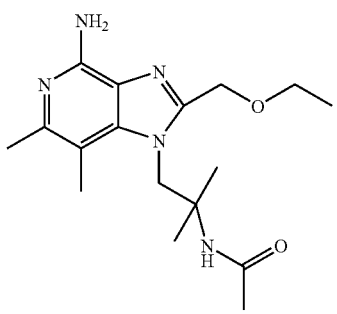

Part A

A stirred solution of 2,4-dichloro-5,6-dimethyl-3-nitropyridine (4.42 g, 20.0 mmol) in 50 mL of anhydrous DMF, under $N_2$, was treated with triethylamine (5.58 mL, 40.0 mol) and 1,2-diamino-2-methylpropane (2.10 mL, 20.0 mmol). After stirring for 24 h, the reaction mixture was concentrated under reduced pressure. The resulting oil was treated with $CH_2Cl_2$ (200 mL) and $H_2O$ (100 mL). The aqueous layer was made basic (pH-12) by addition of concentrated $NH_4OH$ solution. The layers were separated and the aqueous portion was extracted with an additional 100 mL of $CH_2Cl_2$. The combined organic portions were washed with $H_2O$ (2×) and brine. The organic portion was dried with $Na_2SO_4$ and concentrated to give an orange oil that solidified on standing. Column chromatography ($SiO_2$, 2% MeOH/$CHCl_3$) gave N'-(2-chloro-5,6-dimethyl-3-nitropyridin-4-yl)-2-methylpropane-1,2-diamine (3.14 g) as a yellow solid.

Part B

A solution of gave N'-(2-chloro-5,6-dimethyl-3-nitropyridin-4-yl)-2-methylpropane-1,2-diamine (3.14 g, 10.9 mmol) in 50 mL of $CH_2Cl_2$ was cooled to 0° C. under $N_2$ and treated with triethylamine (2.84 mL, 20.4 mmol) and acetic anhydride (1.01 mL, 10.7 mmol). After stirring for 2 h, the reaction was quenched by the addition of saturated aqueous $NaHCO_3$. $CH_2Cl_2$ (100 mL) was added and the organic layer was separated. The organic layer was then washed with cold $H_2O$ (2×) and brine. The organic portion was dried with $Na_2SO_4$ and concentrated to give N-{2-[(2-chloro-5,6-dimethyl-3-nitropyridin-4-yl)amino]-1,1-dimethylethyl}acetamide (2.80 g) as a yellow foam.

Part C

A 250 mL-round bottom flask was charged with NaH (60% oil dispersion, 534 mg, 13.3 mmol) under $N_2$. The NaH was washed with three portions of hexanes and dried under a stream of $N_2$. Dimethoxyethane (10 mL) was then added to the flask followed by phenol (1.25 g, 13.3 mmol). After stirring for 10 min, a solution of N-{2-[(2-chloro-5,6-dimethyl-3-nitropyridin-4-yl)amino]-1,1-dimethylethyl}acetamide (2.80 g, 8.89 mmol) in 15 mL of dimethoxyethane was added to the reaction mixture, drop wise, via cannula. The reaction mixture was then heated to reflux for 24 h. The cooled solution was then treated with 100 mL of EtOAc and washed successively with H$_2$O, 1% Na$_2$CO$_3$ solution (2×), H$_2$O and brine. The organic portion was dried with Na$_2$SO$_4$ and concentrated to give a brown oil. Column chromatography (SiO$_2$, 50% EtOAc/hexanes) gave N-{2-[(2,3-dimethyl-5-nitro-6-phenoxypyridin-4-yl)amino]-1,1-dimethylethyl}acetamide (2.40 g) as a yellow oil.

Part D

N-{2-[(2,3-dimethyl-5-nitro-6-phenoxypyridin-4-yl)amino]-1,1-dimethylethyl}acetamide (2.40 g, 6.45 mmol) was dissolved in 20 mL of toluene and treated with 0.2 g of Pt (5% on carbon). The reaction mixture was then shaken under H$_2$ (3 atm) for 24 h. Then reaction mixture was then treated with an additional 1.5 g of Pt (5% on carbon) and shaken an additional 8 h. The reaction mixture was then filtered through Celite, rinsing with toluene, and concentrated to give N-{2-[(3-amino-5,6-dimethyl-2-phenoxypyridin-4-yl)amino]-1,1-dimethylethyl}acetamide (1.80 g) as a colorless oil.

Part E

A solution of N-{2-[(3-amino-5,6-dimethyl-2-phenoxypyridin-4-yl)amino]-1,1-dimethylethyl}acetamide (1.80 g, 5.23 mmol) in 50 mL of CH$_2$Cl$_2$ was cooled to 0° C., under N$_2$, and treated with triethylamine (728 µL, 5.23 mmol) and ethoxyacetyl chloride (574 µL, 5.23 mmol). After stirring overnight, the reaction mixture was concentrated under reduced pressure. The resulting syrup was taken up in 50 mL of EtOH and treated with 3 mL of triethylamine. The solution was heated to reflux for 4 d. The reaction mixture was then concentrated and redissolved in 50 mL of xylenes and treated with pyridinium hydrochloride (0.5 g) and the mixture was heated to reflux for 4 d. The reaction mixture was concentrated and taken up in 100 mL of EtOAc and washed with saturated NaHCO$_3$ solution, H$_2$O (2×) and brine. The organic portion was dried over Na$_2$SO$_4$ and concentrated. The resulting syrup was purified by column chromatography (SiO$_2$, 80% EtOAc/hexanes) to give N-{2-[2-(ethoxymethyl)-6,7-dimethyl-4-phenoxy-1H-imidazo[4,5-c]pyridin-1-yl]-1,1-dimethylethyl}acetamide (980 mg) as a mustard colored foam.

Part F

A pressure flask was charged with N-{2-[2-(ethoxymethyl)-6,7-dimethyl-4-phenoxy-1H-imidazo[4,5-c]pyridin-1-yl]-1,1-dimethylethyl}acetamide (980 mg, 2.39 mmol) and ammonium acetate (1.25 g). The flask was sealed and heated to 160° C. The solids soon melted to give a viscous oil and heating was continued for 24 h. The reaction mixture was cooled and treated with H$_2$O and NH$_4$OH solution until pH reached ~12. The mixture was then extracted with CHCl$_3$ (3×). The combined organic portions were washed with brine, dried with Na$_2$SO$_4$ and concentrated. Column chromatography (SiO$_2$, 5% MeOH/CHCl$_3$ saturated with NH$_4$OH) gave N-{2-[4-amino-2-(ethoxymethyl)-6,7-dimethyl-1H-imidazo[4,5-c]pyridin-1-yl]-1,1-dimethylethyl}acetamide (584 mg) as a tan foam. MS m/z 334 (M+H). $^1$H NMR (300 MHz, CDCl$_3$) δ 5.57 (s, 1H), 4.92 (s, 2H), 4.77 (s, 2 H), 4.71 (br s, 2 H), 3.62 (q, J=7.0 Hz, 2H), 2.44 (s, 6H), 1.96 (s, 3H), 1.30 (s, 6 H), 1.24 (t, J=7.0 Hz, 3H).

EXAMPLE 159

N-[4-(4-Amino-6,7-dimethyl-1H-imidazo[4,5-c]pyridin-1-yl)butyl]-4-[[2-(dimethylamino)ethoxy](phenyl)methyl]benzamide

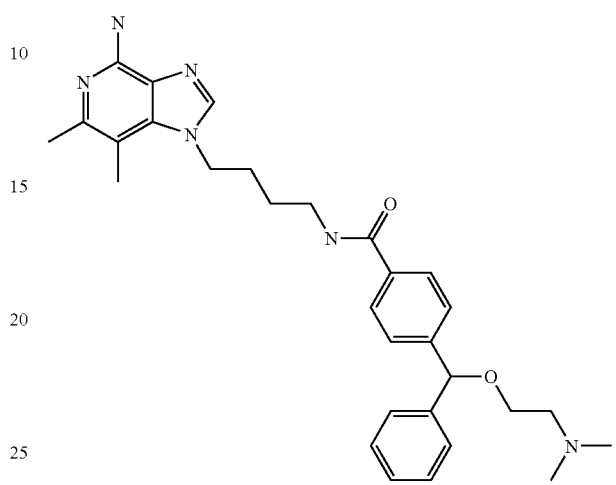

4-[[2-(Dimethylamino)ethoxy](phenyl)methyl]benzoyl chloride (1 equivalent) was added dropwise to a suspension of 4-(4-amino-6,7-dimethyl-1H-imidazo[4,5-c]pyridin-1-yl)butan-1-amine (0.22 g) in N,N-dimethylformamide (7 ml). At 1 hour, triethylamine (2 equivalents) was added followed by the addition at 2 hours of a small amount (approx. 10 mole %) of 4-dimethyaminopyridine. The reaction was maintained at room temperature overnight. The resulting mixture was poured into water and the pH was adjusted to 13. The aqueous fraction was extracted with chloroform (3×). The combined organic fractions were sequentially washed with water and brine; dried (magnesium sulfate); filtered; and concentrated to yield a yellow oil. The crude product was submitted to flash column chromatography [30 g silica gel, gradient elution: dichloromethane:methanol:triethylamine (100:0:0 to 97:2:1 to 92:7:1). A final HPLC purification using the method described above provided 83 mg of N-[4-(4-amino-6,7-dimethyl-1H-imidazo[4,5-c]pyridin-1-yl)butyl]-4-[[2-(dimethylamino)ethoxy](phenyl)methyl]benzamide as a trifluoroacetate salt.

MS (CI) m/e 515.3132 (515.3134 calcd for C$_{30}$H$_{38}$N$_6$O$_2$, M+H).

Cytokine Induction in Human Cells

An in vitro human blood cell system is used to assess cytokine induction. Activity is based on the measurement of interferon and tumor necrosis factor (α) (IFN and TNF, respectively) secreted into culture media as described by Testerman et. al. In "Cytokine Induction by the Immunomodulators Imiquimod and S-27609", Journal of Leukocyte Biology, 58, 365–372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using Histopaque®-1077. Blood is diluted 1:1 with Dulbecco's Phosphate Buffered Saline (DPBS) or Hank's Balanced Salts Solution (HBSS).

The PBMC layer is collected and washed twice with DPBS or HBSS and resuspended at 4×10⁶ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30–0.014 μM.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (30–0.014 μM). The final concentration of PBMC suspension is 2×10⁶ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (~200×g) at 4° C. The cell-free culture supernatant is removed with a sterile polypropylene pipet and transferred to sterile polypropylene tubes. Samples are maintained at −30 to −70° C. until analysis. The samples are analyzed for interferon (α) by ELISA and for tumor necrosis factor (α) by ELISA or IGEN Assay.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J. Results are expressed in pg/mL.

Tumor necrosis factor (α) (TNF) concentration is determined using ELISA kits available from Biosource International, Camarillo, Calif. Alternately, the TNF concentration can be determined by Origen® M-Series Immunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

The table below lists the lowest concentration found to induce interferon and the lowest concentration found to induce tumor necrosis factor for each compound. A "*" indicates that no induction was seen at any of the tested concentrations.

| Cytokine Induction in Human Cells | | |
|---|---|---|
| Example Number | Lowest Effective Concentration (μM) | |
| | Interferon | Tumor Necrosis Factor |
| 1 | 0.12 | 1.11 |
| 2 | 0.0046 | 0.01 |
| 3 | 0.01 | 0.37 |
| 4 | 0.12 | 0.37 |
| 5 | 0.01 | 0.12 |
| 6 | 0.01 | 0.01 |
| 7 | 0.37 | * |
| 8 | 0.04 | 10 |
| 12 | * | * |
| 27 | 0.12 | 10 |
| 28 | 30 | 30 |
| 29 | 30 | 30 |
| 30 | 10 | 10 |
| 31 | 10 | 10 |
| 32 | 10 | 30 |
| 33 | 10 | 10 |
| 34 | 10 | 30 |
| 35 | 10 | 30 |
| 36 | * | * |
| 37 | 10 | 10 |
| 38 | 10 | 30 |
| 39 | 3.33 | 30 |
| 40 | 10 | 10 |
| 41 | 10 | 10 |
| 42 | 3.33 | * |
| 43 | 3.33 | 10 |
| 44 | 3.33 | 10 |
| 45 | 3.33 | 10 |
| 46 | 3.33 | 10 |
| 47 | 3.33 | 10 |
| 48 | 3.33 | 10 |
| 49 | 3.33 | 10 |
| 50 | 3.33 | 1.11 |
| 51 | 3.33 | 10 |
| 52 | 3.33 | 3.33 |
| 53 | 3.33 | 10 |
| 54 | 1.11 | 30 |
| 55 | 3.33 | 30 |
| 56 | 1.11 | * |
| 57 | 3.33 | 10 |
| 58 | 3.33 | 30 |
| 59 | 3.33 | 10 |
| 60 | 3.33 | 10 |
| 61 | 0.37 | 3.33 |
| 62 | 1.11 | 3.33 |
| 63 | 1.11 | 3.33 |
| 64 | 1.11 | 3.33 |
| 65 | 0.37 | 3.33 |
| 66 | 3.33 | 10 |
| 67 | 1.11 | 3.33 |
| 68 | 3.33 | 3.33 |
| 69 | 1.11 | 3.33 |
| 70 | 3.33 | 10 |
| 71 | 1.11 | 3.33 |
| 72 | 3.33 | 10 |
| 73 | 1.11 | 3.33 |
| 74 | 3.33 | 10 |
| 75 | 1.11 | 3.33 |
| 76 | 0.37 | * |

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

What is claimed is:

1. A method of inducing cytokine biosynthesis in an animal comprising administering a therapeutically effective amount of a compound of the formula (I):

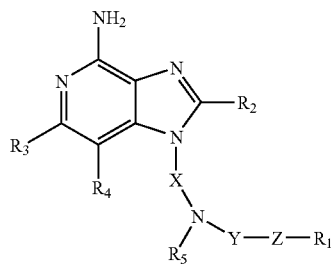

(I)

wherein
X is $C_{1-10}$ alkylene;
Y is —CO—;
Z is a bond;
$R_1$ is $C_{1-10}$ alkyl;
$R_2$ is selected from the group consisting of:
    $C_{1-4}$ alkyl,
    ethoxymethyl, and
    methoxyethyl;
$R_3$ and $R_4$ are methyl; and
$R_5$ is hydrogen;
or a pharmaceutically acceptable salt thereof to the animal; wherein the cytokine is IFN-α or TNF-α.

2. The method of claim 1 wherein X is propylene, butylene, or —CH$_2$—C(CH$_3$)$_2$—.

3. A method of inducing cytokine biosynthesis in an animal comprising administering a therapeutically effective amount of a compound of the formula (I):

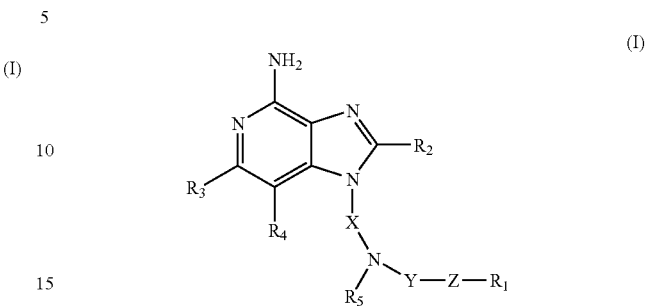

(I)

wherein
X is $C_{1-10}$ alkylene;
Y is —CO—;
Z is a bond;
$R_1$ is $C_{1-6}$ alkyl;
$R_2$ is selected from the group consisting of:
    $C_{1-4}$ alkyl,
    ethoxymethyl, and
    methoxyethyl;
$R_3$ and $R_4$ are methyl; and
$R_5$ is hydrogen, or $R_1$ and $R_5$ join to form a ring;
or a pharmaceutically acceptable salt thereof to the animal; wherein the cytokine is IFN-α or TNF-α.

4. The method of claim 3 wherein $R_1$ is $C_{1-4}$ alkyl.

* * * * *

UNITED STATES PATENT AND TRADEMARK OFFICE
CERTIFICATE OF CORRECTION

PATENT NO. : 7,098,221 B2
APPLICATION NO. : 11/200556
DATED : August 29, 2006
INVENTOR(S) : Philip D. Heppner It is certified that error appears in the above-identified patent and that said Letters Patent is hereby corrected as shown below:

Page 2 Col. 2 (Other Publications):
Line 7, Delete "Chem," and insert -- Chem., --, therefor.

Column 3:
Line 55, Delete "S-aryl:" and insert -- S-aryl; --, therefor.

Column 5:
Line 9, Delete "catlayst" and insert -- catalyst --, therefor.

Column 9:
Line 37, Delete "choride" and insert -- chloride --, therefor.

Column 18:
Line 12, After "heterocyclyl" insert -- ; --.

Column 19:
Line 13, Delete "SH;" and insert -- -SH; --, therefor.

Column 20:
Line 36, Delete "arylcarbonythio," and insert -- arylcarbonylthio, --, therefor.
Line 40-41, Delete "heteroarylalkycarbonylamino," and insert
-- heteroarylalkylcarbonylamino, --, therefor.
Line 59, Delete "substitutents," and insert -- substituents, --, therefor.

Column 22:
Line 43, Delete "greata;" and insert -- areata; --, therefor.

Column 23:
Line 25, Delete "trifluoroactic" and insert -- trifluoroacetic --, therefor.

Column 26:
Line 38, Delete "$H_2O$:" and insert -- ·$H_2O$: --, therefor.
Line 63, After "of" delete "of".

Column 27:
Line 39, Delete "$N_6S.H_2O$:" and insert -- $N_6S·H_2O$: --, therefor.

Column 28:
Line 50, Delete "reduced-pressure" and insert -- reduced pressure --, therefor.

UNITED STATES PATENT AND TRADEMARK OFFICE
CERTIFICATE OF CORRECTION

PATENT NO. : 7,098,221 B2
APPLICATION NO. : 11/200556
DATED : August 29, 2006
INVENTOR(S) : Philip D. Heppner It is certified that error appears in the above-identified patent and that said Letters Patent is hereby corrected as shown below:

<u>Column 33:</u>
Line 63, Delete "tert-butyl    4-({3-[(ethoxyacetyl)amino]" and insert -- tert-butyl 4-({3-[(ethoxyacetyl)amino] --, therefor.

<u>Column 34:</u>
Line 61, Delete "$N_5O.0.05$" and insert -- $N_5O \cdot 0.05$ --, therefor.
Line 67, After "(M+H)" insert -- . --.

<u>Column 35:</u>
Line 42, After "(M+H)" insert -- . --.

<u>Column 43:</u>
Line 20, Delete "$N_5O.0.50$" and insert -- $N_5O \cdot 0.50$ --, therefor.
Line 61, Delete "$N_5.0.25$" and insert -- $N_5 \cdot 0.25$ --, therefor.
Line 66, Delete "(CD)" and insert -- (CI) --, therefor.

<u>Column 44:</u>
Line 33, Delete "$N_5O.1.25$" and insert -- $N_5O \cdot 1.25$ --, therefor.
Line 62, Delete "Part A" and insert the same on line 61 as a heading.

<u>Column 46:</u>
Line 3, Delete "-H-" and insert -- -1H- --, therefor.
Line 41, Delete "-imidao[4,5-c]" and insert -- -imidazo[4,5-c] --, therefor.

<u>Column 48:</u>
Line 1, Delete "imidao" and insert -- imidazo --, therefor.
Line 3, Delete "$N_5O.1.00$" and insert -- $N_5O \cdot 1.00$ --, therefor.
Line 35, Delete "$N_5.2.8$ HCl." and insert -- $N_5 \cdot 2.8$ HCl˙ --, therefor.
Line 40, After "(M+H)" insert -- . --.

<u>Column 51:</u>
Line 61, Delete "Part A" and insert the same on line 60 as a heading.

<u>Column 54:</u>
Line 27, Delete "362.25.70" and insert -- 362.2570 --, therefor.

<u>Column 57</u>
Line 66, After "for" insert -- ~ --.

<u>Column 58:</u>
Line 41, Delete "diimethyl" and insert -- dimethyl --, therefor.

UNITED STATES PATENT AND TRADEMARK OFFICE
CERTIFICATE OF CORRECTION

PATENT NO. : 7,098,221 B2
APPLICATION NO. : 11/200556
DATED : August 29, 2006
INVENTOR(S) : Philip D. Heppner It is certified that error appears in the above-identified patent and that said Letters Patent is hereby corrected as shown below:

Column 62:
Line 34, Delete "(pH-12)" and insert -- (pH~12) --, therefor.

Column 64:
Line 57, Delete "et. al." and insert -- et al. --, therefor.

Signed and Sealed this

Twenty-seventh Day of March, 2007

JON W. DUDAS
*Director of the United States Patent and Trademark Office*